(12) United States Patent
Miyaji et al.

(10) Patent No.: US 8,093,251 B2
(45) Date of Patent: Jan. 10, 2012

(54) NITROGEN-CONTAINING HETEROCYCLIC COMPOUNDS AND THROMBOPOIETIN RECEPTOR ACTIVATORS

(75) Inventors: Katsuaki Miyaji, Funabashi (JP); Shunsuke Iwamoto, Funabashi (JP); Yukihiro Shigeta, Funabashi (JP); Yutaka Hirokawa, Funabashi (JP); Shingo Oowada, Funabashi (JP); Takanori Nakamura, Minamisaitama-gun (JP); Norihisa Ishiwata, Minamisaitama-gun (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 394 days.

(21) Appl. No.: 12/303,436

(22) PCT Filed: Jun. 7, 2007

(86) PCT No.: PCT/JP2007/061572
§ 371 (c)(1),
(2), (4) Date: Dec. 31, 2008

(87) PCT Pub. No.: WO2007/142308
PCT Pub. Date: Dec. 13, 2007

(65) Prior Publication Data
US 2009/0198060 A1     Aug. 6, 2009

(30) Foreign Application Priority Data
Jun. 7, 2006   (JP) .................................. 2006-158459

(51) Int. Cl.
*C07D 401/12* (2006.01)
*C07D 403/12* (2006.01)
*A61K 31/454* (2006.01)
*A61K 31/496* (2006.01)
*A61P 7/00* (2006.01)

(52) U.S. Cl. .................. 514/254.05; 514/326; 544/371; 546/211

(58) Field of Classification Search ........................ None
See application file for complete search history.

(56) References Cited

U.S. PATENT DOCUMENTS

| | | | |
|---|---|---|---|
| 5,066,695 A | 11/1991 | Cseh et al. | |
| 7,351,841 B2 * | 4/2008 | Owada et al. | 549/62 |
| 7,576,115 B2 * | 8/2009 | Owada et al. | 514/406 |
| 2003/0195231 A1 | 10/2003 | Takemoto et al. | |
| 2004/0058990 A1 | 3/2004 | Duffy et al. | |
| 2004/0063764 A1 | 4/2004 | Takemoto et al. | |
| 2004/0077697 A1 | 4/2004 | Koshio et al. | |
| 2004/0082626 A1 | 4/2004 | Takemoto et al. | |
| 2005/0153977 A1 | 7/2005 | Sugasawa et al. | |
| 2006/0069140 A1 | 3/2006 | Miyaji et al. | |
| 2008/0027068 A1 | 1/2008 | Owada et al. | |
| 2009/0118500 A1 | 5/2009 | Miyaji et al. | |

FOREIGN PATENT DOCUMENTS

| | | |
|---|---|---|
| EP | 0 349 489 A2 | 1/1990 |
| EP | 0 349 489 A3 | 1/1990 |
| EP | 1 207 155 A1 | 5/2002 |
| JP | 10 -72492 | 3/1998 |
| JP | 11-1477 | 1/1999 |
| JP | 11-152276 | 6/1999 |
| JP | 2001-097948 | 4/2001 |
| JP | 2003-238565 | 8/2003 |
| WO | WO 96/40189 | 12/1996 |
| WO | WO 96/40750 | 12/1996 |
| WO | WO 98/25965 | 6/1998 |
| WO | WO 99/11262 | 3/1999 |
| WO | WO 00/35446 | 6/2000 |
| WO | WO 00/66112 | 11/2000 |
| WO | WO 01/07423 A1 | 2/2001 |
| WO | WO 01/17349 A1 | 3/2001 |
| WO | WO 01/21180 A1 | 3/2001 |
| WO | WO 01/34585 A1 | 5/2001 |
| WO | WO 01/39773 A1 | 6/2001 |
| WO | WO 01/53267 A1 | 7/2001 |
| WO | WO 01/89457 A2 | 11/2001 |
| WO | 02 49413 | 6/2002 |
| WO | WO 02/49413 A2 | 6/2002 |
| WO | WO 02/059099 A1 | 8/2002 |
| WO | WO 02/059100 A1 | 8/2002 |
| WO | WO 02/062775 A1 | 8/2002 |
| WO | WO 02/085343 A1 | 10/2002 |
| WO | WO 03/062233 A1 | 7/2003 |
| WO | WO 03/103686 A1 | 12/2003 |
| WO | 2004 033433 | 4/2004 |

(Continued)

OTHER PUBLICATIONS

Vippagunta et al., Advanced Drug Delivery Reviews, 48 (2001), pp. 3-26.*
Jose E. Cardier. "Effects of Megakaryocyte Growth and Development Factor (Thrombopoietin) on Liver Endothelial Cells in Vitro", Microvascular Research, No. 58, 1999, pp. 108-113.
Maria Felice Brizzi, et al., "Thrombopoietin Stimulates Endothelial Cell Motility and Neoangiogenesis by a platelet-Activating Factor-Dependent Mechanism", Circ. Res., vol. 84, 1999, pp. 785-796.

(Continued)

*Primary Examiner* — Fiona T Powers
(74) *Attorney, Agent, or Firm* — Oblon, Spivak, McClelland, Maier & Neustadt, L.L.P.

(57) ABSTRACT

Compounds effective for preventing, treatment or improving diseases against which activation of the thrombopoietin receptor is effective are provided.
A compound represented by the formula (I) (wherein $R^1$, $R^2$, $R^3$, $L^1$, $L^2$, $L^3$, X and Y are defined in the description), a tautomer, prodrug or pharmaceutically acceptable salt of the compound or a solvate thereof.

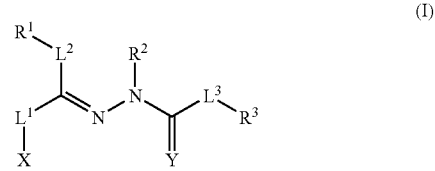

9 Claims, No Drawings

FOREIGN PATENT DOCUMENTS

| | | |
|---|---|---|
| WO | WO 2004/033433 A1 | 4/2004 |
| WO | WO 2004/108683 A1 | 12/2004 |
| WO | 2006 062240 | 6/2006 |
| WO | WO 2006/062240 A1 | 6/2006 |
| WO | WO 2007/010954 A1 | 1/2007 |

OTHER PUBLICATIONS

"Cell migration, Growth Factors and Chemokines in Stem Cell Biology", Blood, vol. 98, 2001, pp. 71a and 72a.

U.S. Appl. No. 12/092,834, filed May 7, 2008, Miyaji, et al.

U.S. Appl. No. 11/721,252, filed Jun. 8, 2007, Miyaji, et al.

U.S. Appl. No. 11/721,786, filed Jun. 14, 2007, Miyaji, et al.

U.S. Appl. No. 11/994,502, filed Jan. 3, 2008, Miyaji, et al.

U.S. Appl. No. 11/995,070, filed Jan. 8, 2008, Miyaji, et al.

Extended Search Report issued Mar. 7, 2011 in Europe Application No. 07744900.7.

Database CA, "Sythesis and characterization of lanthanide (III) complexes of 1-phenyl-3-methyl-5-hydroxy-4-pyrazolyl propionyl-2'-picolinoyl hydrazone", Database accession No. 2005:38342 ; & Asian Journal of Chemistry, Abstract, 2005, vol. 17, No. 1, pp. 581-586.

Database CA, "Synthesis, structure and antifungal activity of 2-methyl-3-carbethoxy-5-pyrrolinone derivatives", Database accession No. 1993:124336; & Acta Pharmaceutica, Abstract, 1992, vol. 42, pp. 195-201.

El-Sawaf, Ayman K. et al., "Copper(II) complexes of 4-formylantipyrine N(4)-substituted thiosemicarbazones", Transition Met. Chem., vol. 22, No. 4, pp. 360-365, (1997).

U.S. Appl. No. 12/492,435, filed Jun. 26, 2009, Owada, et al.

* cited by examiner

– 1 –

NITROGEN-CONTAINING HETEROCYCLIC COMPOUNDS AND THROMBOPOIETIN RECEPTOR ACTIVATORS

TECHNICAL FIELD

The present invention relates to preventive, therapeutic and improving agents having affinity for and agonistic action on the thrombopoietin receptor for diseases against which activation of the thrombopoietin receptor is effective. Specifically, it relates to pharmaceutical compositions comprising compounds which increase platelets through stimulation of differentiation and proliferation of hematopoietic stem cells, megakaryocytic progenitor cells and megakaryocytes or compounds for therapeutic angiogenesis or with anti-arteriosclerosis action that stimulate differentiation and proliferation of vascular endothelial cells and endothelial progenitor cells.

BACKGROUND ART

Thrombopoietin is a cytokine consisting of 332 amino acids that increases platelet production by stimulating differentiation and proliferation of hematopoietic stem cells, megakaryocytic progenitor cells and megakaryocytes mediated by its receptor and therefore is promising as a drug for hematological disorders. Recent reports that it stimulates differentiation and proliferation of vascular endothelial cells and endothelial progenitor cells have raised expectations of therapeutic angiogenesis, anti-arteriosclerosis and prevention of cardiovascular events (for example, non-patent document 1, non-patent document 2 and non-patent document 3).

Biologically active substances which have been known so far to regulate platelet production through the thrombopoietin receptor include, in addition to thrombopoietin itself, low molecular weight peptides having affinity for the thrombopoietin receptor (for example, patent document 1, patent document 2, patent document 3 and patent document 4).

As a result of search for nonpeptidic low molecular weight compounds that increase platelet production mediated by the thrombopoietin receptor, low molecular weight compounds having affinity for the thrombopoietin receptor have been reported (for example, patent document 5 to patent document 27).

Patent document 1: JP-A-10-72492
Patent document 2: WO96/40750
Patent document 3: WO96/40189
Patent document 4: WO98/25965
Patent document 5: JP-A-11-1477
Patent document 6: JP-A-11-152276
Patent document 7: WO01/07423
Patent document 8: WO01/53267
Patent document 9: WO02/059099
Patent document 10: WO02/059100
Patent document 11: WO00/35446
Patent document 12: WO00/66112
Patent document 13: WO01/34585
Patent document 14: WO01/17349
Patent document 15: WO01/39773
Patent document 16: WO01/21180
Patent document 17: WO01/89457
Patent document 18: WO02/49413
Patent document 19: WO02/085343
Patent document 20: WO03/103686
Patent document 21: JP-A-2001-97948
Patent document 22: WO99/11262
Patent document 23: WO02/062775

Patent document 24: WO03/062233
Patent document 25 JP-A-2003-238565
Patent document 26: WO04/033433
Patent document 27: WO04/108683
Non-patent document 1: Microvasc. Res., 1999: 58, p. 108-113
Non-patent document 2: Circ. Res., 1999: 84, p. 785-796
Non-patent document 3: Blood 2001:98, p. 71a-72a

Problems that the Invention it to Solve

Thrombopoietin and low molecular weight peptides having affinity for the thrombopoietin receptor are likely to be easily degraded in the gastrointestinal tract and are usually difficult to orally administer. As to thrombopoietin itself, the appearance of anti-thrombopoietin antibodies have been reported.

Besides, though it is probably possible to orally administer nonpeptidic low molecular weight compounds, no practical drugs have been put on the market.

Therefore, orally administrable low molecular weight compounds having excellent affinity for and agonistic action on the thrombopoietin receptor as preventive, therapeutic and improving agents for diseases against which activation of the thrombopoietin receptor is effective have been demanded. Specifically, low molecular weight compounds which can serve as platelet increasing agents or increasing agents for other blood cells by stimulating differentiation and proliferation of hematopoietic stem cells, megakaryocytic progenitor cells and megakaryocytes or low molecular weight compounds which can be used for therapeutic angiogenesis or as preventive and therapeutic agents for arteriosclerosis by stimulating endothelial cells and endothelial progenitor cells have been demanded.

Means for Solving the Problems

The present inventors conducted extensive research to find low molecular weight compounds having affinity for and agonistic action on the thrombopoietin receptor, and as a result, found that the compounds represented by the following formula (I) have high affinity and agonistic action which enable them to show potent platelet increasing action by stimulating differentiation and proliferation of megakaryocytic progenitor cells and megakaryocytes. The present invention was accomplished on the basis of this discovery.

Namely, the present invention relates to:
1. A compound represented by the formula (I):

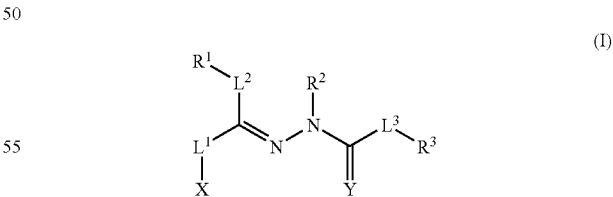

(I)

wherein each of $R^1$ and $R^2$ independently means a hydrogen atom, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group and the $C_{1-10}$ alkylcarbonyl group may optionally be substituted with one or more substituents each of which is independently represented by —$V^1$ (wherein $V^1$ means a carboxyl group, a carbamoyl group, a sulfamoyl group, a phosphono group, a sulfo group, a tetrazole group, a formyl group, a nitro group, a cyano group, a halogen atom, an oxo group, a $C_{1-3}$ alkyl group, a $C_{1-3}$ alkoxy group (the $C_{1-3}$ alkyl group and the $C_{1-3}$ alkoxy group are optionally substituted with one or more halogen atoms), a thiol group, a protected thiol group, a hydroxyl group, a protected hydroxyl group, an amino group, a protected amino group, a $C_{1-10}$ thioalkyl group, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, a $C_{1-10}$ alkylaminocarbonyl group, a $C_{1-10}$ alkylsulfonyl group, a $C_{1-10}$ alkylsulfonylamino group, a $C_{1-10}$ alkylaminosulfonyl group, a $C_{1-10}$ mono- or di-alkylamino group, a $C_{2-14}$ aryl group, a $C_{2-14}$ aryloxy group or a $C_{2-9}$ heterocyclyl group (the $C_{1-10}$ thioalkyl group, the $C_{1-10}$ alkoxy group, the $C_{1-10}$ alkylcarbonyl group, the $C_{1-10}$ alkylcarbonyloxy group, the $C_{1-10}$ alkoxycarbonyl group, the $C_{1-10}$ alkylcarbonylamino group, the $C_{1-10}$ alkylaminocarbonyl group, the $C_{1-10}$ alkylsulfonyl group, the $C_{1-10}$ alkylsulfonylamino group, the $C_{1-10}$ alkylaminosulfonyl group, the $C_{1-10}$ mono- or di-alkylamino group, the $C_{2-14}$ aryl group, the $C_{2-14}$ aryloxy group and the $C_{2-9}$ heterocyclyl group may be substituted with one or more carboxyl groups, one or more carbamoyl groups, one or more sulfamoyl groups, one or more phosphono groups, one or more sulfo groups, one or more tetrazole groups, one or more formyl groups, one or more nitro groups, one or more cyano groups, one or more halogen atoms, one or more $C_{1-3}$ alkyl groups, one or more $C_{1-3}$ alkoxy groups (the $C_{1-3}$ alkyl groups and the $C_{1-3}$ alkoxy groups are optionally substituted with one or more halogen atoms), one or more thiol groups, one or more protected thiol groups, one or more hydroxyl groups, one or more protected hydroxyl groups, one or more amino groups, one or more protected amino groups, one or more $C_{1-10}$ thioalkyl groups, one or more $C_{1-10}$ alkoxy groups, one or more $C_{1-10}$ alkylcarbonyl groups, one or more alkylcarbonyloxy groups, one or more $C_{1-10}$ alkoxycarbonyl groups, one or more $C_{1-10}$ alkylcarbonylamino groups, one or more $C_{1-10}$ alkylaminocarbonyl groups, one or more $C_{1-10}$ alkylsulfonyl groups, one or more $C_{1-10}$ alkylsulfonylamino groups, one or more $C_{1-10}$ alkylaminosulfonyl groups, one or more $C_{1-10}$ mono- or di-alkylamino groups, one or more $C_{2-14}$ aryl groups, one or more $C_{2-14}$ aryloxy groups or one or more $C_{2-9}$ heterocyclyl groups (the $C_{2-14}$ aryl groups, the $C_{2-14}$ aryloxy groups and the $C_{2-9}$ heterocyclyl groups may be substituted with one or more $C_{1-6}$ alkyl groups, one or more $C_{1-6}$ alkoxy groups (the $C_{1-6}$ alkyl groups and the $C_{1-6}$ alkoxy groups may be substituted with one or more halogen atoms) or one or more halogen atoms)))), a $C_{2-14}$ aryl group (the $C_{2-14}$ aryl group may optionally be substituted with one or more substituents each of which is independently represented by —$V^2$ (wherein $V^2$ means a $C_{1-10}$ alkyl group, a $C_{2-6}$ alkenyl group, a $C_{2-6}$ alkynyl group (the $C_{1-10}$ alkyl group, the $C_{2-6}$ alkenyl group and the $C_{2-6}$ alkynyl group may be substituted with one or more halogen atoms) or —$V^3$ (wherein $V^3$ is the same as $V^1$, and $V^1$ is the same as defined above))) or a $C_{2-9}$ heterocyclyl group (the $C_{2-9}$ heterocyclyl group may optionally be substituted with one or more substituents each of which is independently represented by —$V^4$ (wherein $V^4$ is the same as $V^2$, and $V^2$ is the same as defined above)), $R^3$ means a $C_{2-9}$ nitrogen-containing heterocyclyl group (the $C_{2-9}$ nitrogen-containing heterocyclyl group may optionally be substituted with one or more substituents each of which is independently represented by —$V^5$ (wherein $V^5$ means —$W^1(CW^2W^3)_mW^4$ (wherein $W^1$ means $(CR^4R^5)_n$ (wherein each of $R^4$ and $R^5$ independently means a hydrogen atom, a hydroxyl group, an amino group, a $C_{1-6}$ alkyl group or a $C_{1-6}$ alkoxy group (the $C_{1-6}$ alkyl group and the $C_{1-6}$ alkoxy group may be substituted with one or more halogen atoms), and n means 0, 1, 2 or 3), an oxygen atom, a sulfur atom or $NR^6$ (wherein $R^6$ means a hydrogen atom, a $C_{1-6}$ alkyl group, a formyl group or a $C_{1-6}$ alkylcarbonyl group), each of $W^2$ and $W^3$ independently means a hydrogen atom, a $C_{1-3}$ alkyl group (the $C_{1-3}$ alkyl group may be substituted with one or more halogen atoms) or together with each other means (=O) or (=S), m means 0, 1, 2 or 3, and $W_4$ means a hydrogen atom, a hydroxyl group, a protected hydroxyl group, a thiol group, a protected thiol group, an amino group, a protected amino group, a formyl group, a nitro group, a cyano group, a halogen atom, a tetrazole group, a phosphono group, a $C_{1-10}$ alkyl group, a $C_{2-6}$ alkenyl group, a $C_{2-6}$ alkynyl group, a $C_{1-10}$ thioalkyl group, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, a $C_{1-10}$ alkylaminocarbonyl group, a $C_{1-10}$ mono- or di-alkylamino group (the $C_{1-10}$ alkyl group, the $C_{2-6}$ alkenyl group, the $C_{2-6}$ alkynyl group, the $C_{1-10}$ thioalkyl group, the $C_{1-10}$ alkoxy group, the $C_{1-10}$ alkylcarbonyl group, the $C_{1-10}$ alkylcarbonyloxy group, the $C_{1-10}$ alkoxycarbonyl group, the $C_{1-10}$ alkylcarbonylamino group, the $C_{1-10}$ alkylaminocarbonyl group and the $C_{1-10}$ mono- or di-alkylamino group may optionally be substituted with one or more substituents each of which is independently represented by —$V^6$ (wherein $V^6$ is the same as $V^1$, and $V^1$ is the same as defined above)), a $C_{2-14}$ aryl group, a $C_{2-14}$ aryloxy group, a $C_{2-9}$ heterocyclyl group (the $C_{2-14}$ aryl group, the $C_{2-14}$ aryloxy group and the $C_{2-9}$ heterocyclyl group may optionally be substituted with one or more substituents each of which is independently represented by —$V^7$ (wherein $V^7$ is the same as $V^2$, and $V^2$ is the same as defined above)), —$SO_2R^7$, —$SOR^7$ or —$COR^7$ (wherein $R^7$ means a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may optionally be substituted with one or more substituents each of which is independently represented by —$V^8$ (wherein $V^8$ is the same as $V^1$, and $V^1$ is the same as defined above)), a $C_{2-14}$ aryl group, a $C_{2-14}$ aryloxy group, a $C_{2-9}$ heterocyclyl group (the $C_{2-14}$ aryl group, the $C_{2-14}$ aryloxy group and the $C_{2-9}$ heterocyclyl group may optionally be substituted with one or more substituents each of which is independently represented by —$V^9$ (wherein $V^9$ is the same as $V^2$, and $V^2$ is the same as defined above)) or $NR^8R^9$ (wherein each of $R^8$ and $R^9$ independently means a hydrogen atom, a hydroxyl group, a formyl group, a carbamoyl group, a sulfamoyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, a $C_{1-10}$ alkylaminocarbonyl group, a $C_{1-10}$ alkylsulfonyl group, a $C_{1-10}$ alkylaminosulfonyl group, a $C_{1-10}$ mono- or di-alkylamino group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyl group, the $C_{1-10}$ alkylcarbonyloxy group, the $C_{1-10}$ alkoxycarbonyl group, the $C_{1-10}$ alkylcarbonylamino group, the $C_{1-10}$ alkylaminocarbonyl group, the $C_{1-10}$ alkylsulfonyl group, the $C_{1-10}$ alkylaminosulfonyl group and the $C_{1-10}$ mono- or di-alkylamino group may optionally be substituted with one or more substituents each of which is independently represented by —$V^{10}$ (wherein $V^{10}$ is the same as $V^1$, and $V^1$ is the same as defined above)), a $C_{2-14}$ aryl group or a $C_{2-9}$ heterocyclyl group (the $C_{2-14}$ aryl group and the $C_{2-9}$ heterocyclyl group may optionally be substituted with one or more substituents each of which is independently represented by —$V^{11}$ (wherein $V^{11}$ is the same as $V^2$, and $V^2$ is the same as defined above))))))) or a $C_{1-6}$ alkyl group (the $C_{1-6}$ alkyl group may optionally be substituted with one or more substituents each of which is independently represented by —V¹² (wherein V¹² is the same as V¹, and V¹ is the same as defined above) and is substituted with a C$_{2-9}$ nitrogen-containing heterocyclyl group (the C$_{2-9}$ nitrogen-containing heterocyclyl group may optionally be substituted with one or more substituents each of which is independently represented by —V¹³ (wherein V¹³ is the same as V⁵, and V⁵ is the same as defined above))), L¹ means the formula (II):

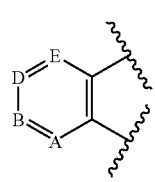

(II)

(the group represented by the formula (II) may be fused with a C$_{2-14}$ aryl group, a C$_{3-7}$ carbocyclyl group or a C$_{2-9}$ heterocyclyl group (the C$_{2-14}$ aryl group, the C$_{3-7}$ carbocyclyl group and the C$_{2-9}$ heterocyclyl group may optionally substituted with one or more substituents each of which is independently represented by —V¹⁴ (wherein V¹⁴ is the same as V², and V² is the same as defined above)) at arbitrary two positions, and each of A, B, D and E independently means CR¹⁰ (wherein R¹⁰ is a hydrogen atom, a carboxyl group, a carbamoyl group, a sulfamoyl group, a thiol group, a phosphono group, a sulfo group, a tetrazole group, a formyl group, a nitro group, a cyano group, a halogen atom, a C$_{1-3}$ alkyl group, a C$_{1-3}$ alkoxy group (the C$_{1-3}$ alkyl group and the C$_{1-3}$ alkoxy group are optionally substituted with one or more halogen atoms), a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, a C$_{1-10}$ alkylaminocarbonyl group, a C$_{1-10}$ alkylsulfonyl group, a C$_{1-10}$ alkylsulfonylamino group, a C$_{1-10}$ alkylaminosulfonyl group, an amino group, a C$_{1-10}$ mono- or di-alkylamino group, a hydroxyl group, a protected hydroxyl group, a C$_{1-10}$ alkyl group, a C$_{2-6}$ alkenyl group, a C$_{2-6}$ alkynyl group (the C$_{1-10}$ alkoxy group, the C$_{1-10}$ alkylcarbonyl group, the C$_{1-10}$ alkylcarbonyloxy group, the C$_{1-10}$ alkoxycarbonyl group, the C$_{1-10}$ alkylcarbonylamino group, the C$_{1-10}$ alkylaminocarbonyl group, the C$_{1-10}$ alkylsulfonyl group, the C$_{1-10}$ alkylsulfonylamino group, the C$_{1-10}$ alkylaminosulfonyl group, the amino group, the C$_{1-10}$ mono- or di-alkylamino group, the hydroxyl group, the protected hydroxyl group, the C$_{1-10}$ alkyl group, the C$_{2-6}$ alkenyl group and the C$_{2-6}$ alkynyl group may optionally be substituted with one or more substituents each of which is independently represented by —V¹⁵ (wherein V¹⁵ is the same as V¹, and V¹ is the same as defined above)), a C$_{2-14}$ aryl group, a C$_{2-14}$ aryloxy group or a C$_{2-9}$ heterocyclyl group (the C$_{2-14}$ aryl group, the C$_{2-14}$ aryloxy group and the C$_{2-9}$ heterocyclyl group may be substituted with one or more substituents each of which is independently represented by —V¹⁶ (wherein V¹⁶ is the same as V², and V² is the same as defined above))) or a nitrogen atom, or A=B or D=E means, as a whole, an oxygen atom, a sulfur atom or NR¹¹ (wherein R¹¹ is the same as R¹⁰, and R¹⁰ is the same as defined above)), L² means a single bond, CR¹²R¹³ (wherein each of R¹² and R¹³ independently means a hydrogen atom, a C$_{1-3}$ alkyl group (the C$_{1-3}$ alkyl group may optionally be substituted with one or more halogen atoms) or a halogen atom), an oxygen atom, a sulfur atom or NR¹⁴ (wherein R¹⁴ means a hydrogen atom, a formyl group or a C$_{1-3}$ alkyl group (the C$_{1-3}$ alkyl group may optionally be substituted with one or more halogen atoms)), L³ means a single bond or NR¹⁵ (wherein R¹⁵ is a hydrogen atom, a formyl group, a C$_{1-10}$ alkyl group, a C$_{2-6}$ alkenyl group, a C$_{2-6}$ alkynyl group, a C$_{1-10}$ alkoxy group, a C$_{1-10}$ alkylcarbonyl group, a C$_{1-10}$ alkoxycarbonyl group, a C$_{1-10}$ alkylaminocarbonyl group, a C$_{1-10}$ alkylsulfonyl group, a C$_{1-10}$ alkylaminosulfonyl group (the C$_{1-10}$ alkyl group, the C$_{2-6}$ alkenyl group, the C$_{2-6}$ alkynyl group, the C$_{1-10}$ alkoxy group, the C$_{1-10}$ alkylcarbonyl group, the C$_{1-10}$ alkoxycarbonyl group, the C$_{1-10}$ alkylaminocarbonyl group, the C$_{1-10}$ alkylsulfonyl group and the C$_{1-10}$ alkylaminosulfonyl group may optionally be substituted with one or more carboxyl groups, one or more carbamoyl groups, one or more sulfamoyl groups, one or more formyl groups, one or more nitro groups, one or more cyano groups, one or more halogen atoms, one or more hydroxyl groups, one or more protected hydroxyl groups, one or more amino groups, one or more protected amino groups or one or more C$_{1-10}$ mono- or di-alkylamino groups)), X means OR¹⁶, SR¹⁶ (wherein R¹⁶ means a hydrogen atom, a C$_{1-10}$ alkyl group, a C$_{2-6}$ alkenyl group, a C$_{2-6}$ alkynyl group or a C$_{1-10}$ alkylcarbonyl group (the C$_{1-10}$ alkyl group, the C$_{2-6}$ alkenyl group, the C$_{2-6}$ alkynyl group and the C$_{1-10}$ alkylcarbonyl group may optionally be substituted with one or more substituents each of which is independently represented by —V¹⁷ (wherein V¹⁷ is the same as V¹, and V¹ is the same as defined above))), NR¹⁷R¹⁸ (wherein each of R¹⁷ and R¹⁸ independently means a hydrogen atom, a formyl group, a C$_{1-10}$ alkyl group, a C$_{2-6}$ alkenyl group, a C$_{2-6}$ alkynyl group, a C$_{1-10}$ alkoxy group, a C$_{1-10}$ alkylcarbonyl group (the C$_{1-10}$ alkyl group, the C$_{2-6}$ alkenyl group, the C$_{2-6}$ alkynyl group, the C$_{1-10}$ alkoxy group and the C$_{1-10}$ alkylcarbonyl group may optionally be substituted with one or more substituents each of which is independently represented by —V¹⁸ (wherein V¹⁸ is the same as V¹, and V¹ is the same as defined above)), a C$_{2-14}$ aryl group or a C$_{2-9}$ heterocyclyl group (the C$_{2-14}$ aryl group and the C$_{2-9}$ heterocyclyl group may optionally be substituted with one or more substituents each of which is independently represented by —V¹⁹ (wherein V¹⁹ is the same as V², and V² is the same as defined above))), a C$_{2-9}$ heterocyclyl group (the C$_{2-9}$ heterocyclyl group may optionally be substituted with one or more substituents each of which is independently represented by —V²⁰ (wherein V²⁰ is the same as V¹, and V¹ is the same as defined above)), COR¹⁹ or SO$_2$R²⁰ (wherein each of R¹⁹ and R²⁰ means a hydrogen atom, a hydroxyl group, a protected hydroxyl group, an amino group, a protected amino group, a C$_{1-10}$ alkyl group, a C$_{2-6}$ alkenyl group, a C$_{2-6}$ alkynyl group, a C$_{1-3}$ alkyl group, a C$_{1-3}$ alkoxy group (the C$_{1-3}$ alkyl group and the C$_{1-3}$ alkoxy group are optionally substituted with one or more halogen atoms), a C$_{1-10}$ alkoxy group, a C$_{1-10}$ mono- or di-alkylamino group, a C$_{2-14}$ aryl group, a C$_{2-14}$ aryloxy group or a C$_{2-9}$ heterocyclyl group (the C$_{1-10}$ alkoxy group, the C$_{1-10}$ mono- or di-alkylamino group, the C$_{2-14}$ aryl group, the C$_{2-14}$ aryloxy group and the C$_{2-9}$ heterocyclyl group may optionally be substituted with one or more substituents each of which is independently represented by —V²¹ (wherein V²¹ is the same as V¹, and V¹ is the same as defined above))), and Y means an oxygen atom, a sulfur atom or NR²¹ (wherein R²¹ means a hydrogen atom, a formyl group, a hydroxyl group, a C$_{1-10}$ alkyl group, a C$_{2-6}$ alkenyl group, a C$_{2-6}$ alkynyl group, a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, a C$_{1-10}$ alkylaminocarbonyl group, a C$_{1-10}$ alkylsulfonyl group, a C$_{1-10}$ alkylsulfonylamino group, a C$_{1-10}$ alkylaminosulfonyl group, a C$_{1-10}$ mono- or di-alkylamino group, a C$_{2-14}$ aryl group, a C$_{2-14}$ aryloxy group or a C$_{2-9}$ heterocyclyl group (the C$_{1-10}$ alkyl group, the C$_{2-6}$ alkenyl group, the C$_{2-6}$ alkynyl group, the C$_{1-10}$ alkoxy group, the C$_{1-10}$ alkylcarbonyl group, the C$_{1-10}$ alkylcarbonyloxy group, the C$_{1-10}$ alkoxycarbonyl group, the C$_{1-10}$ alkylcarbonylamino group, the C$_{1-10}$ alkylaminocarbonyl group, the C$_{1-10}$ alkylsulfonyl group, the C$_{1-10}$ alkylsulfonylamino group, the C$_{1-10}$ alkylaminosulfonyl group, the C$_{1-10}$ mono- or di-alkylamino group, the C$_{2-14}$ aryl group, the C$_{2-14}$ aryloxy group and the C$_{2-9}$ heterocyclyl group may optionally be substituted with one or more substituents each of which is independently represented by —V$^{22}$ (wherein V$^{22}$ is the same as V$^1$, and V$^1$ is the same as defined above))), a tautomer, prodrug or pharmaceutically acceptable salt of the compound or a solvate thereof.

2. The compound according to 1, wherein L$^1$ means the formula (II):

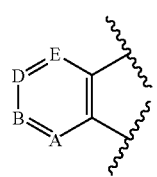

(II)

(wherein A means CR$^a$, B means CR$^b$ (wherein each of R$^a$ and R$^b$ independently means a hydrogen atom, a carboxyl group, a carbamoyl group, a sulfamoyl group, a thiol group, a phosphono group, a sulfo group, a tetrazole group, a formyl group, a nitro group, a cyano group, a halogen atom, a C$_{1-3}$ alkyl group, a C$_{1-3}$ alkoxy group (the C$_{1-3}$ alkyl group and the C$_{1-3}$ alkoxy group are optionally substituted with one or more halogen atoms), a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, a C$_{1-10}$ alkylaminocarbonyl group, a C$_{1-10}$ alkylsulfonyl group, a C$_{1-10}$ alkylsulfonylamino group, a C$_{1-10}$ alkylaminosulfonyl group, an amino group, a C$_{1-10}$ mono- or di-alkylamino group, a hydroxyl group, a protected hydroxyl group, a C$_{1-10}$ alkyl group, a C$_{2-6}$ alkenyl group, a C$_{2-6}$ alkynyl group (the C$_{1-10}$ alkoxy group, the C$_{1-10}$ alkylcarbonyl group, the C$_{1-10}$ alkylcarbonyloxy group, the C$_{1-10}$ alkoxycarbonyl group, the C$_{1-10}$ alkylcarbonylamino group, the C$_{1-10}$ alkylaminocarbonyl group, the C$_{1-10}$ alkylsulfonyl group, the C$_{1-10}$ alkylsulfonylamino group, the C$_{1-10}$ alkylaminosulfonyl group, the amino group, the C$_{1-10}$ mono- or di-alkylamino group, the hydroxyl group, the protected hydroxyl group, the C$_{1-10}$ alkyl group, the C$_{2-6}$ alkenyl group and the C$_{2-6}$ alkynyl group may optionally be substituted with one or more substituents each of which is independently represented by —V$^{15}$ (wherein V$^{15}$ is the same as V$^1$, and V$^1$ is the same as defined above)), a C$_{2-14}$ aryl group, a C$_{2-14}$ aryloxy group or a C$_{2-9}$ heterocyclyl group (the C$_{2-14}$ aryl group, the C$_{2-14}$ aryloxy group and the C$_{2-9}$ heterocyclyl group may be substituted with one or more substituents each of which is independently represented by —V$^{16}$ (wherein V$^{16}$ is the same as V$^2$, and V$^2$ is the same as defined above))), and D=E means a sulfur atom), a tautomer, prodrug or pharmaceutically acceptable salt of the compound or a solvate thereof.

3. The compound according to 1, wherein L$^1$ means the formula (II):

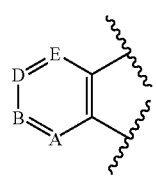

(II)

(wherein A=B means NR$^a$, D means CR$^b$, and E means CR$^c$ (wherein each of R$^a$, R$^b$ and R$^c$ independently means a hydrogen atom, a carboxyl group, a carbamoyl group, a sulfamoyl group, a thiol group, a phosphono group, a sulfo group, a tetrazole group, a formyl group, a nitro group, a cyano group, a halogen atom, a C$_{1-3}$ alkyl group, a C$_{1-3}$ alkoxy group (the C$_{1-3}$ alkyl group and the C$_{1-3}$ alkoxy group are optionally substituted with one or more halogen atoms), a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, a C$_{1-10}$ alkylaminocarbonyl group, a C$_{1-10}$ alkylsulfonyl group, a C$_{1-10}$ alkylsulfonylamino group, a C$_{1-10}$ alkylaminosulfonyl group, an amino group, a C$_{1-10}$ mono- or di-alkylamino group, a hydroxyl group, a protected hydroxyl group, a C$_{1-10}$ alkyl group, a C$_{2-6}$ alkenyl group, a C$_{2-6}$ alkynyl group (the C$_{1-10}$ alkoxy group, the C$_{1-10}$ alkylcarbonyl group, the C$_{1-10}$ alkylcarbonyloxy group, the C$_{1-10}$ alkoxycarbonyl group, the C$_{1-10}$ alkylcarbonylamino group, the C$_{1-10}$ alkylaminocarbonyl group, the C$_{1-10}$ alkylsulfonyl group, the C$_{1-10}$ alkylsulfonylamino group, the C$_{1-10}$ alkylaminosulfonyl group, the amino group, the C$_{1-10}$ mono- or di-alkylamino group, the hydroxyl group, the protected hydroxyl group, the C$_{1-10}$ alkyl group, the C$_{2-6}$ alkenyl group and the C$_{2-6}$ alkynyl group may optionally be substituted with one or more substituents each of which is independently represented by —V$^{15}$ (wherein V$^{15}$ is the same as V$^1$, and V$^1$ is the same as defined above)), a C$_{2-14}$ aryl group, a C$_{2-14}$ aryloxy group or a C$_{2-9}$ heterocyclyl group (the C$_{2-14}$ aryl group, the C$_{2-14}$ aryloxy group and the C$_{2-9}$ heterocyclyl group may be substituted with one or more substituents each of which is independently represented by —V$^{16}$ (wherein V$^{16}$ is the same as V$^2$, and V$^2$ is the same as defined above))))), a tautomer, prodrug or pharmaceutically acceptable salt of the compound or a solvate thereof.

4. The compound according to 1, wherein L$^1$ means the formula (II):

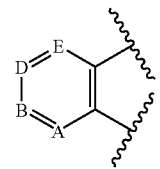

(II)

(wherein A=B means NR$^a$, D means a nitrogen atom, and E means CR$^b$ (wherein each of R$^a$ and R$^b$ independently means a hydrogen atom, a carboxyl group, a carbamoyl group, a sulfamoyl group, a thiol group, a phosphono group, a sulfo group, a tetrazole group, a formyl group, a nitro group, a cyano group, a halogen atom, a C$_{1-3}$ alkyl group, a C$_{1-3}$ alkoxy group (the C$_{1-3}$ alkyl group and the C$_{1-3}$ alkoxy group are optionally substituted with one or more halogen atoms), a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, a C$_{1-10}$ alkylaminocarbonyl group, a C$_{1-10}$ alkylsulfonyl group, a C$_{1-10}$ alkylsulfonylamino group, a C$_{1-10}$ alkylaminosulfonyl group, an amino group, a C$_{1-10}$ mono- or di-alkylamino group, a hydroxyl group, a protected hydroxyl group, a C$_{1-10}$ alkyl group, a C$_{2-6}$ alkenyl group, a C$_{2-6}$ alkynyl group (the C$_{1-10}$ alkoxy group, the C$_{1-10}$ alkylcarbonyl group, the C$_{1-10}$ alkylcarbonyloxy group, the C$_{1-10}$ alkoxycarbonyl group, the C$_{1-10}$ alkylcarbonylamino group, the C$_{1-10}$ alkylaminocarbonyl group, the C$_{1-10}$ alkylsulfonyl group, the C$_{1-10}$ alkylsulfonylamino group, the C$_{1-10}$ alkylaminosulfonyl group, the amino group, the C$_{1-10}$ mono- or di-alkylamino group, the hydroxyl group, the protected hydroxyl group, the C$_{1-10}$ alkyl group, the C$_{2-6}$ alkenyl group and the C$_{2-6}$ alkynyl group may optionally be substituted with one or more substituents each of which is independently represented by —V$^{15}$ (wherein V$^{15}$ is the same as V$^1$, and V$^1$ is the same as defined above)), a C$_{2-14}$ aryl group, a C$_{2-14}$ aryloxy group or a C$_{2-9}$ heterocyclyl group (the C$_{2-14}$ aryl group, the C$_{2-14}$ aryloxy group and the C$_{2-9}$ heterocyclyl group may be substituted with one or more substituents each of which is independently represented by —V$^{16}$ (wherein V$^{16}$ is the same as V$^2$, and V$^2$ is the same as defined above)))), a tautomer, prodrug or pharmaceutically acceptable salt of the compound or a solvate thereof.

5. The compound according to 1, wherein L$^1$ means the formula (II):

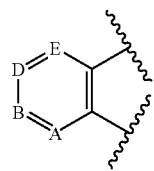

(II)

(wherein A means CR$^a$, B means a nitrogen atom, and D=E means NR$^b$ (wherein each of R$^a$ and R$^b$ independently means a hydrogen atom, a carboxyl group, a carbamoyl group, a sulfamoyl group, a thiol group, a phosphono group, a sulfo group, a tetrazole group, a formyl group, a nitro group, a cyano group, a halogen atom, a C$_{1-3}$ alkyl group, a C$_{1-3}$ alkoxy group (the C$_{1-3}$ alkyl group and the C$_{1-3}$ alkoxy group are optionally substituted with one or more halogen atoms), a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, a C$_{1-10}$ alkylaminocarbonyl group, a C$_{1-10}$ alkylsulfonyl group, a C$_{1-10}$ alkylsulfonylamino group, a C$_{1-10}$ alkylaminosulfonyl group, an amino group, a C$_{1-10}$ mono- or di-alkylamino group, a hydroxyl group, a protected hydroxyl group, a C$_{1-10}$ alkyl group, a C$_{2-6}$ alkenyl group, a C$_{2-6}$ alkynyl group (the C$_{1-10}$ alkoxy group, the C$_{1-10}$ alkylcarbonyl group, the C$_{1-10}$ alkylcarbonyloxy group, the C$_{1-10}$ alkoxycarbonyl group, the C$_{1-10}$ alkylcarbonylamino group, the C$_{1-10}$ alkylaminocarbonyl group, the C$_{1-10}$ alkylsulfonyl group, the C$_{1-10}$ alkylsulfonylamino group, the C$_{1-10}$ alkylaminosulfonyl group, the amino group, the C$_{1-10}$ mono- or di-alkylamino group, the hydroxyl group, the protected hydroxyl group, the C$_{1-10}$ alkyl group, the C$_{2-6}$ alkenyl group and the C$_{2-6}$ alkynyl group may optionally be substituted with one or more substituents each of which is independently represented by —V$^{15}$ (wherein V$^{15}$ is the same as V$^1$, and V$^1$ is the same as defined above)), a C$_{2-14}$ aryl group, a C$_{2-14}$ aryloxy group or a C$_{2-9}$ heterocyclyl group (the C$_{2-14}$ aryl group, the C$_{2-14}$ aryloxy group and the C$_{2-9}$ heterocyclyl group may be substituted with one or more substituents each of which is independently represented by —V$^{16}$ (wherein V$^{16}$ is the same as V$^2$, and V$^2$ is the same as defined above)))), a tautomer, prodrug or pharmaceutically acceptable salt of the compound or a solvate thereof.

6. The compound according to 1, wherein L$^1$ means the formula (II):

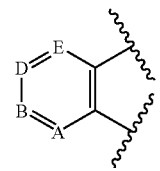

(II)

(wherein A=B means NR$^a$ (wherein R$^a$ means a hydrogen atom, a carboxyl group, a carbamoyl group, a sulfamoyl group, a thiol group, a phosphono group, a sulfo group, a tetrazole group, a formyl group, a nitro group, a cyano group, a halogen atom, a C$_{1-3}$ alkyl group, a C$_{1-3}$ alkoxy group (the C$_{1-3}$ alkyl group and the C$_{1-3}$ alkoxy group are optionally substituted with one or more halogen atoms), a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, a C$_{1-10}$ alkylaminocarbonyl group, a C$_{1-10}$ alkylsulfonyl group, a C$_{1-10}$ alkylsulfonylamino group, a C$_{1-10}$ alkylaminosulfonyl group, an amino group, a C$_{1-10}$ mono- or di-alkylamino group, a hydroxyl group, a protected hydroxyl group, a C$_{1-10}$ alkyl group, a C$_{2-6}$ alkenyl group, a C$_{2-6}$ alkynyl group (the C$_{1-10}$ alkoxy group, the C$_{1-10}$ alkylcarbonyl group, the C$_{1-10}$ alkylcarbonyloxy group, the C$_{1-10}$ alkoxycarbonyl group, the C$_{1-10}$ alkylcarbonylamino group, the C$_{1-10}$ alkylaminocarbonyl group, the C$_{1-10}$ alkylsulfonyl group, the C$_{1-10}$ alkylsulfonylamino group, the C$_{1-10}$ alkylaminosulfonyl group, the amino group, the C$_{1-10}$ mono- or di-alkylamino group, the hydroxyl group, the protected hydroxyl group, the C$_{1-10}$ alkyl group, the C$_{2-6}$ alkenyl group and the C$_{2-6}$ alkynyl group may optionally be substituted with one or more substituents each of which is independently represented by —V$^{15}$ (wherein V$^{15}$ is the same as V$^1$, and V$^1$ is the same as defined above)), a C$_{2-14}$ aryl group, a C$_{2-14}$ aryloxy group or a C$_{2-9}$ heterocyclyl group (the C$_{2-14}$ aryl group, the C$_{2-14}$ aryloxy group and the C$_{2-9}$ heterocyclyl group may be substituted with one or more substituents each of which is independently represented by —V$^{16}$ (wherein V$^{16}$ is the same as V$^2$, and V$^2$ is the same as defined above))), and a C$_{2-14}$ aryl group (the C$_{2-14}$ aryl group may be substituted with one or more substituents each of which is independently represented by —V$^e$ (wherein V$^e$ is the same as V$^2$, and V$^2$ is the same as defined above)) is fused at D and E), a tautomer, prodrug or pharmaceutically acceptable salt of the compound or a solvate thereof.

7. The compound according to 3, wherein R$^c$ is a hydrogen atom, a carboxyl group, a carbamoyl group, a sulfamoyl group, a thiol group, a phosphono group, a sulfo group, a tetrazole group, a formyl group, a nitro group, a cyano group, a halogen atom, a C$_{1-3}$ alkyl group, a C$_{1-3}$ alkoxy group (the C$_{1-3}$ alkyl group and the C$_{1-3}$ alkoxy group are optionally substituted with one or more halogen atoms), a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, a C$_{1-10}$ alkylaminocarbonyl group, a C$_{1-10}$ alkylsulfonyl group, a C$_{1-10}$ alkylsulfonylamino group, a C$_{1-10}$ alkylaminosulfonyl group, an amino group, a C$_{1-10}$ mono- or di-alkylamino group, a hydroxyl group, a protected hydroxyl group, a C$_{1-10}$ alkyl group, a C$_{2-6}$ alkenyl group or a C$_{2-6}$ alkynyl group (the C$_{1-10}$ alkoxy group, the C$_{1-10}$ alkylcarbonyl group, the C$_{1-10}$ alkylcarbonyloxy group, the C$_{1-10}$ alkoxycarbonyl group, the C$_{1-10}$ alkylcarbonylamino group, the C$_{1-10}$ alkylaminocarbonyl group, the C$_{1-10}$ alkylsulfonyl group, the C$_{1-10}$ alkylsulfonylamino group, the C$_{1-10}$ alkylaminosulfonyl group, the amino group, the C$_{1-10}$ mono- or di-alkylamino group, the hydroxyl group, the protected hydroxyl group, the $C_{1-10}$ alkyl group, the $C_{2-6}$ alkenyl group and the $C_{2-6}$ alkynyl group may optionally be substituted with one or more substituents each of which is independently represented by —$V^{15}$ (wherein $V^{15}$ is the same as $V^1$, and $V^1$ is the same as defined above)), a tautomer, prodrug or pharmaceutically acceptable salt of the compound or a solvate thereof.

8. The compound according to any one of 2 to 7, wherein $R^a$ is a $C_{2-14}$ aryl group, a $C_{2-14}$ aryloxy group or a $C_{2-9}$ heterocyclyl group (the $C_{2-14}$ aryl group, the $C_{2-14}$ aryloxy group and the $C_{2-9}$ heterocyclyl group may be substituted with one or more substituents each of which is independently represented by —$V^{16}$ (wherein $V^{16}$ is the same as $V^2$, and $V^2$ is the same as defined above)), a tautomer, prodrug or pharmaceutically acceptable salt of the compound or a solvate thereof.

9. The compound according to 2, 3, 4, 5, 7 or 8, wherein $R^b$ is a hydrogen atom, a carboxyl group, a carbamoyl group, a sulfamoyl group, a thiol group, a phosphono group, a sulfo group, a tetrazole group, a formyl group, a nitro group, a cyano group, a halogen atom, a $C_{1-3}$ alkyl group, a $C_{1-3}$ alkoxy group (the $C_{1-3}$ alkyl group and the $C_{1-3}$ alkoxy group are optionally substituted with one or more halogen atoms), a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, a $C_{1-10}$ alkylaminocarbonyl group, a $C_{1-10}$ alkylsulfonyl group, a $C_{1-10}$ alkylsulfonylamino group, a $C_{1-10}$ alkylaminosulfonyl group, an amino group, a $C_{1-10}$ mono- or di-alkylamino group, a hydroxyl group, a protected hydroxyl group, a $C_{1-10}$ alkyl group, a $C_{2-6}$ alkenyl group or a $C_{2-6}$ alkynyl group (the $C_{1-10}$ alkoxy group, the $C_{1-10}$ alkylcarbonyl group, the $C_{1-10}$ alkylcarbonyloxy group, the $C_{1-10}$ alkoxycarbonyl group, the $C_{1-10}$ alkylcarbonylamino group, the $C_{1-10}$ alkylaminocarbonyl group, the $C_{1-10}$ alkylsulfonyl group, the $C_{1-10}$ alkylsulfonylamino group, the $C_{1-10}$ alkylaminosulfonyl group, the amino group, the $C_{1-10}$ mono- or di-alkylamino group, the hydroxyl group, the protected hydroxyl group, the $C_{1-10}$ alkyl group, the $C_{2-6}$ alkenyl group and the $C_{2-6}$ alkynyl group may optionally be substituted with one or more substituents each of which is independently represented by —$V^{15}$ (wherein $V^{15}$ is the same as $V^1$, and $V^1$ is the same as defined above)), a tautomer, prodrug or pharmaceutically acceptable salt of the compound or a solvate thereof.

10. The compound according to any one of 1 to 9, wherein $L^2$ is a single bond, a tautomer, prodrug or pharmaceutically acceptable salt of the compound or a solvate thereof.

11. The compound according to any one of 1 to 10, wherein $L^3$ is a single bond, a tautomer, prodrug or pharmaceutically acceptable salt of the compound or a solvate thereof.

12. The compound according to any one of 1 to 10, wherein $L^3$ is $NR^{15}$ (wherein $R^{15}$ means a hydrogen atom, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group, a $C_{1-10}$ alkoxycarbonyl group, a $C_{1-10}$ alkylaminocarbonyl group, a $C_{1-10}$ alkylsulfonyl group or a $C_{1-10}$ alkylaminosulfonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyl group, the $C_{1-10}$ alkoxycarbonyl group, the $C_{1-10}$ alkylaminocarbonyl group, the $C_{1-10}$ alkylsulfonyl group and the $C_{1-10}$ alkylaminosulfonyl group may optionally be substituted with one or more carboxyl groups, one or more carbamoyl groups, one or more sulfamoyl groups, one or more formyl groups, one or more nitro groups, one or more cyano groups, one or more halogen atoms, one or more hydroxyl groups, one or more protected hydroxyl groups, one or more amino groups, one or more protected amino groups or one or more $C_{1-10}$ mono- or di-alkylamino groups)), a tautomer, prodrug or pharmaceutically acceptable salt of the compound or a solvate thereof.

13. The compound according to any one of 1 to 10, wherein $L^3$ is NH, a tautomer, prodrug or pharmaceutically acceptable salt of the compound or a solvate thereof.

14. The compound according to any one of 1 to 13, wherein $R^1$ is a hydrogen atom, a formyl group or a $C_{1-10}$ alkyl group (the $C_{1-10}$ alkyl group may optionally be substituted with one or more halogen atoms), a tautomer, prodrug or pharmaceutically acceptable salt of the compound or a solvate thereof.

15. The compound according to any one of 1 to 14, wherein $R^2$ is a hydrogen atom, a formyl group or a $C_{1-10}$ alkyl group (the $C_{1-10}$ alkyl group may optionally be substituted with one or more halogen atoms), a tautomer, prodrug or pharmaceutically acceptable salt of the compound or a solvate thereof.

16. The compound according to any one of 1 to 15, wherein X is $OR^{16}$ (wherein $R^{16}$ means a hydrogen atom, a $C_{1-10}$ alkyl group, a $C_{2-6}$ alkenyl group, a $C_{2-6}$ alkynyl group or a $C_{1-10}$ alkylcarbonyl group (the $C_{1-10}$ alkyl group, the $C_{2-6}$ alkenyl group, the $C_{2-6}$ alkynyl group and the $C_{1-10}$ alkylcarbonyl group may optionally be substituted with one or more substituents each of which is independently represented by —$V^{17}$ (wherein $V^{17}$ is the same as $V^1$, and $V^1$ is the same as defined above))), a tautomer, prodrug or pharmaceutically acceptable salt of the compound or a solvate thereof.

17. The compound according to any one of 1 to 15, wherein X is OH, a tautomer, prodrug or pharmaceutically acceptable salt of the compound or a solvate thereof.

18. The compound according to any one of 1 to 15, wherein X is $SR^{16}$ (wherein $R^{16}$ means a hydrogen atom, a $C_{1-10}$ alkyl group, a $C_{2-6}$ alkenyl group, a $C_{2-6}$ alkynyl group or a $C_{1-10}$ alkylcarbonyl group (the $C_{1-10}$ alkyl group, the $C_{2-6}$ alkenyl group, the $C_{2-6}$ alkynyl group and the $C_{1-10}$ alkylcarbonyl group may optionally be substituted with one or more substituents each of which is independently represented by —$V^{17}$ (wherein $V^{17}$ is the same as $V^1$, and $V^1$ is the same as defined above))), a tautomer, prodrug or pharmaceutically acceptable salt of the compound or a solvate thereof.

19. The compound according to any one of 1 to 15, wherein X is SH, a tautomer, prodrug or pharmaceutically acceptable salt of the compound or a solvate thereof.

20. The compound according to any one of 1 to 15, wherein X is $NR^{17}R^{18}$ (wherein each of $R^{17}$ and $R^{18}$ independently means a hydrogen atom, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group and the $C_{1-10}$ alkylcarbonyl group may optionally be substituted with one or more substituents each of which is independently represented by —$V^{18}$ (wherein $V^{18}$ is the same as $V^1$, and $V^1$ is the same as defined above)), a $C_{2-14}$ aryl group or a $C_{2-9}$ heterocyclyl group (the $C_{2-14}$ aryl group and the $C_{2-9}$ heterocyclyl group may optionally be substituted with one or more substituents each of which is independently represented by —$V^{19}$ (wherein $V^{19}$ is the same as $V^2$, and $V^2$ is the same as defined above))), a tautomer, prodrug or pharmaceutically acceptable salt of the compound or a solvate thereof.

21. The compound according to any one of 1 to 15, wherein X is $COR^{19}$ (wherein $R^{19}$ means a hydrogen atom, a hydroxyl group, a protected hydroxyl group, an amino group, a protected amino group, a $C_{1-10}$ alkyl group, a $C_{2-6}$ alkenyl group, a $C_{2-6}$ alkynyl group, a $C_{1-3}$ alkyl group, a $C_{1-3}$ alkoxy group (the $C_{1-3}$ alkyl group and the $C_{1-3}$ alkoxy group are optionally substituted with one or more halogen atoms), a $C_{1-10}$ alkoxy group, a $C_{1-10}$ mono- or di-alkylamino group, a $C_{2-14}$ aryl group, a $C_{2-14}$ aryloxy group or a $C_{2-9}$ heterocyclyl group (the $C_{1-10}$ alkoxy group, the $C_{1-10}$ mono- or di-alkylamino group, the $C_{2-14}$ aryl group, the $C_{2-14}$ aryloxy group and the $C_{2-9}$ heterocyclyl group may optionally be substituted with one or more substituents each of which is independently represented by —$V^{21}$ (wherein $V^{21}$ is the same as $V^1$, and $V^1$ is the same as defined above))), a tautomer, prodrug or pharmaceutically acceptable salt of the compound or a solvate thereof.

22. The compound according to any one of 1 to 15, wherein X is $SO_2R^{20}$ (wherein $R^{20}$ means a hydrogen atom, a hydroxyl group, a protected hydroxyl group, an amino group, a protected amino group, a $C_{1-10}$ alkyl group, a $C_{2-6}$ alkenyl group, a $C_{2-6}$ alkynyl group, a $C_{1-3}$ alkyl group, a $C_{1-3}$ alkoxy group (the $C_{1-3}$ alkyl group and the $C_{1-3}$ alkoxy group are optionally substituted with one or more halogen atoms), a $C_{1-10}$ alkoxy group, a $C_{1-10}$ mono- or di-alkylamino group, a $C_{2-14}$ aryl group, a $C_{2-14}$ aryloxy group or a $C_{2-9}$ heterocyclyl group (the $C_{1-10}$ alkoxy group, the $C_{1-10}$ mono- or di-alkylamino group, the $C_{2-14}$ aryl group, the $C_{2-14}$ aryloxy group and the $C_{2-9}$ heterocyclyl group may optionally be substituted with one or more substituents each of which is independently represented by —$V^{21}$ (wherein $V^{21}$ is the same as $V^1$, and $V^1$ is the same as defined above))), a tautomer, prodrug or pharmaceutically acceptable salt of the compound or a solvate thereof.

23. The compound according to any one of 1 to 22, wherein Y is an oxygen atom, a tautomer, prodrug or pharmaceutically acceptable salt of the compound or a solvate thereof.

24. The compound according to any one of 1 to 22, wherein Y is a sulfur atom, a tautomer, prodrug or pharmaceutically acceptable salt of the compound or a solvate thereof.

25. The compound according to any one of 1 to 22, wherein Y is $NR^{21}$ (wherein $R^{21}$ means a hydrogen atom, a formyl group, a hydroxyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, a $C_{1-10}$ alkylaminocarbonyl group, a $C_{1-10}$ alkylsulfonyl group, a $C_{1-10}$ alkylsulfonylamino group, a $C_{1-10}$ alkylaminosulfonyl group, a $C_{1-10}$ mono- or di-alkylamino group, a $C_{2-14}$ aryl group, a $C_{2-14}$ aryloxy group or a $C_{2-9}$ heterocyclyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyl group, the $C_{1-10}$ alkylcarbonyloxy group, the $C_{1-10}$ alkoxycarbonyl group, the $C_{1-10}$ alkylcarbonylamino group, the $C_{1-10}$ alkylaminocarbonyl group, the $C_{1-10}$ alkylsulfonyl group, the $C_{1-10}$ alkylsulfonylamino group, the $C_{1-10}$ alkylaminosulfonyl group, the $C_{1-10}$ mono- or di-alkylamino group, the $C_{2-14}$ aryl group, the $C_{2-14}$ aryloxy group and the $C_{2-9}$ heterocyclyl group may optionally be substituted with one or more substituents each of which is independently represented by —$V^{22}$ (wherein $V^{22}$ is the same as $V^1$, and $V^1$ is the same as defined above))), a tautomer, prodrug or pharmaceutically acceptable salt of the compound or a solvate thereof.

26. The compound according to any of 23 to 25, wherein $R^3$ is a $C_{2-9}$ nitrogen-containing heterocyclyl group (the $C_{2-9}$ nitrogen-containing heterocyclyl group may optionally be substituted with one or more substituents each of which is independently represented by —$V^a$ (wherein $V^a$ is the same as $V^5$, and $V^5$ is the same as defined above)), a tautomer, prodrug or pharmaceutically acceptable salt of the compound or a solvate thereof.

27. The compound according to any of 23 to 25, wherein $R^3$ is a $C_{2-9}$ nitrogen-containing heterocyclyl group (the $C_{2-9}$ nitrogen-containing heterocyclyl group may optionally be substituted with one or more substituents each of which is independently represented by —$V^b$ (wherein $V^b$ is the same as $W^4$, and $W^4$ is the same as defined above)), a tautomer, prodrug or pharmaceutically acceptable salt of the compound or a solvate thereof.

28. The compound according to any of 23 to 25, wherein $R^3$ is a $C_{2-9}$ nitrogen-containing heterocyclyl group (the $C_{2-9}$ nitrogen-containing heterocyclyl group may optionally be substituted with one or more substituents each of which is independently represented by —$V^c$ (wherein $V^c$ means a hydrogen atom, a hydroxyl group, a protected hydroxyl group, a thiol group, a protected thiol group, an amino group, a protected amino group, a formyl group, a nitro group, a cyano group, a halogen atom, a tetrazole group, a phosphono group, —$COCOR^7$, —$CH_2COR^7$, —$SO_2R^7$, —$SOR^7$ or —$COR^7$ (wherein $R^7$ means a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may optionally be substituted with one or more substituents each of which is independently represented by —$V^8$ (wherein $V^8$ is the same as $V^1$, and $V^1$ is the same as defined above)), a $C_{2-14}$ aryl group, a $C_{2-14}$ aryloxy group, a $C_{2-9}$ heterocyclyl group (the $C_{2-14}$ aryl group, the $C_{2-14}$ aryloxy group and the $C_{2-9}$ heterocyclyl group may optionally be substituted with one or more substituents each of which is independently represented by —$V^9$ (wherein $V^9$ is the same as $V^2$, and $V^2$ is the same as defined above)) or $NR^8R^9$ (wherein each of $R^8$ and $R^9$ independently means a hydrogen atom, a hydroxyl group, a formyl group, a carbamoyl group, a sulfamoyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, a $C_{1-10}$ alkylaminocarbonyl group, a $C_{1-10}$ alkylsulfonyl group, a $C_{1-10}$ alkylaminosulfonyl group, a $C_{1-10}$ mono- or di-alkylamino group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyl group, the $C_{1-10}$ alkylcarbonyloxy group, the $C_{1-10}$ alkoxycarbonyl group, the $C_{1-10}$ alkylcarbonylamino group, the $C_{1-10}$ alkylaminocarbonyl group, the $C_{1-10}$ alkylsulfonyl group, the $C_{1-10}$ alkylaminosulfonyl group and the $C_{1-10}$ mono- or di-alkylamino group may optionally be substituted with one or more substituents each of which is independently represented by —$V^{10}$ (wherein $V^{10}$ is the same as $V^1$, and $V^1$ is the same as defined above)), a $C_{2-14}$ aryl group or a $C_{2-9}$ heterocyclyl group (the $C_{2-14}$ aryl group and the $C_{2-9}$ heterocyclyl group may optionally be substituted with one or more substituents each of which is independently represented by —$V^{11}$ (wherein $V^{11}$ is the same as $V^2$, and $V^2$ is the same as defined above)))))), a tautomer, prodrug or pharmaceutically acceptable salt of the compound or a solvate thereof.

29. The compound according to any of 23 to 25, wherein $R^3$ is a $C_{2-9}$ nitrogen-containing heterocyclyl group (the $C_{2-9}$ nitrogen-containing heterocyclyl group is optionally substituted with one or more substituents each of which is independently represented by —$V^d$ (wherein $V^d$ means a hydrogen atom, a hydroxyl group, a protected hydroxyl group, a thiol group, a protected thiol group, an amino group, a protected amino group, a formyl group, a nitro group, a cyano group, a halogen atom, a tetrazole group, a phosphono group, —$COCOR^{22}$, —$CH_2COR^{22}$, —$SO_2R^{22}$, —$SOR^{22}$ or —$COR^{22}$ (wherein $R^{22}$ means a hydroxyl group or $NR^{23}R^{24}$ (wherein each of $R^{23}$ and $R^{24}$ is independently the same as $R^8$ or $R^9$, and $R^8$ and $R^9$ are the same as defined above)))), a tautomer, prodrug or pharmaceutically acceptable salt of the compound or a solvate thereof.

30. The compound according to any of 23 to 25, wherein $R^3$ is a $C_{2-9}$ nitrogen-containing heterocyclyl group (the $C_{2-9}$ nitrogen-containing heterocyclyl group is optionally substituted with one or more hydrogen atoms, one or more hydroxyl groups, one or more tetrazole groups, one or more carboxyl groups, one or more carbamoyl groups, one or more sulfamoyl groups, one or more —COCO$_2$H, one or more —CH$_2$CO$_2$H or one or more sulfo groups), a tautomer, prodrug or pharmaceutically acceptable salt of the compound or a solvate thereof.

31. The compound according to any of 23 to 25, wherein R$^3$ is represented by any of the formula (III):

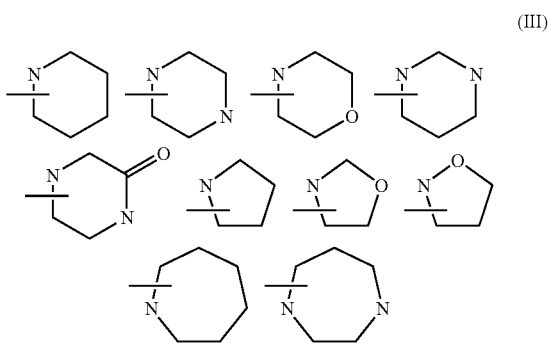

(III)

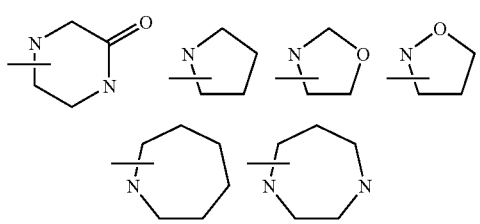

(wherein the formula (III) may optionally be substituted with one or more substituents each of which is independently represented by —V$^a$ (wherein V$^a$ is the same as V$^5$, and V$^5$ is the same as defined above)), a tautomer, prodrug or pharmaceutically acceptable salt of the compound or a solvate thereof.

32. The compound according to any of 23 to 25, wherein R$^3$ is represented by any of the formula (III):

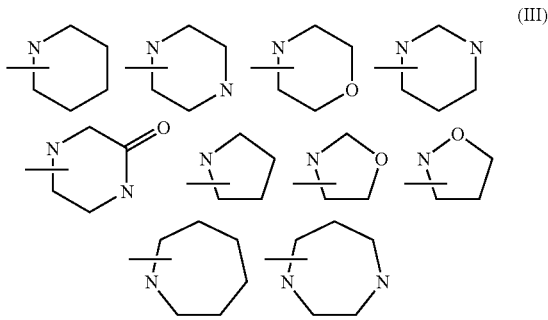

(III)

(wherein the formula (III) may optionally be substituted with one or more substituents each of which is independently represented by —V$^b$ (wherein V$^b$ is the same as W$^4$, and W$^4$ is the same as defined above)), a tautomer, prodrug or pharmaceutically acceptable salt of the compound or a solvate thereof.

33. The compound according to any of 23 to 25, wherein R$^3$ is represented by any of the formula (III):

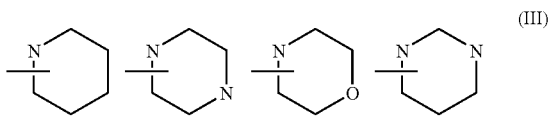

(III)

(wherein the formula (III) may optionally be substituted with one or more substituents each of which is independently represented by —V$^c$ (wherein V$^c$ is a hydrogen atom, a hydroxyl group, a protected hydroxyl group, a thiol group, a protected thiol group, an amino group, a protected amino group, a formyl group, a nitro group, a cyano group, a halogen atom, a tetrazole group, a phosphono group, —COCOR$^7$, —CH$_2$COR$^7$, —SO$_2$R$^7$, —SOR$^7$ or —COR$^7$ (wherein R$^7$ means a hydroxyl group, a C$_{1-10}$ alkyl group, a C$_{2-6}$ alkenyl group, a C$_{2-6}$ alkynyl group, a C$_{1-10}$ alkoxy group (the C$_{1-10}$ alkyl group, the C$_{2-6}$ alkenyl group, the C$_{2-6}$ alkynyl group and the C$_{1-10}$ alkoxy group may optionally be substituted with one or more substituents each of which is independently represented by —V$^8$ (wherein V$^8$ is the same as V$^1$, and V$^1$ is the same as defined above)), a C$_{2-14}$ aryl group, a C$_{2-14}$ aryloxy group, a C$_{2-9}$ heterocyclyl group (the C$_{2-14}$ aryl group, the C$_{2-14}$ aryloxy group and the C$_{2-9}$ heterocyclyl group may optionally be substituted with one or more substituents each of which is independently represented by —V$^9$ (wherein V$^9$ is the same as V$^2$, and V$^2$ is the same as defined above)) or NR$^8$R$^9$ (wherein each of R$^8$ and R$^9$ independently means a hydrogen atom, a hydroxyl group, a formyl group, a carbamoyl group, a sulfamoyl group, a C$_{1-10}$ alkyl group, a C$_{2-6}$ alkenyl group, a C$_{2-6}$ alkynyl group, a C$_{1-10}$ alkoxy group, a C$_{1-10}$ alkylcarbonyl group, a C$_{1-10}$ alkylcarbonyloxy group, a C$_{1-10}$ alkoxycarbonyl group, a C$_{1-10}$ alkylcarbonylamino group, a C$_{1-10}$ alkylaminocarbonyl group, a C$_{1-10}$ alkylsulfonyl group, a C$_{1-10}$ alkylaminosulfonyl group, a C$_{1-10}$ mono- or di-alkylamino group (the C$_{1-10}$ alkyl group, the C$_{2-6}$ alkenyl group, the C$_{2-6}$ alkynyl group, the C$_{1-10}$ alkoxy group, the C$_{1-10}$ alkylcarbonyl group, the C$_{1-10}$ alkylcarbonyloxy group, the C$_{1-10}$ alkoxycarbonyl group, the C$_{1-10}$ alkylcarbonylamino group, the C$_{1-10}$ alkylaminocarbonyl group, the C$_{1-10}$ alkylsulfonyl group, the C$_{1-10}$ alkylaminosulfonyl group and the C$_{1-10}$ mono- or di-alkylamino group may optionally be substituted with one or more substituents each of which is independently represented by —V$^{10}$ (wherein V$^{10}$ is the same as V$^1$, and V$^1$ is the same as defined above)), a C$_{2-14}$ aryl group or a C$_{2-9}$ heterocyclyl group (the C$_{2-14}$ aryl group and the C$_{2-9}$ heterocyclyl group may optionally be substituted with one or more substituents each of which is independently represented by —V$^{11}$ (wherein V$^{11}$ is the same as V$^2$, and V$^2$ is the same as defined above)))))), a tautomer, prodrug or pharmaceutically acceptable salt of the compound or a solvate thereof.

34. The compound according to any of 23 to 25, wherein R$^3$ is represented by any of the formula (III):

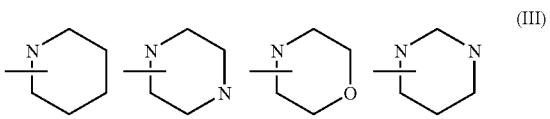

(III)

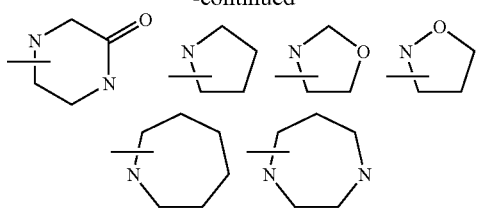

(wherein the formula (III) may optionally be substituted with one or more substituents each of which is independently represented by —$V^d$ (wherein $V^d$ means a hydrogen atom, a hydroxyl group, a protected hydroxyl group, a thiol group, a protected thiol group, an amino group, a protected amino group, a formyl group, a nitro group, a cyano group, a halogen atom, a tetrazole group, a phosphono group, —$COCOR^{22}$, —$CH_2COR^{22}$, —$SO_2R^{22}$, —$SOR^{22}$ or —$COR^{22}$ (wherein $R^{22}$ means a hydroxyl group or $NR^{23}R^{24}$ (wherein each of $R^{23}$ and $R^{24}$ is independently the same as $R^8$ or $R^9$, and $R^8$ and $R^9$ are the same as defined above)))), a tautomer, prodrug or pharmaceutically acceptable salt of the compound or a solvate thereof.

35. The compound according to any of 23 to 25, wherein $R^3$ is represented by any of the formula (III):

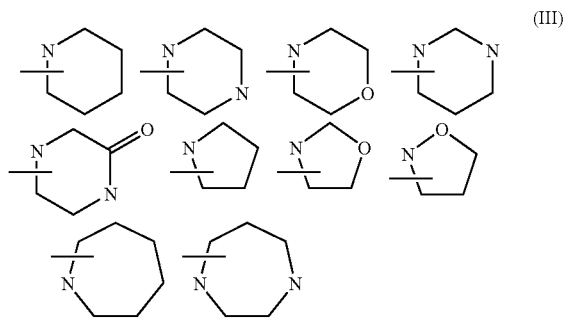

(wherein the formula (III) is optionally substituted with a hydrogen atom, a hydroxyl group, a tetrazole group, a carboxyl group, a carbamoyl group, a sulfamoyl group, —$COCO_2H$, —$CH_2CO_2H$ or a sulfo group), a tautomer, prodrug or pharmaceutically acceptable salt of the compound or a solvate thereof.

36. A thrombopoietin receptor activator containing the compound according to any one of 1 to 35, a tautomer, prodrug or pharmaceutically acceptable salt of the compound or a solvate thereof, as an active ingredient.

37. A preventive, therapeutic or improving agent for diseases against which activation of the thrombopoietin receptor is effective, which contains the thrombopoietin receptor activator according to 36, as an active ingredient.

38. A platelet increasing agent containing the thrombopoietin receptor activator according to 36, as an active ingredient.

39. Medicament containing the compound according to any one of 1 to 35, a tautomer, prodrug or pharmaceutically acceptable salt of the compound or a solvate thereof, as an active ingredient.

Effects of the Invention

The present invention provides pharmaceutical compositions containing compounds which can serve as platelet increasing agents or increasing agents for other blood cells by stimulating differentiation and proliferation of hematopoietic stem cells, megakaryocytic progenitor cells and megakaryocytes or compounds which can be used for therapeutic angiogenesis or show antiarteriosclerotic action by stimulating endothelial cells and endothelial progenitor cells.

BEST MODE FOR CARRYING OUT THE INVENTION

Now, the present invention will be described in detail.

In the present invention, "n" denotes normal, "i" denotes iso, "s" denotes secondary, "t" denotes tertiary, "c" denotes cyclo, "o" denotes ortho, "m" denotes meta, "p" denotes para, "Ph" denotes phenyl, "Me" denotes methyl, "Et" denotes ethyl, "Pr" denotes propyl, and "Bu" denotes butyl.

First, the terms in the respective substituents $R^1$ to $R^{31}$, $R^a$ to $R^c$, $V^1$ to $V^{22}$ and $V^a$ to $V^e$ will be explained.

As a halogen atom, a fluorine atom, a chlorine atom, a bromine atom or an iodine atom may be mentioned.

A $C_{1-3}$ alkyl group may be linear, branched or a $C_3$ cycloalkyl group, and methyl, ethyl, n-propyl, i-propyl and c-propyl and the like may be mentioned.

A $C_{1-6}$ alkyl group may be linear, branched or a $C_{3-6}$ cycloalkyl group, and, for example, in addition to those mentioned above, n-butyl, i-butyl, s-butyl, t-butyl, c-butyl, 1-methyl-c-propyl, 2-methyl-c-propyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, c-pentyl, 1-methyl-c-butyl, 2-methyl-c-butyl, 3-methyl-c-butyl, 1,2-dimethyl-c-propyl, 2,3-dimethyl-c-propyl, 1-ethyl-c-propyl, 2-ethyl-c-propyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, c-hexyl, 1-methyl-c-pentyl, 2-methyl-c-pentyl, 3-methyl-c-pentyl, 1-ethyl-c-butyl, 2-ethyl-c-butyl, 3-ethyl-c-butyl, 1,2-dimethyl-c-butyl, 1,3-dimethyl-c-butyl, 2,2-dimethyl-c-butyl, 2,3-dimethyl-c-butyl, 2,4-dimethyl-c-butyl, 3,3-dimethyl-c-butyl, 1-n-propyl-c-propyl, 2-n-propyl-c-propyl, 1-i-propyl-c-propyl, 2-i-propyl-c-propyl, 1,2,2-trimethyl-c-propyl, 1,2,3-trimethyl-c-propyl, 2,2,3-trimethyl-c-propyl, 1-ethyl-2-methyl-c-propyl, 2-ethyl-1-methyl-c-propyl, 2-ethyl-2-methyl-c-propyl, 2-ethyl-3-methyl-c-propyl and the like may be mentioned.

A $C_{1-10}$ alkyl group may be linear, branched or a $C_{3-10}$ cycloalkyl group, and, for example, in addition to those mentioned above, 1-methyl-1-ethyl-n-pentyl, 1-heptyl, 2-heptyl, 1-ethyl-1,2-dimethyl-n-propyl, 1-ethyl-2,2-dimethyl-n-propyl, 1-octyl, 3-octyl, 4-methyl-3-n-heptyl, 6-methyl-2-n-heptyl, 2-propyl-1-n-heptyl, 2,4,4-trimethyl-1-n-pentyl, 1-nonyl, 2-nonyl, 2,6-dimethyl-4-n-heptyl, 3-ethyl-2,2-dimethyl-3-n-pentyl, 3,5,5-trimethyl-1-n-hexyl, 1-decyl, 2-decyl, 4-decyl, 3,7-dimethyl-1-n-octyl, 3,7-dimethyl-3-n-octyl and the like may be mentioned.

As a $C_{2-6}$ alkynyl group, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl- 3-butynyl, 2,2-dimethyl-3-butynyl, 3,3-dimethyl-1-butynyl, 1-ethyl-2-butynyl, 1-ethyl-3-butynyl, 1-n-propyl-2-propynyl, 2-ethyl-3-butynyl, 1-methyl-1-ethyl-2-propynyl, 1-i-propyl-2-propynyl and the like may be mentioned.

A $C_{2-6}$ alkenyl group may be linear, branched or a $C_{3-6}$ cycloalkenyl group, and, for example, ethenyl, 1-propenyl, 2-propenyl, 1-methyl-1-ethenyl, 1-butenyl, 2-butenyl, 3-butenyl, 2-methyl-1-propenyl, 2-methyl-2-propenyl, 1-ethylethenyl, 1-methyl-1-propenyl, 1-methyl-2-propenyl, 1-pentenyl, 2-pentenyl, 3-pentenyl, 4-pentenyl, 1-n-propylethenyl, 1-methyl-1-butenyl, 1-methyl-2-butenyl, 1-methyl-3-butenyl, 2-ethyl-2-propenyl, 2-methyl-1-butenyl, 2-methyl-2-butenyl, 2-methyl-3-butenyl, 3-methyl-1-butenyl, 3-methyl-2-butenyl, 3-methyl-3-butenyl, 1,1-dimethyl-2-propenyl, 1-i-propylethenyl, 1,2-dimethyl-1-propenyl, 1,2-dimethyl-2-propenyl, 1-c-pentenyl, 2-c-pentenyl, 3-c-pentenyl, 1-hexenyl, 2-hexenyl, 3-hexenyl, 4-hexenyl, 5-hexenyl, 1-methyl-1-pentenyl, 1-methyl-2-pentenyl, 1-methyl-3-pentenyl, 1-methyl-4-pentenyl, 1-n-butylethenyl, 2-methyl-1-pentenyl, 2-methyl-2-pentenyl, 2-methyl-3-pentenyl, 2-methyl-4-pentenyl, 2-n-propyl-2-propenyl, 3-methyl-1-pentenyl, 3-methyl-2-pentenyl, 3-methyl-3-pentenyl, 3-methyl-4-pentenyl, 3-ethyl-3-butenyl, 4-methyl-1-pentenyl, 4-methyl-2-pentenyl, 4-methyl-3-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1-methyl-2-ethyl-2-propenyl, 1-s-butylethenyl, 1,3-dimethyl-1-butenyl, 1,3-dimethyl-2-butenyl, 1,3-dimethyl-3-butenyl, 1-i-butylethenyl, 2,2-dimethyl-3-butenyl, 2,3-dimethyl-1-butenyl, 2,3-dimethyl-2-butenyl, 2,3-dimethyl-3-butenyl, 2-i-propyl-2-propenyl, 3,3-dimethyl-1-butenyl, 1-ethyl-1-butenyl, 1-ethyl-2-butenyl, 1-ethyl-3-butenyl, 1-n-propyl-1-propenyl, 1-n-propyl-2-propenyl, 2-ethyl-1-butenyl, 2-ethyl-2-butenyl, 2-ethyl-3-butenyl, 1,1,2-trimethyl-2-propenyl, 1-t-butylethenyl, 1-methyl-1-ethyl-2-propenyl, 1-ethyl-2-methyl-1-propenyl, 1-ethyl-2-methyl-2-propenyl, 1-i-propyl-1-propenyl, 1-i-propyl-2-propenyl, 1-methyl-2-c-pentenyl, 1-methyl-3-c-pentenyl, 2-methyl-1-c-pentenyl, 2-methyl-2-c-pentenyl, 2-methyl-3-c-pentenyl, 2-methyl-4-c-pentenyl, 2-methyl-5-c-pentenyl, 2-methylene-c-pentyl, 3-methyl-1-c-pentenyl, 3-methyl-2-c-pentenyl, 3-methyl-3-c-pentenyl, 3-methyl-4-c-pentenyl, 3-methyl-5-c-pentenyl, 3-methylene-c-pentyl, 1-c-hexenyl, 2-c-hexenyl, 3-c-hexenyl and the like may be mentioned.

A $C_{1-6}$ alkylcarbonyl group may linear, branched or a $C_{3-6}$ cycloalkylcarbonyl group, and, for example, methylcarbonyl, ethylcarbonyl, n-propylcarbonyl, i-propylcarbonyl, c-propylcarbonyl, n-butylcarbonyl, i-butylcarbonyl, s-butylcarbonyl, t-butylcarbonyl, c-butylcarbonyl, 1-methyl-c-propylcarbonyl, 2-methyl-c-propylcarbonyl, n-pentylcarbonyl, 1-methyl-n-butylcarbonyl, 2-methyl-n-butylcarbonyl, 3-methyl-n-butylcarbonyl, 1,1-dimethyl-n-propylcarbonyl, 1,2-dimethyl-n-propylcarbonyl, 2,2-dimethyl-n-propylcarbonyl, 1-ethyl-n-propylcarbonyl, c-pentylcarbonyl, 1-methyl-c-butylcarbonyl, 2-methyl-c-butylcarbonyl, 3-methyl-c-butylcarbonyl, 1,2-dimethyl-c-propylcarbonyl, 2,3-dimethyl-c-propylcarbonyl, 1-ethyl-c-propylcarbonyl, 2-ethyl-c-propylcarbonyl, n-hexylcarbonyl, 1-methyl-n-pentylcarbonyl, 2-methyl-n-pentylcarbonyl, 3-methyl-n-pentylcarbonyl, 4-methyl-n-pentylcarbonyl, 1,1-dimethyl-n-butylcarbonyl, 1,2-dimethyl-n-butylcarbonyl, 1,3-dimethyl-n-butylcarbonyl, 2,2-dimethyl-n-butylcarbonyl, 2,3-dimethyl-n-butylcarbonyl, 3,3-dimethyl-n-butylcarbonyl, 1-ethyl-n-butylcarbonyl, 2-ethyl-n-butylcarbonyl, 1,1,2-trimethyl-n-propylcarbonyl, 1,2,2-trimethyl-n-propylcarbonyl, 1-ethyl-1-methyl-n-propylcarbonyl, 1-ethyl-n-propylcarbonyl, c-hexylcarbonyl, 1-methyl-c-pentylcarbonyl, 2-methyl-c-pentylcarbonyl, 3-methyl-c-pentylcarbonyl, 1-ethyl-c-butylcarbonyl, 2-ethyl-c-butylcarbonyl, 3-ethyl-c-butylcarbonyl, 1,2-dimethyl-c-butylcarbonyl, 1,3-dimethyl-c-butylcarbonyl, 2,2-dimethyl-c-butylcarbonyl, 2,3-dimethyl-c-butylcarbonyl, 2,4-dimethyl-c-butylcarbonyl, 3,3-dimethyl-c-butylcarbonyl, 1-n-propyl-c-propylcarbonyl, 2-n-propyl-c-propylcarbonyl, 1-i-propyl-c-propylcarbonyl, 2-i-propyl-c-propylcarbonyl, 1,2,2-trimethyl-c-propylcarbonyl, 1,2,3-trimethyl-c-propylcarbonyl, 2,2,3-trimethyl-c-propylcarbonyl, 1-ethyl-2-methyl-c-propylcarbonyl, 2-ethyl-1-methyl-c-propylcarbonyl, 2-ethyl-2-methyl-c-propylcarbonyl, 2-ethyl-3-methyl-c-propylcarbonyl or the like may be mentioned.

A $C_{1-10}$ alkylcarbonyl may be linear, branched or a $C_{3-10}$ cycloalkylcarbonyl group, and for example, in addition to those mentioned above, 1-methyl-1-ethyl-n-pentylcarbonyl, 1-heptylcarbonyl, 2-heptylcarbonyl, 1-ethyl-1,2-dimethyl-n-propylcarbonyl, 1-ethyl-2,2-dimethyl-n-propylcarbonyl, 1-octylcarbonyl, 3-octylcarbonyl, 4-methyl-3-n-heptylcarbonyl, 6-methyl-2-n-heptylcarbonyl, 2-propyl-1-n-heptylcarbonyl, 2,4,4-trimethyl-1-n-pentylcarbonyl, 1-nonylcarbonyl, 2-nonylcarbonyl, 2,6-dimethyl-4-n-heptylcarbonyl, 3-ethyl-2,2-dimethyl-3-n-pentylcarbonyl, 3,5,5-trimethyl-1-n-hexylcarbonyl, 1-decylcarbonyl, 2-decylcarbonyl, 4-decylcarbonyl, 3,7-dimethyl-1-n-octylcarbonyl, 3,7-dimethyl-3-n-octylcarbonyl or the like may be mentioned.

A $C_{1-3}$ alkoxy group may be linear, branched or a $C_3$ cycloalkoxy group, and methoxy, ethoxy, n-propoxy, i-propoxy, c-propoxy or the like may be mentioned.

A $C_{1-6}$ alkoxy group may be linear, branched or a $C_{3-6}$ cycloalkoxy group, and, for example, in addition to those mentioned above, n-butoxy, i-butoxy, s-butoxy, t-butoxy, c-butoxy, 1-methyl-c-propoxy, 2-methyl-c-propoxy, n-pentyloxy, 1-methyl-n-butoxy, 2-methyl-n-butoxy, 3-methyl-n-butoxy, 1,1-dimethyl-n-propoxy, 1,2-dimethyl-n-propoxy, 2,2-dimethyl-n-propoxy, 1-ethyl-n-propoxy, c-pentyloxy, 1-methyl-c-butoxy, 2-methyl-c-butoxy, 3-methyl-c-butoxy, 1,2-dimethyl-c-propoxy, 2,3-dimethyl-c-propoxy, 1-ethyl-c-propoxy, 2-ethyl-c-propoxy, n-hexyloxy, 1-methyl-n-pentyloxy, 2-methyl-n-pentyloxy, 3-methyl-n-pentyloxy, 4-methyl-n-pentyloxy, 1,1-dimethyl-n-butoxy, 1,2-dimethyl-n-butoxy, 1,3-dimethyl-n-butoxy, 2,2-dimethyl-n-butoxy, 2,3-dimethyl-n-butoxy, 3,3-dimethyl-n-butoxy, 1-ethyl-n-butoxy, 2-ethyl-n-butoxy, 1,1,2-trimethyl-n-propoxy, 1,2,2-trimethyl-n-propoxy, 1-ethyl-1-methyl-n-propoxy, 1-ethyl-2-methyl-n-propoxy, c-hexyloxy, 1-methyl-c-pentyloxy, 2-methyl-c-pentyloxy, 3-methyl-c-pentyloxy, 1-ethyl-c-butoxy, 2-ethyl-c-butoxy, 3-ethyl-c-butoxy, 1,2-dimethyl-c-butoxy, 1,3-dimethyl-c-butoxy, 2,2-dimethyl-c-butoxy, 2,3-dimethyl-c-butoxy, 2,4-dimethyl-c-butoxy, 3,3-dimethyl-c-butoxy, 1-n-propyl-c-propoxy, 2-n-propyl-c-propoxy, 1-i-propyl-c-propoxy, 2-i-propyl-c-propoxy, 1,2,2-trimethyl-c-propoxy, 1,2,3-trimethyl-c-propoxy, 2,2,3-trimethyl-c-propoxy, 1-ethyl-2-methyl-c-propoxy, 2-ethyl-1-methyl-c-propoxy, 2-ethyl-2-methyl-c-propoxy, 2-ethyl-3-methyl-c-propoxy or the like may be mentioned.

A $C_{1-10}$ alkoxy group may be linear, branched or a $C_{3-10}$ cycloalkoxy group, and, for example, in addition to those mentioned above, 1-methyl-1-ethyl-n-pentyloxy, 1-heptyloxy, 2-heptyloxy, 1-ethyl-1,2-dimethyl-n-propyloxy, 1-ethyl-2,2-dimethyl-n-propyloxy, 1-octyloxy, 3-octyloxy, 4-methyl-3-n-heptyloxy, 6-methyl-2-n-heptyloxy, 2-propyl-1-n-heptyloxy, 2,4,4-trimethyl-1-n-pentyloxy, 1-nonyloxy, 2-nonyloxy, 2,6-dimethyl-4-n-heptyloxy, 3-ethyl-2,2-dimethyl-3-n-pentyloxy, 3,5,5-trimethyl-1-n-hexyloxy, 1-decyloxy, 2-decyloxy, 4-decyloxy, 3,7-dimethyl-1-n-octyloxy, 3,7-dimethyl-3-n-octyloxy or the like may be mentioned.

A $C_{1-10}$ thioalkyl group may linear, branched or a $C_{3-10}$ cyclothioalkyl group, and methylthio, ethylthio, n-propylthio, i-propylthio, c-propylthio, n-butylthio, i-butylthio, s-butylthio, t-butylthio, c-butylthio, 1-methyl-c-propylthio, 2-methyl-c-propylthio, n-pentylthio, 1-methyl-n-butylthio, 2-methyl-n-butylthio, 3-methyl-n-butylthio, 1,1-dimethyl-n-propylthio, 1,2-dimethyl-n-propylthio, 2,2-dimethyl-n-propylthio, 1-ethyl-n-propylthio, c-pentylthio, 1-methyl-c-butylthio, 2-methyl-c-butylthio, 3-methyl-c-butylthio, 1,2-dimethyl-c-propylthio, 2,3-dimethyl-c-propylthio, 1-ethyl-c-propylthio, 2-ethyl-c-propylthio, n-hexylthio, 1-methyl-n-pentylthio, 2-methyl-n-pentylthio, 3-methyl-n-pentylthio, 4-methyl-n-pentylthio, 1,1-dimethyl-n-butylthio, 1,2-dimethyl-n-butylthio, 1,3-dimethyl-n-butylthio, 2,2-dimethyl-n-butylthio, 2,3-dimethyl-n-butylthio, 3,3-dimethyl-n-butylthio, 1-ethyl-n-butylthio, 2-ethyl-n-butylthio, 1,1,2-trimethyl-n-propylthio, 1,2,2-trimethyl-n-propylthio, 1-ethyl-1-methyl-n-propylthio, 1-ethyl-2-methyl-n-propylthio, c-hexylthio, 1-methyl-c-pentylthio, 2-methyl-c-pentylthio, 3-methyl-c-pentylthio, 1-ethyl-c-butylthio, 2-ethyl-c-butylthio, 3-ethyl-c-butylthio, 1,2-dimethyl-c-butylthio, 1,3-dimethyl-c-butylthio, 2,2-dimethyl-c-butylthio, 2,3-dimethyl-c-butylthio, 2,4-dimethyl-c-butylthio, 3,3-dimethyl-c-butylthio, 1-n-propyl-c-propylthio, 2-n-propyl-c-propylthio, 1-i-propyl-c-propylthio, 2-i-propyl-c-propylthio, 1,2,2-trimethyl-c-propylthio, 1,2,3-trimethyl-c-propylthio, 2,2,3-trimethyl-c-propylthio, 1-ethyl-2-methyl-c-propylthio, 2-ethyl-1-methyl-c-propylthio, 2-ethyl-2-methyl-c-propylthio, 2-ethyl-3-methyl-c-propylthio, 1-methyl-1-ethyl-n-pentylthio, 1-heptylthio, 2-heptylthio, 1-ethyl-1,2-dimethyl-n-propylthio, 1-ethyl-2,2-dimethyl-n-propylthio, 1-octylthio, 3-octylthio, 4-methyl-3-n-heptylthio, 6-methyl-2-n-heptylthio, 2-propyl-1-n-heptylthio, 2,4,4-trimethyl-1-n-pentylthio, 1-nonylthio, 2-nonylthio, 2,6-dimethyl-4-n-heptylthio, 3-ethyl-2,2-dimethyl-3-n-pentylthio, 3,5,5-trimethyl-1-n-hexylthio, 1-decylthio, 2-decylthio, 4-decylthio, 3,7-dimethyl-1-n-octylthio, 3,7-dimethyl-3-n-octylthio or the like may be mentioned.

A $C_{1-6}$ alkylsulfonylamino group may be linear, branched or a $C_{3-6}$ cycloalkylsulfonylamino group, and for example, methylsulfonylamino, ethylsulfonylamino, n-propylsulfonylamino, i-propylsulfonylamino, c-propylsulfonylamino, n-butylsulfonylamino, i-butylsulfonylamino, s-butylsulfonylamino, t-butylsulfonylamino, c-butylsulfonylamino, 1-methyl-c-propylsulfonylamino, 2-methyl-c-propylsulfonylamino, n-pentylsulfonylamino, 1-methyl-n-butylsulfonylamino, 2-methyl-n-butylsulfonylamino, 3-methyl-n-butylsulfonylamino, 1,1-dimethyl-n-propylsulfonylamino, 1,2-dimethyl-n-propylsulfonylamino, 2,2-dimethyl-n-propylsulfonylamino, 1-ethyl-n-propylsulfonylamino, c-pentylsulfonylamino, 1-methyl-c-butylsulfonylamino, 2-methyl-c-butylsulfonylamino, 3-methyl-c-butylsulfonylamino, 1,2-dimethyl-c-propylsulfonylamino, 2,3-dimethyl-c-propylsulfonylamino, 1-ethyl-c-propylsulfonylamino, 2-ethyl-c-propylsulfonylamino, n-hexylsulfonylamino, 1-methyl-n-pentylsulfonylamino, 2-methyl-n-pentylsulfonylamino, 3-methyl-n-pentylsulfonylamino, 4-methyl-n-pentylsulfonylamino, 1,1-dimethyl-n-butylsulfonylamino, 1,2-dimethyl-n-butylsulfonylamino, 1,3-dimethyl-n-butylsulfonylamino, 2,2-dimethyl-n-butylsulfonylamino, 2,3-dimethyl-n-butylsulfonylamino, 3,3-dimethyl-n-butylsulfonylamino, 1-ethyl-n-butylsulfonylamino, 2-ethyl-n-butylsulfonylamino, 1,1,2-trimethyl-n-propylsulfonylamino, 1,2,2-trimethyl-n-propylsulfonylamino, 1-ethyl-1-methyl-n-propylsulfonylamino, 1-ethyl-2-methyl-n-propylsulfonylamino, c-hexylsulfonylamino, 1-methyl-c-pentylsulfonylamino, 2-methyl-c-pentylsulfonylamino, 3-methyl-c-pentylsulfonylamino, 1-ethyl-c-butylsulfonylamino, 2-ethyl-c-butylsulfonylamino, 3-ethyl-c-butylsulfonylamino, 1,2-dimethyl-c-butylsulfonylamino, 1,3-dimethyl-c-butylsulfonylamino, 2,2-dimethyl-c-butylsulfonylamino, 2,3-dimethyl-c-butylsulfonylamino, 2,4-dimethyl-c-butylsulfonylamino, 3,3-dimethyl-c-butylsulfonylamino, 1-n-propyl-c-propylsulfonylamino, 2-n-propyl-c-propylsulfonylamino, 1-i-propyl-c-propylsulfonylamino, 2-i-propyl-c-propylsulfonylamino, 1,2,2-trimethyl-c-propylsulfonylamino, 1,2,3-trimethyl-c-propylsulfonylamino, 2,2,3-trimethyl-c-propylsulfonylamino, 1-ethyl-2-methyl-c-propylsulfonylamino, 2-ethyl-1-methyl-c-propylsulfonylamino, 2-ethyl-2-methyl-c-propylsulfonylamino, 2-ethyl-3-methyl-c-propylsulfonylamino or the like may be mentioned.

A $C_{1-10}$ alkylsulfonylamino group may be linear, branched or a $C_{3-10}$ cycloalkylsulfonylamino group, and for example, in addition to those mentioned above, 1-methyl-1-ethyl-n-pentylsulfonylamino, 1-heptylsulfonylamino, 2-heptylsulfonylamino, 1-ethyl-1,2-dimethyl-n-propylsulfonylamino, 1-ethyl-2,2-dimethyl-n-propylsulfonylamino, 1-octylsulfonylamino, 3-octylsulfonylamino, 4-methyl-3-n-heptylsulfonylamino, 2-propyl-1-n-n-heptylsulfonylamino, 6-methyl-2-n-heptylsulfonylamino, 2-propyl-1-n-n-heptylsulfonylamino, 2,4,4-trimethyl-1-n-pentylsulfonylamino, 1-nonylsulfonylamino, 2-nonylsulfonylamino, 2,6-dimethyl-4-n-heptylsulfonylamino, 3-ethyl-2,2-dimethyl-3-n-pentylsulfonylamino, 3,5,5-trimethyl-1-n-hexylsulfonylamino, 1-decylsulfonylamino, 2-decylsulfonylamino, 4-decylsulfonylamino, 3,7-dimethyl-1-n-octylsulfonylamino, 3,7-dimethyl-3-n-octylsulfonylamino, c-heptylsulfonylamino, c-octylsulfonylamino, 1-methyl-c-hexylsulfonylamino, 2-methyl-c-hexylsulfonylamino, 3-methyl-c-hexylsulfonylamino, 1,2-dimethyl-c-hexylsulfonylamino, 1-ethyl-c-hexylsulfonylamino, 1-methyl-c-pentylsulfonylamino, 2-methyl-c-pentylsulfonylamino, 3-methyl-c-pentylsulfonylamino or the like may be mentioned.

A $C_{1-6}$ alkoxycarbonyl group may be linear, branched or a $C_{3-6}$ cycloalkoxycarbonyl group, and for example, methoxycarbonyl, ethoxycarbonyl, n-propoxycarbonyl, i-propoxycarbonyl, c-propoxylcarbonyl, n-butoxycarbonyl, i-butoxycarbonyl, s-butoxycarbonyl, t-butoxycarbonyl, c-butoxycarbonyl, 1-methyl-c-propoxycarbonyl, 2-methyl-c-propoxycarbonyl, n-pentyloxycarbonyl, 1-methyl-n-butoxycarbonyl, 2-methyl-n-butoxycarbonyl, 3-methyl-n-butoxycarbonyl, 1,1-dimethyl-n-propoxycarbonyl, 1,2-dimethyl-n-propoxycarbonyl, 2,2-dimethyl-n-propoxycarbonyl, 1-ethyl-n-propoxycarbonyl, c-pentyloxycarbonyl, 1-methyl-c-butoxycarbonyl, 2-methyl-c-butoxycarbonyl, 3-methyl-c-butoxycarbonyl, 1,2-dimethyl-c-propoxycarbonyl, 2,3-dimethyl-c-propoxycarbonyl, 1-ethyl-c-propoxycarbonyl, 2-ethyl-c-propoxycarbonyl, n-hexyloxycarbonyl, 1-methyl-n-pentyloxycarbonyl, 2-methyl-n-pentyloxycarbonyl, 3-methyl-n-pentyloxycarbonyl, 4-methyl-n-pentyloxycarbonyl, 1,1-dimethyl-n-butoxycarbonyl, 1,2-dimethyl-n-butoxycarbonyl, 1,3-dimethyl-n-butoxycarbonyl, 2,2-dimethyl-n-butoxycarbonyl, 2,3-dimethyl-n-butoxycarbonyl, 3,3-dimethyl-n-butoxycarbonyl, 1-ethyl-n-butoxycarbonyl, 2-ethyl-n-butoxycarbonyl, 1,1,2-trimethyl-n-propoxycarbonyl, 1,2,2-trimethyl-n-propoxycarbonyl, 1-ethyl-1-methyl-n-propoxycarbonyl, 1-ethyl-2-methyl-n-propoxycarbonyl, c-hexyloxycarbonyl, 1-methyl-c-pentyloxycarbonyl, 2-methyl-c-pentyloxycarbonyl, 3-methyl-c-pentyloxycarbonyl, 1-ethyl-c-butoxycarbonyl, 2-ethyl-c-butoxycarbonyl, 3-ethyl-c-butoxycarbonyl, 1,2-dimethyl-c-butoxycarbonyl, 1,3-dimethyl-c-butoxycarbonyl, 2,2-dimethyl-c-butoxycarbonyl, 2,3-dimethyl-c-butoxycarbonyl, 2,4-dimethyl-c-butoxycarbonyl, 3,3-dimethyl-c-butoxycarbonyl, 1-n-propyl-c-propoxycarbonyl, 2-n-propyl-c-propoxycarbonyl, 1-i-propyl-c-propoxycarbonyl, 2-i-propyl-c-propoxycarbonyl, 1,2,2-trimethyl-c-propoxycarbonyl, 1,2,3-trimethyl-c-propoxycarbonyl, 2,2,3-trimethyl-c-propoxycarbonyl, 1-ethyl-2-methyl-c-propoxycarbonyl, 2-ethyl-1-methyl-c-propoxycarbonyl, 2-ethyl-2-methyl-c-propoxycarbonyl, 2-ethyl-3-methyl-c-propoxycarbonyl or the like may be mentioned.

A $C_{1-10}$ alkoxycarbonyl group may be linear, branched or a $C_{3-10}$ cycloalkoxycarbonyl group, and, for example, in addition to those mentioned above, 1-methyl-1-ethyl-n-pentyloxycarbonyl, 1-heptyloxycarbonyl, 2-heptyloxycarbonyl, 1-ethyl-1,2-dimethyl-n-propyloxycarbonyl, 1-ethyl-2,2-dimethyl-n-propyloxycarbonyl, 1-octyloxycarbonyl, 3-octyloxycarbonyl, 4-methyl-3-n-heptyloxycarbonyl, 6-methyl-2-n-heptyloxycarbonyl, 2-propyl-1-n-heptyloxycarbonyl, 2,4,4-trimethyl-1-n-pentyloxycarbonyl, 1-nonyloxycarbonyl, 2-nonyloxycarbonyl, 2,6-dimethyl-4-n-heptyloxycarbonyl, 3-ethyl-2,2-dimethyl-3-n-pentyloxycarbonyl, 3,5,5-trimethyl-1-n-hexyloxycarbonyl, 1-decyloxycarbonyl, 2-decyloxycarbonyl, 4-decyloxycarbonyl, 3,7-dimethyl-1-n-octyloxycarbonyl, 3,7-dimethyl-3-n-octyloxycarbonyl or the like may be mentioned.

A $C_{1-10}$ alkylcarbonyloxy group may be linear, branched or a $C_{3-10}$ cycloalkylcarbonyloxy group, and for example, methylcarbonyloxy, ethylcarbonyloxy, n-propylcarbonyloxy, i-propylcarbonyloxy, c-propylcarbonyloxy, n-butylcarbonyloxy, i-butylcarbonyloxy, s-butylcarbonyloxy, t-butylcarbonyloxy, c-butylcarbonyloxy, 1-methyl-c-propylcarbonyloxy, 2-methyl-c-propylcarbonyloxy, n-pentylcarbonyloxy, 1-methyl-n-butylcarbonyloxy, 2-methyl-n-butylcarbonyloxy, 3-methyl-n-butylcarbonyloxy, 1,1-dimethyl-n-propylcarbonyloxy, 1,2-dimethyl-n-propylcarbonyloxy, 2,2-dimethyl-n-propylcarbonyloxy, 1-ethyl-n-propylcarbonyloxy, c-pentylcarbonyloxy, 1-methyl-c-butylcarbonyloxy, 2-methyl-c-butylcarbonyloxy, 3-methyl-c-butylcarbonyloxy, 1,2-dimethyl-c-propylcarbonyloxy, 2,3-dimethyl-c-propylcarbonyloxy, 1-ethyl-c-propylcarbonyloxy, 2-ethyl-c-propylcarbonyloxy, n-hexylcarbonyloxy, 1-methyl-n-pentylcarbonyloxy, 2-methyl-n-pentylcarbonyloxy, 3-methyl-n-pentylcarbonyloxy, 4-methyl-n-pentylcarbonyloxy, 1,1-dimethyl-n-butylcarbonyloxy, 1,2-dimethyl-n-butylcarbonyloxy, 1,3-dimethyl-n-butylcarbonyloxy, 2,2-dimethyl-n-butylcarbonyloxy, 2,3-dimethyl-n-butylcarbonyloxy, 3,3-dimethyl-n-butylcarbonyloxy, 1-ethyl-n-butylcarbonyloxy, 2-ethyl-n-butylcarbonyloxy, 1,1,2-trimethyl-n-propylcarbonyloxy, 1,2,2-trimethyl-n-propylcarbonyloxy, 1-ethyl-1-methyl-n-propylcarbonyloxy, 1-ethyl-2-methyl-n-propylcarbonyloxy, c-hexylcarbonyloxy, 1-methyl-c-pentylcarbonyloxy, 2-methyl-c-pentylcarbonyloxy, 3-methyl-c-pentylcarbonyloxy, 1-ethyl-c-butylcarbonyloxy, 2-ethyl-c-butylcarbonyloxy, 3-ethyl-c-butylcarbonyloxy, 1,2-dimethyl-c-butylcarbonyloxy, 1,3-dimethyl-c-butylcarbonyloxy, 2,2-dimethyl-c-butylcarbonyloxy, 2,3-dimethyl-c-butylcarbonyloxy, 2,4-dimethyl-c-butylcarbonyloxy, 3,3-dimethyl-c-butylcarbonyloxy, 1-n-propyl-c-propylcarbonyloxy, 2-n-propyl-c-propylcarbonyloxy, 1-i-propyl-c-propylcarbonyloxy, 2-i-propyl-c-propylcarbonyloxy, 1,2,2-trimethyl-c-propylcarbonyloxy, 1,2,3-trimethyl-c-propylcarbonyloxy, 2,2,3-trimethyl-c-propylcarbonyloxy, 1-ethyl-2-methyl-c-propylcarbonyloxy, 2-ethyl-1-methyl-c-propylcarbonyloxy, 2-ethyl-2-methyl-c-propylcarbonyloxy, 2-ethyl-3-methyl-c-propylcarbonyloxy, 1-methyl-1-ethyl-n-pentylcarbonyloxy, 1-heptylcarbonyloxy, 2-heptylcarbonyloxy, 1-ethyl-1,2-dimethyl-n-propylcarbonyloxy, 1-ethyl-2,2-dimethyl-n-propylcarbonyloxy, 1-octylcarbonyloxy, 3-octylcarbonyloxy, 4-methyl-3-n-heptylcarbonyloxy, 6-methyl-2-n-heptylcarbonyloxy, 2-propyl-1-n-heptylcarbonyloxy, 2,4,4-trimethyl-1-n-pentylcarbonyloxy, 1-nonylcarbonyloxy, 2-nonylcarbonyloxy, 2,6-dimethyl-4-n-heptylcarbonyloxy, 3-ethyl-2,2-dimethyl-3-n-pentylcarbonyloxy, 3,5,5-trimethyl-1-n-hexylcarbonyloxy, 1-decylcarbonyloxy, 2-decylcarbonyloxy, 4-decylcarbonyloxy, 3,7-dimethyl-1-n-octylcarbonyloxy, 3,7-dimethyl-3-n-octylcarbonyloxy or the like may be mentioned.

A $C_{1-10}$ alkylcarbonylamino group may be linear, branched or a $C_{3-10}$ cycloalkylcarbonylamino group, and for example, methylcarbonylamino, ethylcarbonylamino, n-propylcarbonylamino, i-propylcarbonylamino, c-propylcarbonylamino, n-butylcarbonylamino, i-butylcarbonylamino, s-butylcarbonylamino, t-butylcarbonylamino, c-butylcarbonylamino, 1-methyl-c-propylcarbonylamino, 2-methyl-c-propylcarbonylamino, n-pentylcarbonylamino, 1-methyl-n-butylcarbonylamino, 2-methyl-n-butylcarbonylamino, 3-methyl-n-butylcarbonylamino, 1,1-dimethyl-n-propylcarbonylamino, 1,2-dimethyl-n-propylcarbonylamino, 2,2-dimethyl-n-propylcarbonylamino, 1-ethyl-n-propylcarbonylamino, c-pentylcarbonylamino, 1-methyl-c-butylcarbonylamino, 2-methyl-c-butylcarbonylamino, 3-methyl-c-butylcarbonylamino, 1,2-dimethyl-c-propylcarbonylamino, 2,3-dimethyl-c-propylcarbonylamino, 1-ethyl-c-propylcarbonylamino, 2-ethyl-c-propylcarbonylamino, n-hexylcarbonylamino, 1-methyl-n-pentylcarbonylamino, 2-methyl-n-pentylcarbonylamino, 3-methyl-n-pentylcarbonylamino, 4-methyl-n-pentylcarbonylamino, 1,1-dimethyl-n-butylcarbonylamino, 1,2-dimethyl-n-butylcarbonylamino, 1,3-dimethyl-n-butylcarbonylamino, 2,2-dimethyl-n-butylcarbonylamino, 2,3-dimethyl-n-butylcarbonylamino, 3,3-dimethyl-n-butylcarbonylamino, 1-ethyl-n-butylcarbonylamino, 2-ethyl-n-butylcarbonylamino, 1,1,2-trimethyl-n-propylcarbonylamino, 1,2,2-trimethyl-n-propylcarbonylamino, 1-ethyl-1-methyl-n-propylcarbonylamino, 1-ethyl-2-methyl-n-propylcarbonylamino, c-hexylcarbonylamino, 1-methyl-c-pentylcarbonylamino, 2-methyl-c-pentylcarbonylamino, 3-methyl-c-pentylcarbonylamino, 1-ethyl-c-butylcarbonylamino, 2-ethyl-c-butylcarbonylamino, 3-ethyl-c-butylcarbonylamino, 1,2-dimethyl-c-butylcarbonylamino, 1,3-dimethyl-c-butylcarbonylamino, 2,2-dimethyl-c-butylcarbonylamino, 2,3-dimethyl-c-butylcarbonylamino, 2,4-dimethyl-c-butylcarbonylamino, 3,3-dimethyl-c-butylcarbonylamino, 1-n-propyl-c-propylcarbonylamino, 2-n-propyl-c-propylcarbonylamino, 1-i-propyl-c-propylcarbonylamino, 2-i-propyl-c-propylcarbonylamino, 1,2,2-trimethyl-c-propylcarbonylamino, 1,2,3-trimethyl-c-propylcarbonylamino, 2,2,3-trimethyl-c-propylcarbonylamino, 1-ethyl-2-methyl-c-propylcarbonylamino, 2-ethyl-1-methyl-c-propylcarbonylamino, 2-ethyl-2-methyl-c-propylcarbonylamino, 2-ethyl-3-methyl-c-propylcarbonylamino, 1-methyl-1-ethyl-n-pentylcarbonylamino, 1-heptylcarbonylamino, 2-heptylcarbonylamino, 1-ethyl-1,2-dimethyl-n-propylcarbonylamino, 1-ethyl-2,2-dimethyl-n-propylcarbonylamino, 1-octylcarbonylamino, 3-octylcarbonylamino, 4-methyl-3-n-heptylcarbonylamino, 6-methyl-2-n-heptylcarbonylamino, 2-propyl-1-n-heptylcarbonylamino, 2,4,4-trimethyl-1-n-pentylcarbonylamino, 1-nonylcarbonylamino, 2-nonylcarbonylamino, 2,6-dimethyl-4-n-heptylcarbonylamino, 3-ethyl-2,2-dimethyl-3-n-pentylcarbonylamino, 3,5,5-trimethyl-1-n-hexylcarbonylamino, 1-decylcarbonylamino, 2-decylcarbonylamino, 4-decylcarbonylamino, 3,7-dimethyl-1-n-octylcarbonylamino, 3,7-dimethyl-3-n-octylcarbonylamino or the like may be mentioned.

A $C_{1-10}$ monoalkylamino group may be linear, branched or a $C_{3-10}$ cycloalkylamino group, and for example, methylamino, ethylamino, n-propylamino, i-propylamino, c-propylamino, n-butylamino, i-butylamino, s-butylamino, t-butylamino, c-butylamino, 1-methyl-c-propylamino, 2-methyl-c-propylamino, n-pentylamino, 1-methyl-n-butylamino, 2-methyl-n-butylamino, 3-methyl-n-butylamino, 1,1-dimethyl-n-propylamino, 1,2-dimethyl-n-propylamino, 2,2-dimethyl-n-propylamino, 1-ethyl-n-propylamino, c-pentylamino, 1-methyl-c-butylamino, 2-methyl-c-butylamino, 3-methyl-c-butylamino, 1,2-dimethyl-c-propylamino, 2,3-dimethyl-c-propylamino, 1-ethyl-c-propylamino, 2-ethyl-c-propylamino, n-hexylamino, 1-methyl-n-pentylamino, 2-methyl-n-pentylamino, 3-methyl-n-pentylamino, 4-methyl-n-pentylamino, 1,1-dimethyl-n-butylamino, 1,2-dimethyl-n-butylamino, 1,3-dimethyl-n-butylamino, 2,2-dimethyl-n-butylamino, 2,3-dimethyl-n-butylamino, 3,3-dimethyl-n-butylamino, 1-ethyl-n-butylamino, 2-ethyl-n-butylamino, 1,1,2-trimethyl-n-propylamino, 1,2,2-trimethyl-n-propylamino, 1-ethyl-1-methyl-n-propylamino, 1-ethyl-2-methyl-n-propylamino, c-hexylamino, 1-methyl-c-pentylamino, 2-methyl-c-pentylamino, 3-methyl-c-pentylamino, 1-ethyl-c-butylamino, 2-ethyl-c-butylamino, 3-ethyl-c-butylamino, 1,2-dimethyl-c-butylamino, 1,3-dimethyl-c-butylamino, 2,2-dimethyl-c-butylamino, 2,3-dimethyl-c-butylamino, 2,4-dimethyl-c-butylamino, 3,3-dimethyl-c-butylamino, 1-n-propyl-c-propylamino, 2-n-propyl-c-propylamino, 1-i-propyl-c-propylamino, 2-i-propyl-c-propylamino, 1,2,2-trimethyl-c-propylamino, 1,2,3-trimethyl-c-propylamino, 2,2,3-trimethyl-c-propylamino, 1-ethyl-2-methyl-c-propylamino, 2-ethyl-1-methyl-c-propylamino, 2-ethyl-2-methyl-c-propylamino, 2-ethyl-3-methyl-c-propylamino, 1-methyl-1-ethyl-n-pentylamino, 1-heptylamino, 2-heptylamino, 1-ethyl-1,2-dimethyl-n-propylamino, 1-ethyl-2,2-dimethyl-n-propylamino, 1-octylamino, 3-octylamino, 4-methyl-3-n-heptylamino, 6-methyl-2-n-heptylamino, 2-propyl-1-n-heptylamino, 2,4,4-trimethyl-1-n-pentylamino, 1-nonylamino, 2-nonylamino, 2,6-dimethyl-4-n-heptylamino, 3-ethyl-2,2-dimethyl-3-n-pentylamino, 3,5,5-trimethyl-1-n-hexylamino, 1-decylamino, 2-decylamino, 4-decylamino, 3,7-dimethyl-1-n-octylamino, 3,7-dimethyl-3-n-octylamino or the like may be mentioned.

A $C_{1-10}$ dialkylamino group may be symmetric or asymmetric. A symmetric $C_{1-10}$ dialkylamino group may be linear, branched or a $C_{3-10}$ cycloalkylamino group, and for example, dimethylamino, diethylamino, di-n-propylamino, di-i-propylamino, di-c-propylamino, di-n-butylamino, di-i-butylamino, di-s-butylamino, di-t-butylamino, di-c-butylamino, di-(1-methyl-c-propyl)amino, di-(2-methyl-c-propyl)amino, di-n-pentylamino, di-(1-methyl-n-butyl)amino, di-(2-methyl-n-butyl)amino, di-(3-methyl-n-butyl)amino, di-(1,1-dimethyl-n-propyl)amino, di-(1,2-dimethyl-n-propyl)amino, di-(2,2-dimethyl-n-propyl)amino, di-(1-ethyl-n-propyl)amino, di-c-pentylamino, di-(1-methyl-c-butyl)amino, di-(2-methyl-c-butyl)amino, di-(3-methyl-c-butyl)amino, di-(1,2-dimethyl-c-propyl)amino, di-(2,3-dimethyl-c-propyl)amino, di-(1-ethyl-c-propyl)amino, di-(2-ethyl-c-propyl)amino, di-n-hexylamino, di-(1-methyl-n-pentyl)amino, di-(2-methyl-n-pentyl)amino, di-(3-methyl-n-pentyl)amino, di-(4-methyl-n-pentyl)amino, di-(1,1-dimethyl-n-butyl)amino, di-(1,2-dimethyl-n-butyl)amino, di-(1,3-dimethyl-n-butyl)amino, di-(2,2-dimethyl-n-butyl)amino, di-(2,3-dimethyl-n-butyl)amino, di-(3,3-dimethyl-n-butyl)amino, di-(1-ethyl-n-butyl)amino, di-(2-ethyl-n-butyl)amino, di-(1,1,2-trimethyl-n-propyl)amino, di-(1,2,2-trimethyl-n-propyl)amino, di-(1-ethyl-1-methyl-n-propyl)amino, di-(1-ethyl-2-methyl-n-propyl)amino, di-c-hexylamino, di-(1-methyl-c-pentyl)amino, di-(2-methyl-c-pentyl)amino, di-(3-methyl-c-pentyl)amino, di-(1-ethyl-c-butyl)amino, di-(2-ethyl-c-butyl)amino, di-(3-ethyl-c-butyl)amino, di-(1,2-dimethyl-c-butyl)amino, di-(1,3-dimethyl-c-butyl)amino, di-(2,2-dimethyl-c-butyl)amino, di-(2,3-dimethyl-c-butyl)amino, di-(2,4-dimethyl-c-butyl)amino, di-(3,3-dimethyl-c-butyl)amino, di-(1-n-propyl-c-propyl)amino, di-(2-n-propyl-c-propyl)amino, di-(1-i-propyl-c-propyl)amino, di-(2-i-propyl-c-propyl)amino, di-(1,2,2-trimethyl-c-propyl)amino, di-(1,2,3-trimethyl-c-propyl)amino, di-(2,2,3-trimethyl-c-propyl)amino, di-(1-ethyl-2-methyl-c-propyl)amino, di-(2-ethyl-1-methyl-c-propyl)amino, di-(2-ethyl-2-methyl-c-propyl)amino, di-(2-ethyl-3-methyl-c-propyl)amino, di-(1-methyl-1-ethyl-n-pentyl)amino, di-(1-heptyl)amino, di-(2-heptyl)amino, di-(1-ethyl-1,2-dimethyl-n-propyl)amino, di-(1-ethyl-2,2-dimethyl-n-propyl)amino, di-(1-octyl)amino, di-(3-octyl)amino, di-(4-methyl-3-n-heptyl)amino, di-(6-methyl-2-n-heptyl)amino, di-(2-propyl-1-n-heptyl)amino, di-(2,4,4-trimethyl-1-n-pentyl)amino, di-(1-nonyl)amino, di-(2-nonyl)amino, di-(2,6-dimethyl-4-n-heptyl)amino, di-(3-ethyl-2,2-dimethyl-3-n-pentyl)amino, di-(3,5,5-trimethyl-1-n-hexyl)amino, di-(1-decyl)amino, di-(2-decyl)amino, di-(4-decyl)amino, di-(3,7-dimethyl-1-n-octyl)amino, di-(3,7-dimethyl-3-n-octyl)amino or the like may be mentioned.

An asymmetric $C_{1-10}$ dialkylamino group may be linear, branched or a $C_{3-10}$ cycloalkylamino group, and for example, (methyl, ethyl)amino, (methyl, n-propyl)amino, (methyl, i-propyl)amino, (methyl, c-propyl)amino, (methyl, n-butyl)amino, (methyl, i-butyl)amino, (methyl, s-butyl)amino, (methyl, t-butyl)amino, (methyl, n-pentyl)amino, (methyl, c-pentyl)amino, (methyl, n-hexyl)amino, (methyl, c-hexyl)amino, (ethyl, n-propyl)amino, (ethyl, i-propyl)amino, (ethyl, c-propyl)amino, (ethyl, n-butyl)amino, (ethyl, i-butyl)amino, (ethyl, s-butyl)amino, (ethyl, t-butyl)amino, (ethyl, n-pentyl)amino, (ethyl, c-pentyl)amino, (ethyl, n-hexyl)amino, (ethyl, c-hexyl)amino, (n-propyl, i-propyl)amino, (n-propyl, c-propyl)amino, (n-propyl, n-butyl)amino, (n-propyl, i-butyl)amino, (n-propyl, s-butyl)amino, (n-propyl, t-butyl)amino, (n-propyl, n-pentyl)amino, (n-propyl, c-pentyl)amino, (n-propyl, n-hexyl)amino, (n-propyl, c-hexyl)amino, (i-propyl, c-propyl)amino, (i-propyl, n-butyl)amino, (i-propyl, i-butyl)amino, (i-propyl, s-butyl)amino, (i-propyl, t-butyl)amino, (i-propyl, n-pentyl)amino, (i-propyl, c-pentyl)amino, (i-propyl, n-hexyl)amino, (i-propyl, c-hexyl)amino, (c-propyl, n-butyl)amino, (c-propyl, i-butyl)amino, (c-propyl, s-butyl)amino, (c-propyl, t-butyl)amino, (c-propyl, n-pentyl)amino, (c-propyl, c-pentyl)amino, (c-propyl, n-hexyl)amino, (c-propyl, c-hexyl)amino, (n-butyl, i-butyl)amino, (n-butyl, s-butyl)amino, (n-butyl, t-butyl)amino, (n-butyl, n-pentyl)amino, (n-butyl, c-pentyl)amino, (n-butyl, n-hexyl)amino, (n-butyl, c-hexyl)amino, (i-butyl, s-butyl)amino, (i-butyl, t-butyl)amino, (i-butyl, n-pentyl)amino, (i-butyl, c-pentyl)amino, (i-butyl, n-hexyl)amino, (i-butyl, c-hexyl)amino, (s-butyl, t-butyl)amino, (s-butyl, n-pentyl)amino, (s-butyl, c-pentyl)amino, (s-butyl, n-hexyl)amino, (s-butyl, c-hexyl)amino, (t-butyl, n-pentyl)amino, (t-butyl, c-pentyl)amino, (t-butyl, n-hexyl)amino, (t-butyl, c-hexyl)amino, (n-pentyl, c-pentyl)amino, (n-pentyl, n-hexyl)amino, (n-pentyl, c-hexyl)amino, (c-pentyl, n-hexyl)amino, (c-pentyl, c-hexyl)amino, (n-hexyl, c-hexyl)amino, (methyl, n-heptyl)amino, (methyl, n-octyl)amino, (methyl, n-nonanyl)amino, (methyl, n-decyl)amino, (methyl, n-heptyl)amino, (ethyl, n-octyl)amino, (ethyl, n-nonanyl)amino, (ethyl, n-decyl)amino or the like may be mentioned.

A $C_{1-10}$ alkylaminocarbonyl group may be a $C_{1-10}$ monoalkylaminocarbonyl group or a $C_{1-10}$ dialkylaminocarbonyl group.

A $C_{1-10}$ monoalkylaminocarbonyl group may be linear, branched or a $C_{3-10}$ cycloalkylaminocarbonyl group, and for example, methylaminocarbonyl, ethylaminocarbonyl, n-propylaminocarbonyl, i-propylaminocarbonyl, c-propylaminocarbonyl, n-butylaminocarbonyl, i-butylaminocarbonyl, s-butylaminocarbonyl, t-butylaminocarbonyl, c-butylaminocarbonyl, 1-methyl-c-propylaminocarbonyl, 2-methyl-c-propylaminocarbonyl, n-pentylaminocarbonyl, 1-methyl-n-butylaminocarbonyl, 2-methyl-n-butylaminocarbonyl, 3-methyl-n-butylaminocarbonyl, 1,1-dimethyl-n-propylaminocarbonyl, 1,2-dimethyl-n-propylaminocarbonyl, 2,2-dimethyl-n-propylaminocarbonyl, 1-ethyl-n-propylaminocarbonyl, c-pentylaminocarbonyl, 1-methyl-c-butylaminocarbonyl, 2-methyl-c-butylaminocarbonyl, 3-methyl-c-butylaminocarbonyl, 1,2-dimethyl-c-propylaminocarbonyl, 2,3-dimethyl-c-propylaminocarbonyl, 1-ethyl-c-propylaminocarbonyl, 2-ethyl-c-propylaminocarbonyl, n-hexylaminocarbonyl, 1-methyl-n-pentylaminocarbonyl, 2-methyl-n-pentylaminocarbonyl, 3-methyl-n-pentylaminocarbonyl, 4-methyl-n-pentylaminocarbonyl, 1,1-dimethyl-n-butylaminocarbonyl, 1,2-dimethyl-n-butylaminocarbonyl, 1,3-dimethyl-n-butylaminocarbonyl, 2,2-dimethyl-n-butylaminocarbonyl, 2,3-dimethyl-n-butylaminocarbonyl, 3,3-dimethyl-n-butylaminocarbonyl, 1-ethyl-n-butylaminocarbonyl, 2-ethyl-n-butylaminocarbonyl, 1,1,2-trimethyl-n-propylaminocarbonyl, 1,2,2-trimethyl-n-propylaminocarbonyl, 1-ethyl-1-methyl-n-propylaminocarbonyl, 1-ethyl-2-methyl-n-propylaminocarbonyl, c-hexylaminocarbonyl, 1-methyl-c-pentylaminocarbonyl, 2-methyl-c-pentylaminocarbonyl, 3-methyl-c-pentylaminocarbonyl, 1-ethyl-c-butylaminocarbonyl, 2-ethyl-c-butylaminocarbonyl, 3-ethyl-c-butylaminocarbonyl, 1,2-dimethyl-c-butylaminocarbonyl, 1,3-dimethyl-c-butylaminocarbonyl, 2,2-dimethyl-c-butylaminocarbonyl, 2,3-dimethyl-c-butylaminocarbonyl, 2,4-dimethyl-c-butylaminocarbonyl, 3,3-dimethyl-c-butylaminocarbonyl, 1-n-propyl-c-propylaminocarbonyl, 2-n-propyl-c-propylaminocarbonyl, 1-i-propyl-c-propylaminocarbonyl, 2-i-propyl-c-propylaminocarbonyl, 1,2,2-trimethyl-c-propylaminocarbonyl, 1,2,3-trimethyl-c-propylaminocarbonyl, 2,2,3-trimethyl-c-propylaminocarbonyl, 1-ethyl-2-methyl-c-propylaminocarbonyl, 2-ethyl-1-methyl-c-propylaminocarbonyl, 2-ethyl-2-methyl-c-propylaminocarbonyl, 2-ethyl-3-methyl-c-propylaminocarbonyl, 1-methyl-1-ethyl-n-pentylaminocarbonyl, 1-heptylaminocarbonyl, 2-heptylaminocarbonyl, 1-ethyl-1,2-dimethyl-n-propylaminocarbonyl, 1-ethyl-2,2-dimethyl-n-propylaminocarbonyl, 1-octylaminocarbonyl, 3-octylaminocarbonyl, 4-methyl-3-n-heptylaminocarbonyl, 6-methyl-2-n-heptylaminocarbonyl, 2-propyl-1-n-heptylaminocarbonyl, 2,4,4-trimethyl-1-n-pentylaminocarbonyl, 1-nonylaminocarbonyl, 2-nonylaminocarbonyl, 2,6-dimethyl-4-n-heptylaminocarbonyl, 3-ethyl-2,2-dimethyl-3-n-pentylaminocarbonyl, 3,5,5-trimethyl-1-n-hexylaminocarbonyl, 1-decylaminocarbonyl, 2-decylaminocarbonyl, 4-decylaminocarbonyl, 3,7-dimethyl-1-n-octylaminocarbonyl, 3,7-dimethyl-3-n-octylaminocarbonyl or the like may be mentioned.

A $C_{1-10}$ dialkylaminocarbonyl group may be symmetric or asymmetric. A symmetric $C_{1-10}$ dialkylaminocarbonyl group may be linear, branched or a $C_{3-10}$ cycloalkylaminocarbonyl group, and for example, dimethylaminocarbonyl, diethylaminocarbonyl, di-n-propylaminocarbonyl, di-i-propylaminocarbonyl, di-c-propylaminocarbonyl, di-n-butylaminocarbonyl, di-i-butylaminocarbonyl, di-s-butylaminocarbonyl, di-t-butylaminocarbonyl, di-c-butylaminocarbonyl, di-(1-methyl-c-propyl)aminocarbonyl, di-(2-methyl-c-propyl)aminocarbonyl, di-n-pentylaminocarbonyl, di-(1-methyl-n-butyl)aminocarbonyl, di-(2-methyl-n-butyl)aminocarbonyl, di-(3-methyl-n-butyl)aminocarbonyl, di-(1,1-dimethyl-n-propyl)aminocarbonyl, di-(1,2-dimethyl-n-propyl)aminocarbonyl, di-(2,2-dimethyl-n-propyl)aminocarbonyl, di-(1-ethyl-n-propyl)aminocarbonyl, di-c-pentylaminocarbonyl, di-(1-methyl-c-butyl)aminocarbonyl, di-(2-methyl-c-butyl)aminocarbonyl, di-(3-methyl-c-butyl)aminocarbonyl, di-(1,2-dimethyl-c-propyl)aminocarbonyl, di-(2,3-dimethyl-c-propyl)aminocarbonyl, di-(1-ethyl-c-propyl)aminocarbonyl, di-(2-ethyl-c-propyl)aminocarbonyl, di-n-hexylaminocarbonyl, di-(1-methyl-n-pentyl)aminocarbonyl, di-(2-methyl-n-pentyl)aminocarbonyl, di-(3-methyl-n-pentyl)aminocarbonyl, di-(4-methyl-n-pentyl)aminocarbonyl, di-(1,1-dimethyl-n-butyl)aminocarbonyl, di-(1,2-dimethyl-n-butyl)aminocarbonyl, di-(1,3-dimethyl-n-butyl)aminocarbonyl, di-(2,2-dimethyl-n-butyl)aminocarbonyl, di-(2,3-dimethyl-n-butyl)aminocarbonyl, di-(3,3-dimethyl-n-butyl)aminocarbonyl, di-(1-ethyl-n-butyl)aminocarbonyl, di-(2-ethyl-n-butyl)aminocarbonyl, di-(1,1,2-trimethyl-n-propyl)aminocarbonyl, di-(1,2,2-trimethyl-n-propyl)aminocarbonyl, di-(1-ethyl-1-methyl-n-propyl)aminocarbonyl, di-(1-ethyl-2-methyl-n-propyl)aminocarbonyl, di-c-hexylaminocarbonyl, di-(1-methyl-c-pentyl)aminocarbonyl, di-(2-methyl-c-pentyl)aminocarbonyl, di-(3-methyl-c-pentyl)aminocarbonyl, di-(1-ethyl-c-butyl)aminocarbonyl, di-(2-ethyl-c-butyl)aminocarbonyl, di-(3-ethyl-c-butyl)aminocarbonyl, di-(1,2-dimethyl-c-butyl)aminocarbonyl, di-(1,3-dimethyl-c-butyl)aminocarbonyl, di-(2,2-dimethyl-c-butyl)aminocarbonyl, di-(2,3-dimethyl-c-butyl)aminocarbonyl, di-(2,4-dimethyl-c-butyl)aminocarbonyl, di-(3,3-dimethyl-c-butyl)aminocarbonyl, di-(1-n-propyl-c-propyl)aminocarbonyl, di-(2-n-propyl-c-propyl)aminocarbonyl, di-(1-i-propyl-c-propyl)aminocarbonyl, di-(2-i-propyl-c-propyl)aminocarbonyl, di-(1,2,2-trimethyl-c-propyl)aminocarbonyl, di-(1,2,3-trimethyl-c-propyl)aminocarbonyl, di-(2,2,3-trimethyl-c-propyl)aminocarbonyl, di-(1-ethyl-2-methyl-c-propyl)aminocarbonyl, di-(2-ethyl-1-methyl-c-propyl)aminocarbonyl, di-(2-ethyl-2-methyl-c-propyl)aminocarbonyl, di-(2-ethyl-3-methyl-c-propyl)aminocarbonyl, di-(1-methyl-1-ethyl-n-pentyl)aminocarbonyl, di-(1-heptyl)aminocarbonyl, di-(2-heptyl)aminocarbonyl, di-(1-ethyl-1,2-dimethyl-n-propyl)aminocarbonyl, di-(1-ethyl-2,2-dimethyl-n-propyl)aminocarbonyl, di-(1-octyl)aminocarbonyl, di-(3-octyl)aminocarbonyl, di-(4-methyl-3-n-heptyl)aminocarbonyl, di-(6-methyl-2-n-heptyl)aminocarbonyl, di-(2-propyl-1-n-heptyl)aminocarbonyl, di-(2,4,4-trimethyl-1-n-pentyl)aminocarbonyl, di-(1-nonyl)aminocarbonyl, di-(2-nonyl)aminocarbonyl, di-(2,6-dimethyl-4-n-heptyl)aminocarbonyl, di-(3-ethyl-2,2-dimethyl-3-n-pentyl)aminocarbonyl, di-(3,5,5-trimethyl-1-n-hexyl)aminocarbonyl, di-(1-decyl)aminocarbonyl, di-(2-decyl)aminocarbonyl, di-(4-decyl)aminocarbonyl, di-(3,7-dimethyl-1-n-octyl)aminocarbonyl, di-(3,7-dimethyl-3-n-octyl)aminocarbonyl or the like may be mentioned.

A $C_{1-10}$ dialkylaminocarbonyl group may be an asymmetric $C_{1-10}$ dialkylaminocarbonyl group or a symmetric $C_{1-10}$ dialkylaminocarbonyl group.

An asymmetric $C_{1-10}$ dialkylaminocarbonyl group may be linear, branched or a $C_{3-10}$ cycloalkylaminocarbonyl group, and for example, (methyl, ethyl)aminocarbonyl, (methyl, n-propyl)aminocarbonyl, (methyl, i-propyl)aminocarbonyl, (methyl, c-propyl)aminocarbonyl, (methyl, n-butyl)aminocarbonyl, (methyl, i-butyl)aminocarbonyl, (methyl, s-butyl)aminocarbonyl, (methyl, t-butyl)aminocarbonyl, (methyl, n-pentyl)aminocarbonyl, (methyl, c-pentyl)aminocarbonyl, (methyl, n-hexyl)aminocarbonyl, (methyl, c-hexyl)aminocarbonyl, (ethyl, n-propyl)aminocarbonyl, (ethyl, i-propyl)aminocarbonyl, (ethyl, i-propyl)aminocarbonyl, (ethyl, c-propyl)aminocarbonyl, (ethyl, n-butyl)aminocarbonyl, (ethyl, i-butyl)aminocarbonyl, (ethyl, s-butyl)aminocarbonyl, (ethyl, t-butyl)aminocarbonyl, (ethyl, n-pentyl)aminocarbonyl, (ethyl, c-pentyl)aminocarbonyl, (ethyl, n-hexyl)aminocarbonyl, (ethyl, c-hexyl)aminocarbonyl, (n-propyl, i-propyl)aminocarbonyl, (n-propyl, c-propyl)aminocarbonyl, (n-propyl, n-butyl)aminocarbonyl, (n-propyl, i-butyl)aminocarbonyl, (n-propyl, s-butyl)aminocarbonyl, (n-propyl, t-butyl)aminocarbonyl, (n-propyl, n-pentyl)aminocarbonyl, (n-propyl, c-pentyl)aminocarbonyl, (n-propyl, n-hexyl)aminocarbonyl, (n-propyl, c-hexyl)aminocarbonyl, (i-propyl, c-propyl)aminocarbonyl, (i-propyl, n-butyl)aminocarbonyl, (i-propyl, i-butyl)aminocarbonyl, (i-propyl, s-butyl)aminocarbonyl, (i-propyl, t-butyl)aminocarbonyl, (i-propyl, n-pentyl)aminocarbonyl, (i-propyl, c-pentyl)aminocarbonyl, (i-propyl, n-hexyl)aminocarbonyl, (i-propyl, c-hexyl)aminocarbonyl, (c-propyl, n-butyl)aminocarbonyl, (c-propyl, i-butyl)aminocarbonyl, (c-propyl, s-butyl)aminocarbonyl, (c-propyl, t-butyl)aminocarbonyl, (c-propyl, n-pentyl)aminocarbonyl, (c-propyl, c-pentyl)aminocarbonyl, (c-propyl, n-hexyl)aminocarbonyl, (c-propyl, c-hexyl)aminocarbonyl, (n-butyl, i-butyl)aminocarbonyl, (n-butyl, s-butyl)aminocarbonyl, (n-butyl, t-butyl)aminocarbonyl, (n-butyl, n-pentyl)aminocarbonyl, (n-butyl, c-pentyl)aminocarbonyl, (n-butyl, n-hexyl)aminocarbonyl, (n-butyl, c-hexyl)aminocarbonyl, (i-butyl, s-butyl)aminocarbonyl, (i-butyl, t-butyl)aminocarbonyl, (i-butyl, n-pentyl)aminocarbonyl, (i-butyl, c-pentyl)aminocarbonyl, (i-butyl, n-hexyl)aminocarbonyl, (i-butyl, c-hexyl)aminocarbonyl, (s-butyl, t-butyl)aminocarbonyl, (s-butyl, n-pentyl)aminocarbonyl, (s-butyl, c-pentyl)aminocarbonyl, (s-butyl, n-hexyl)aminocarbonyl, (s-butyl, c-hexyl)aminocarbonyl, (t-butyl, n-pentyl)aminocarbonyl, (t-butyl, c-pentyl)aminocarbonyl, (t-butyl, n-hexyl)aminocarbonyl, (t-butyl, c-hexyl)aminocarbonyl, (n-pentyl, c-pentyl)aminocarbonyl, (n-pentyl, n-hexyl)aminocarbonyl, (n-pentyl, c-hexyl)aminocarbonyl, (c-pentyl, n-hexyl)aminocarbonyl, (c-pentyl, c-hexyl)aminocarbonyl, (n-hexyl, c-hexyl)aminocarbonyl, (methyl, n-heptyl)aminocarbonyl, (methyl, n-octyl)aminocarbonyl, (methyl, n-nonanyl)aminocarbonyl, (methyl, n-decyl)aminocarbonyl, (methyl, n-heptyl)aminocarbonyl, (ethyl, n-octyl)aminocarbonyl, (ethyl, n-nonanyl)aminocarbonyl, (ethyl, n-decyl)aminocarbonyl or the like may be mentioned.

A $C_{1-6}$ alkylaminosulfonyl group may be linear, branched or a $C_{3-6}$ cycloalkylaminosulfonyl group, and for example, methylaminosulfonyl, ethylaminosulfonyl, n-propylaminosulfonyl, i-propylaminosulfonyl, c-propylaminosulfonyl, n-butylaminosulfonyl, i-butylaminosulfonyl, s-butylaminosulfonyl, t-butylaminosulfonyl, c-butylaminosulfonyl, 1-methyl-c-propylaminosulfonyl, 2-methyl-c-propylaminosulfonyl, n-pentylaminosulfonyl, 1-methyl-n-butylaminosulfonyl, 2-methyl-n-butylaminosulfonyl, 3-methyl-n-butylaminosulfonyl, 1,1-dimethyl-n-propylaminosulfonyl, 1,2-dimethyln-propylaminosulfonyl, 2,2-dimethyln-propylaminosulfonyl, 1-ethyl-n-propylaminosulfonyl, c-pentylaminosulfonyl, 1-methyl-c-butylaminosulfonyl, 2-methyl-c-butylaminosulfonyl, 3-methyl-c-butylaminosulfonyl, 1,2-dimethyl-c-propylaminosulfonyl, 2,3-dimethyl-c-propylaminosulfonyl, 1-ethyl-c-propylaminosulfonyl, 2-ethyl-c-propylaminosulfonyl, n-hexylaminosulfonyl, 1-methyl-n-pentylaminosulfonyl, 2-methyl-n-pentylaminosulfonyl, 3-methyl-n-pentylaminosulfonyl, 4-methyl-n-pentylaminosulfonyl, 1,1-dimethyl-n-butylaminosulfonyl, 1,2-dimethyl-n-butylaminosulfonyl, 1,3-dimethyl-n-butylaminosulfonyl, 2,2-dimethyl-n-butylaminosulfonyl, 2,3-dimethyl-n-butylaminosulfonyl, 3,3-dimethyl-n-butylaminosulfonyl, 1-ethyl-n-butylaminosulfonyl, 2-ethyl-n-butylaminosulfonyl, 1,1,2-trimethyl-n-propylaminosulfonyl, 1,2,2-trimethyl-n-propylaminosulfonyl, 1-ethyl-1-methyl-n-propylaminosulfonyl, 1-ethyl-2-methyl-n-propylaminosulfonyl, c-hexylaminosulfonyl, 1-methyl-c-pentylaminosulfonyl, 2-methyl-c-pentylaminosulfonyl, 3-methyl-c-pentylaminosulfonyl, 1-ethyl-c-butylaminosulfonyl, 2-ethyl-c-butylaminosulfonyl, 3-ethyl-c-butylaminosulfonyl, 1,2-dimethyl-c-butylaminosulfonyl, 1,3-dimethyl-c-butylaminosulfonyl, 2,2-dimethyl-c-butylaminosulfonyl, 2,3-dimethyl-c-butylaminosulfonyl, 2,4-dimethyl-c-butylaminosulfonyl, 3,3-dimethyl-c-butylaminosulfonyl, 1-n-propyl-c-propylaminosulfonyl, 2-n-propyl-c-propylaminosulfonyl, 1-i-propyl-c-propylaminosulfonyl, 2-i-propyl-c-propylaminosulfonyl, 1,2,2-trimethyl-c-propylaminosulfonyl, 1,2,3-trimethyl-c-propylaminosulfonyl, 2,2,3-trimethyl-c-propylaminosulfonyl, 1-ethyl-2-methyl-c-propylaminosulfonyl, 2-ethyl-1-methyl-c-propylaminosulfonyl, 2-ethyl-2-methyl-c-propylaminosulfonyl, 2-ethyl-3-methyl-c-propylaminosulfonyl or the like may be mentioned.

A $C_{1-10}$ alkylaminosulfonyl group may be linear, branched or a $C_{3-10}$ cycloalkylsulfonylamino group, and for example, in addition to those mentioned above, 1-methyl-1-ethyl-n-pentylaminosulfonyl, 1-heptylaminosulfonyl, 2-heptylaminosulfonyl, 1-ethyl-1,2-dimethyl-n-propylaminosulfonyl, 1-ethyl-2,2-dimethyl-n-propylaminosulfonyl, 1-octylaminosulfonyl, 3-octylaminosulfonyl, 4-methyl-3-n-heptylaminosulfonyl, 6-methyl-2-n-heptylaminosulfonyl, 2-propyl-1-n-heptylaminosulfonyl, 2,4,4-trimethyl-1-n-pentylaminosulfonyl, 1-nonylaminosulfonyl, 2-nonylaminosulfonyl, 2,6-dimethyl-4-n-heptylaminosulfonyl, 3-ethyl-2,2-dimethyl-3-n-pentylaminosulfonyl, 3,5,5-trimethyl-1-n-hexylaminosulfonyl, 1-decylaminosulfonyl, 2-decylaminosulfonyl, 4-decylaminosulfonyl, 3,7-dimethyl-1-n-octylaminosulfonyl, 3,7-dimethyl-3-n-octylaminosulfonyl, c-heptylaminosulfonyl, c-octylaminosulfonyl, 1-methyl-c-hexylaminosulfonyl, 2-methyl-c-hexylaminosulfonyl, 3-methyl-c-hexylaminosulfonyl, 1,2-dimethyl-c-hexylaminosulfonyl, 1-ethyl-c-hexylaminosulfonyl, 1-methyl-c-pentylaminosulfonyl, 2-methyl-c-pentylaminosulfonyl, 3-methyl-c-pentylaminosulfonyl or the like may be mentioned.

A $C_{1-6}$ alkylsulfonyl group may be linear, branched or a $C_{3-6}$ cycloalkylsulfonyl group, and for example, methylsulfonyl, ethylsulfonyl, n-propylsulfonyl, i-propylsulfonyl, c-propylsulfonyl, n-butylsulfonyl, i-butylsulfonyl, s-butylsulfonyl, t-butylsulfonyl, c-butylsulfonyl, 1-methyl-c-propylsulfonyl, 2-methyl-c-propylsulfonyl, n-pentylsulfonyl, 1-methyl-n-butylsulfonyl, 2-methyl-n-butylsulfonyl, 3-methyl-n-butylsulfonyl, 1,1-dimethyl-n-propylsulfonyl, 1,2-dimethyl-n-propylsulfonyl, 2,2-dimethyl-n-propylsulfonyl, 1-ethyl-n-propylsulfonyl, c-pentylsulfonyl, 1-methyl-c-butylsulfonyl, 2-methyl-c-butylsulfonyl, 3-methyl-c-butylsulfonyl, 1,2-dimethyl-c-propylsulfonyl, 2,3-dimethyl-c-propylsulfonyl, 1-ethyl-c-propylsulfonyl, 2-ethyl-c-propylsulfonyl, n-hexylsulfonyl, 1-methyl-n-pentylsulfonyl, 2-methyl-n-pentylsulfonyl, 3-methyl-n-pentylsulfonyl, 4-methyl-n-pentylsulfonyl, 1,1-dimethyl-n-butylsulfonyl, 1,2-dimethyl-n-butylsulfonyl, 1,3-dimethyl-n-butylsulfonyl, 2,2-dimethyl-n-butylsulfonyl, 2,3-dimethyl-n-butylsulfonyl, 3,3-dimethyl-n-butylsulfonyl, 1-ethyl-n-butylsulfonyl, 2-ethyl-n-butylsulfonyl, 1,1,2-trimethyl-n-propylsulfonyl, 1,2,2-trimethyl-n-propylsulfonyl, 1-ethyl-1-methyl-n-propylsulfonyl, 1-ethyl-2-methyl-n-propylsulfonyl, c-hexylsulfonyl, 1-methyl-c-pentylsulfonyl, 2-methyl-c-pentylsulfonyl, 3-methyl-c-pentylsulfonyl, 1-ethyl-c-butylsulfonyl, 2-ethyl-c-butylsulfonyl, 3-ethyl-c-butylsulfonyl, 1,2-dimethyl-c-butylsulfonyl, 1,3-dimethyl-c-butylsulfonyl, 2,2-dimethyl-c-butylsulfonyl, 2,3-dimethyl-c-butylsulfonyl, 2,4-dimethyl-c-butylsulfonyl, 3,3-dimethyl-c-butylsulfonyl, 1-n-propyl-c-propylsulfonyl, 2-n-propyl-c-propylsulfonyl, 1-i-propyl-c-propylsulfonyl, 2-i-propyl-c-propylsulfonyl, 1,2,2-trimethyl-c-propylsulfonyl, 1,2,3-trimethyl-c-propylsulfonyl, 2,2,3-trimethyl-c-propylsulfonyl, 1-ethyl-2-methyl-c-propylsulfonyl, 2-ethyl-1-methyl-c-propylsulfonyl, 2-ethyl-2-methyl-c-propylsulfonyl, 2-ethyl-3-methyl-c-propylsulfonyl or the like may be mentioned.

A $C_{1-10}$ alkylsulfonyl group may be linear, branched or a $C_{3-10}$ cycloalkylsulfonyl group, and for example, in addition to those mentioned above, 1-methyl-1-ethyl-n-pentylsulfonyl, 1-heptylsulfonyl, 2-heptylsulfonyl, 1-ethyl-1,2-dimethyl-n-propylsulfonyl, 1-ethyl-2,2-dimethyl-n-propylsulfonyl, 1-octylsulfonyl, 3-octylsulfonyl, 4-methyl-3-n-heptylsulfonyl, 6-methyl-2-n-heptylsulfonyl, 2-propyl-1-n-n-heptylsulfonyl, 2,4,4-trimethyl-1-n-pentylsulfonyl, 1-nonylsulfonyl, 2-nonylsulfonyl, 2,6-dimethyl-4-n-heptylsulfonyl, 3-ethyl-2,2-dimethyl-3-n-pentylsulfonyl, 3,5,5-trimethyl-1-n-hexylsulfonyl, 1-decylsulfonyl, 2-decylsulfonyl, 4-decylsulfonyl, 3,7-dimethyl-1-n-octylsulfonyl, 3,7-dimethyl-3-n-octylsulfonyl, c-heptylsulfonyl, c-octylsulfonyl, 1-methyl-c-hexylsulfonyl, 2-methyl-c-hexylsulfonyl, 3-methyl-c-hexylsulfonyl, 1,2-dimethyl-c-hexylsulfonyl, 1-ethyl-c-hexylsulfonyl, 1-methyl-c-pentylsulfonyl, 2-methyl-c-pentylsulfonyl, 3-methyl-c-pentylsulfonyl or the like may be mentioned.

A $C_{2-14}$ aryl group may be a $C_{6-14}$ aryl group containing no hetero atoms as ring constituting atoms or a $C_{2-9}$ aromatic heterocyclic group, and a $C_{2-9}$ aromatic heterocyclic group may be a 5 to 7-membered $C_{2-6}$ heteromonocyclic group or 8 to 10-membered $C_{5-9}$ fused heterobicyclic group containing from 1 to 3 oxygen atoms, nitrogen atoms or sulfur atoms singly or in combination.

As a $C_{6-14}$ aryl group containing no hetero atoms, a phenyl group, a 1-indenyl group, a 2-indenyl group, a 3-indenyl group, a 4-indenyl group, a 5-indenyl group, a 6-indenyl group, a 7-indenyl group, an α-naphthyl group, a β-naphthyl group, a 1-tetrahydronaphthyl group, a 2-tetrahydronaphthyl group, a 5-tetrahydronaphthyl group, a 6-tetrahydronaphthyl group, an o-biphenylyl group, a m-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group or the like may be mentioned.

A 5 to 7-membered $C_{2-6}$ heteromonocyclic group may be a 2-thienyl group, a 3-thienyl group, a 2-furyl group, a 3-furyl group, a 2-pyranyl group, a 3-pyranyl group, a 4-pyranyl group, a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 3-isothiazolyl group, a 4-isothiazolyl group, a 5-isothiazolyl group, a 2-oxazolyl group, a 4-oxazolyl group, a 5-oxazolyl group, a 3-isoxazolyl group, a 4-isoxazolyl group, a 5-isoxazolyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group, a 4-pyridazinyl group, a 2-1,3,4-oxadiazolyl group, a 2-1,3,4-thiadiazolyl group, a 3-1,2,4-oxadiazolyl group, a 5-1,2,4-oxadiazolyl group, a 3-1,2,4-thiadiazolyl group, a 5-1,2,4-thiadiazolyl group, a 3-1,2,5-oxadiazolyl group, a 3-1,2,5-thiadiazolyl group or the like.

A 8 to 10-membered $C_{5-9}$ fused heterobicyclic group may be a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 4-isobenzofuranyl group, a 5-isobenzofuranyl group, a 2-benzothienyl group, a 3-benzothienyl group, a 4-benzothienyl group, a 5-benzothienyl group, a 6-benzothienyl group, a 7-benzothienyl group, a 1-isobenzothienyl group, a 4-isobenzothienyl group, a 5-isobenzothienyl group, a 2-chromenyl group, a 3-chromenyl group, a 4-chromenyl group, a 5-chromenyl group, a 6-chromenyl group, a 7-chromenyl group, a 8-chromenyl group, a 1-indolizinyl group, a 2-indolizinyl group, a 3-indolizinyl group, a 5-indolizinyl group, a 6-indolizinyl group, a 7-indolizinyl group, a 8-indolizinyl group, a 1-isoindolyl group, a 2-isoindolyl group, a 4-isoindolyl group, a 5-isoindolyl group, a 1-indolyl group, a 2-indolyl group, a 3-indolyl group, a 4-indolyl group, a 5-indolyl group, a 6-indolyl group, a 7-indolyl group, a 1-indazolyl group, a 2-indazolyl group, a 3-indazolyl group, a 4-indazolyl group, a 5-indazolyl group, a 6-indazolyl group, a 7-indazolyl group, a 1-purinyl group, a 2-purinyl group, a 3-purinyl group, a 6-purinyl group, a 7-purinyl group, a 8-purinyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 1-phthalazinyl group, a 5-phthalazinyl group, a 6-phthalazinyl group, a 1-2,7-naphthyridinyl group, a 3-2,7-naphthyridinyl group, a 4-2,7-naphthyridinyl group, a 1-2,6-naphthyridinyl group, a 3-2,6-naphthyridinyl group, a 4-2,6-naphthyridinyl group, a 2-1,8-naphthyridinyl group, a 3-1,8-naphthyridinyl group, a 4-1,8-naphthyridinyl group, a 2-1,7-naphthyridinyl group, a 3-1,7-naphthyridinyl group, a 4-1,7-naphthyridinyl group, a 5-1,7-naphthyridinyl group, a 6-1,7-naphthyridinyl group, a 8-1,7-naphthyridinyl group, 2-1,6-naphthyridinyl group, a 3-1,6-naphthyridinyl group, a 4-1,6-naphthyridinyl group, a 5-1,6-naphthyridinyl group, a 7-1,6-naphthyridinyl group, a 8-1,6-naphthyridinyl group, a 2-1,5-naphthyridinyl group, a 3-1,5-naphthyridinyl group, a 4-1,5-naphthyridinyl group, a 6-1,5-naphthyridinyl group, a 7-1,5-naphthyridinyl group, a 8-1,5-naphthyridinyl group, a 2-quinoxalinyl group, a 5-quinoxalinyl group, a 6-quinoxalinyl group, a 2-quinazolinyl group, a 4-quinazolinyl group, a 5-quinazolinyl group, a 6-quinazolinyl group, a 7-quinazolinyl group, a 8-quinazolinyl group, a 3-cinnolinyl group, a 4-cinnolinyl group, a 5-cinnolinyl group, a 6-cinnolinyl group, a 7-cinnolinyl group, a 8-cinnolinyl group, a 2-pteridinyl group, a 4-pteridinyl group, a 6-pteridinyl group, a 7-pteridinyl group or the like.

A $C_{2-14}$ aryloxy group may be a $C_{6-14}$ aryloxy group containing no hetero atoms as ring constituting atoms or a $C_{2-9}$ aromatic heterocyclyloxy group, and a $C_{2-9}$ aromatic heterocyclyloxy group may be a 5 to 7-membered $C_{2-6}$ monocyclic heterocyclyloxy group or 8 to 10-membered $C_{5-9}$ fused bicyclic heterocyclyloxy group containing from 1 to 3 oxygen atoms, nitrogen atoms or sulfur atoms singly or in combination.

As a $C_{6-14}$ aryloxy group containing no hetero atoms, a phenyloxy group, a 1-indenyloxy group, a 2-indenyloxy group, a 3-indenyloxy group, a 4-indenyloxy group, a 5-indenyloxy group, a 6-indenyloxy group, a 7-indenyloxy group, an α-naphthyloxy group, a β-naphthyloxy group, a 1-tetrahydronaphthyloxy group, a 2-tetrahydronaphthyloxy group, a 5-tetrahydronaphthyloxy group, a 6-tetrahydronaphthyloxy group, an o-biphenylyloxy group, a m-biphenylyloxy group, a p-biphenylyloxy group, a 1-anthryloxy group, a 2-anthryloxy group, a 9-anthryloxy group, a 1-phenanthryloxy group, a 2-phenanthryloxy group, a 3-phenanthryloxy group, a 4-phenanthryloxy group, a 9-phenanthryloxy group or the like may be mentioned.

A 5 to 7-membered $C_{2-6}$ monocyclic heterocyclyloxy group may be a 2-thienyloxy group, a 3-thienyloxy group, a 2-furyloxy group, a 3-furyloxy group, a 2-pyranyloxy group, a 3-pyranyloxy group, a 4-pyranyloxy group, a 1-pyrrolyloxy group, a 2-pyrrolyloxy group, a 3-pyrrolyloxy group, a 1-imidazolyloxy group, a 2-imidazolyloxy group, a 4-imidazolyloxy group, a 1-pyrazolyloxy group, a 3-pyrazolyloxy group, a 4-pyrazolyloxy group, a 2-thiazolyloxy group, a 4-thiazolyloxy group, a 5-thiazolyloxy group, a 3-isothiazolyloxy group, a 4-isothiazolyloxy group, a 5-isothiazolyloxy group, a 2-oxazolyloxy group, a 4-oxazolyloxy group, a 5-oxazolyloxy group, a 3-isoxazolyloxy group, a 4-isoxazolyloxy group, a 5-isoxazolyloxy group, a 2-pyridyloxy group, a 3-pyridyloxy group, a 4-pyridyloxy group, a 2-pyrazinyloxy group, a 2-pyrimidinyloxy group, a 4-pyrimidinyloxy group, a 5-pyrimidinyloxy group, a 3-pyridazinyloxy group, a 4-pyridazinyloxy group, a 2-1,3,4-oxadiazolyloxy group, a 2-1,3,4-thiadiazolyloxy group, a 3-1,2,4-oxadiazolyloxy group, a 5-1,2,4-oxadiazolyloxy group, a 3-1,2,4-thiadiazolyloxy group, a 5-1,2,4-thiadiazolyloxy group, a 3-1,2,5-oxadiazolyloxy group, a 3-1,2,5-thiadiazolyloxy group or the like.

A 8 to 10-membered $C_{5-9}$ fused bicyclic heterocyclyloxy group may be a 2-benzofuranyloxy group, a 3-benzofuranyloxy group, a 4-benzofuranyloxy group, a 5-benzofuranyloxy group, a 6-benzofuranyloxy group, a 7-benzofuranyloxy group, a 1-isobenzofuranyloxy group, a 4-isobenzofuranyloxy group, a 5-isobenzofuranyloxy group, a 2-benzothienyloxy group, a 3-benzothienyloxy group, a 4-benzothienyloxy group, a 5-benzothienyloxy group, a 6-benzothienyloxy group, a 7-benzothienyloxy group, a 1-isobenzothienyloxy group, a 4-isobenzothienyloxy group, a 5-isobenzothienyloxy group, a 2-chromenyloxy group, a 3-chromenyloxy group, a 4-chromenyloxy group, a 5-chromenyloxy group, a 6-chromenyloxy group, a 7-chromenyloxy group, a 8-chromenyloxy group, a 1-indolizinyloxy group, a 2-indolizinyloxy group, a 3-indolizinyloxy group, a 5-indolizinyloxy group, a 6-indolizinyloxy group, a 7-indolizinyloxy group, a 8-indolizinyloxy group, a 1-isoindolyloxy group, a 2-isoindolyloxy group, a 4-isoindolyloxy group, a 5-isoindolyloxy group, a 1-indolyloxy group, a 2-indolyloxy group, a 3-indolyloxy group, a 4-indolyloxy group, a 5-indolyloxy group, a 6-indolyloxy group, a 7-indolyloxy group, a 1-indazolyloxy group, a 2-indazolyloxy group, a 3-indazolyloxy group, a 4-indazolyloxy group, a 5-indazolyloxy group, a 6-indazolyloxy group, a 7-indazolyloxy group, a 1-purinyloxy group, a 2-purinyloxy group, a 3-purinyloxy group, a 6-purinyloxy group, a 7-purinyloxy group, a 8-purinyloxy group, a 2-quinolyloxy group, a 3-quinolyloxy group, a 4-quinolyloxy group, a 5-quinolyloxy group, a 6-quinolyloxy group, a 7-quinolyloxy group, a 8-quinolyloxy group, a 1-isoquinolyloxy group, a 3-isoquinolyloxy group, a 4-isoquinolyloxy group, a 5-isoquinolyloxy group, a 6-isoquinolyloxy group, a 7-isoquinolyloxy group, a 8-isoquinolyloxy group, a 1-phthalazinyloxy group, a 5-phthalazinyloxy group, a 6-phthalazinyloxy group, a 1-2,7-naphthyridinyloxy group, a 3-2,7-naphthyridinyloxy group, a 4-2,7-naphthyridinyloxy group, a 1-2,6-naphthyridinyloxy group, a 3-2,6-naphthyridinyloxy group, a 4-2,6-naphthyridinyloxy group, a 2-1,8-naphthyridinyloxy group, a 3-1,8-naphthyridinyloxy group, a 4-1,8-naphthyridinyloxy group, a 2-1,7-naphthyridinyloxy group, a 3-1,7-naphthyridinyloxy group, a 4-1,7-naphthyridinyloxy group, a 5-1,7-naphthyridinyloxy group, a 6-1,7-naphthyridinyloxy group, a 8-1,7-naphthyridinyloxy group, 2-1,6-naphthyridinyloxy group, a 3-1,6-naphthyridinyloxy group, a 4-1,6-naphthyridinyloxy group, a 5-1,6-naphthyridinyloxy group, a 7-1,6-naphthyridinyloxy group, a 8-1,6-naphthyridinyloxy group, a 2-1,5-naphthyridinyloxy group, a 3-1,5-naphthyridinyloxy group, a 4-1,5-naphthyridinyloxy group, a 6-1,5-naphthyridinyloxy group, a 7-1,5-naphthyridinyloxy group, a 8-1,5-naphthyridinyloxy group, a 2-quinoxalinyloxy group, a 5-quinoxalinyloxy group, a 6-quinoxalinyloxy group, a 2-quinazolinyloxy group, a 4-quinazolinyloxy group, a 5-quinazolinyloxy group, a 6-quinazolinyloxy group, a 7-quinazolinyloxy group, a 8-quinazolinyloxy group, a 3-cinnolinyloxy group, a 4-cinnolinyloxy group, a 5-cinnolinyloxy group, a 6-cinnolinyloxy group, a 7-cinnolinyloxy group, a 8-cinnolinyloxy group, a 2-pteridinyloxy group, a 4-pteridinyloxy group, a 6-pteridinyloxy group, a 7-pteridinyloxy group or the like.

The protecting group in a protected hydroxyl group, a protected thiol group or a protected amino group may be a $C_{1-4}$ alkoxymethyl group (such as MOM: methoxymethyl, MEM: 2-methoxyethoxymethyl, ethoxymethyl, n-propoxymethyl, i-propoxymethyl, n-butoxymethyl, iBM: isobutyloxymethyl, BUM: t-butoxymethyl, POM: pivaloyloxymethyl, SEM: trimethylsilylethoxymethyl and the like, preferably a $C_{1-2}$ alkoxymethyl or the like), an aryloxymethyl (such as BOM: benzyloxymethyl, PMBM: p-methoxybenzyloxymethyl, p-AOM: p-anisyloxymethyl or the like, preferably benzyloxymethyl or the like), a $C_{1-4}$ alkylaminomethyl group (such as dimethylaminomethyl or the like), a substituted acetamidomethyl group (such as Acm: acetamidomethyl, Tacm: trimethylacetamidomethyl or the like), a substituted thiomethyl group (such as MTM: methylthiomethyl, PTM: phenylthiomethyl, Btm: benzylthiomethyl or the like), a carboxyl group, a $C_{1-7}$ acyl group (such as formyl, acetyl, fluoroacetyl, difluoroacetyl, trifluoroacetyl, chloroacetyl, dichloroacetyl, trichloroacetyl, propionyl, Pv: pivaloyl, tigloyl or the like), an arylcarbonyl group (such as benzoyl, benzoylformyl, benzoylpropionyl, phenylpropionyl or the like), a $C_{1-4}$ alkoxycarbonyl group (such as methoxycarbonyl, ethoxycarbonyl, n-propoxycarbonyl, i-propoxycarbonyl, n-butoxycarbonyl, i-butoxycarbonyl, BOC: t-butoxycarbonyl, AOC: t-amyloxycarbonyl, VOC: vinyloxycarbonyl, AOC: allyloxycarbonyl, Teoc: 2-(trimethylsilyl)ethoxycarbonyl, Troc: 2,2,2-trichloroethoxycarbonyl or the like, preferably BOC or the like), an aryloxycarbonyl group (such as Z: benzyloxycarbonyl, p-nitrobenzyloxycarbonyl, MOZ: p-methoxybenzyloxycarbonyl or the like), a $C_{1-4}$ alkylaminocarbonyl group (such as methylcarbamoyl, Ec: ethylcarbamoyl, n-propylcarbamoyl or the like), an arylaminocarbonyl group (such as phenylcarbamoyl or the like), a trialkylsilyl group (such as TMS: trimethylsilyl, TES: triethylsilyl, TIPS: triisopropylsilyl, DEIPS: diethylisopropylsilyl, DMIPS: dimethylisopropylsilyl, DTBMS: di-t-butylmethylsilyl, IPDMS: isopropyldimethylsilyl, TBDMS: t-butyldimethylsilyl, TDS: thexyldimethylsilyl or the like, preferably t-butyldimethylsilyl or the like), a trialkylarylsilyl group (such as DPMS: diphenylmethylsilyl, TBDPS: t-butyldiphenylsilyl, TBMPS: t-butyldimethoxyphenylsilyl, TPS: triphenylsilyl or the like), an alkylsulfonyl group, (such as Ms: methanesulfonyl, ethanesulfonyl or the like) or an arylsulfonyl group (such as benzenesulfonyl, Ts: p-toluenesulfonyl, p-chlorobenzenesulfonyl, MBS: p-methoxybenzenesulfonyl, m-nitrobenzenesulfonyl, iMds: 2,6-dimethoxy-4-methylbenzenesulfonyl, Mds: 2,6-dimethyl-4-methoxybenzenesulfonyl, Mtb: 2,4,6-trimethoxybenzenesulfonyl, Mte: 2,3,5,6-tetramethyl-4-methoxybenzenesulfonyl, Mtr: 2,3,6-trimethyl-4-methoxybenzenesulfonyl, Mts: 2,4,6-trimethylbenzenesulfonyl, Pme: pentamethylbenzenesulfonyl or the like).

A C$_{2-9}$ heterocyclyl group may be a heteromonocyclic or fused heterobicyclic group consisting of at least one atom optionally selected from nitrogen atoms, oxygen atoms and sulfur atoms and from 2 to 9 carbon atoms, and specifically mentioned are:

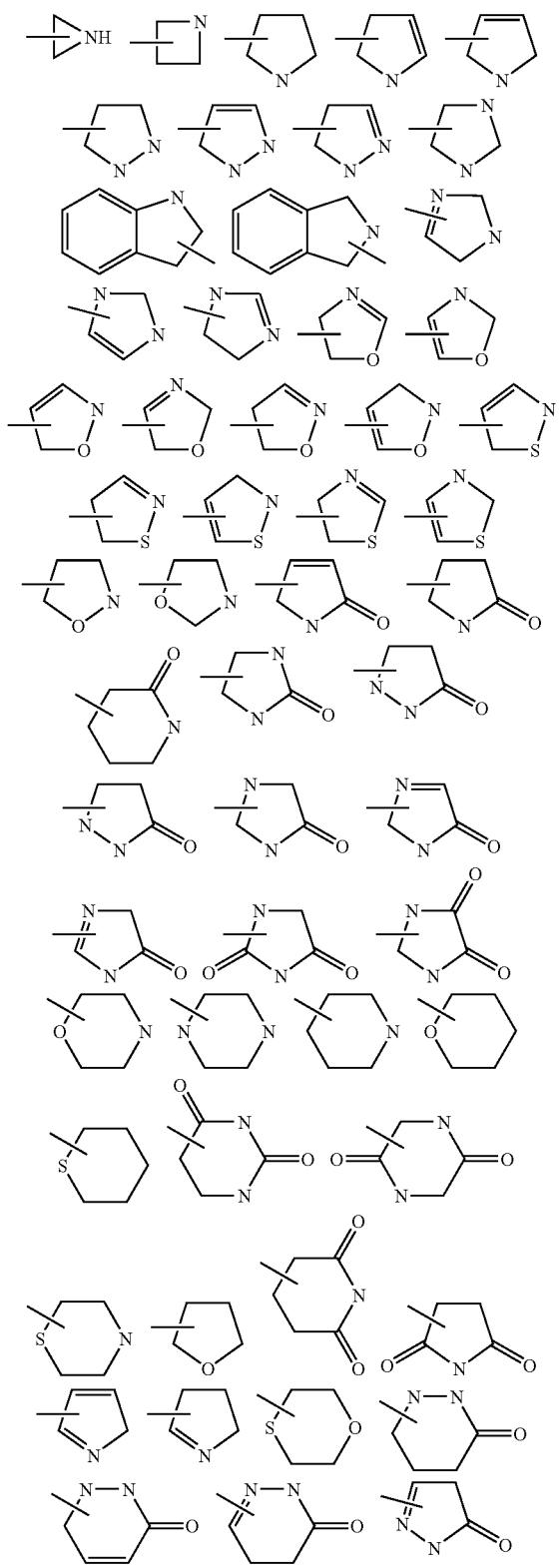

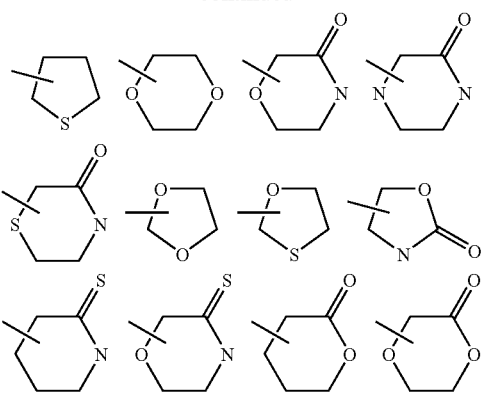

A nitrogen-containing C$_{2-9}$ heterocyclyl group may be, among those given above, a heteromonocyclic or fused heterobicyclic group which contains least one nitrogen atom, may contain at least one atom optionally selected from oxygen atoms and sulfur atoms and contains from 2 to 9 carbon atoms, and specifically mentioned are:

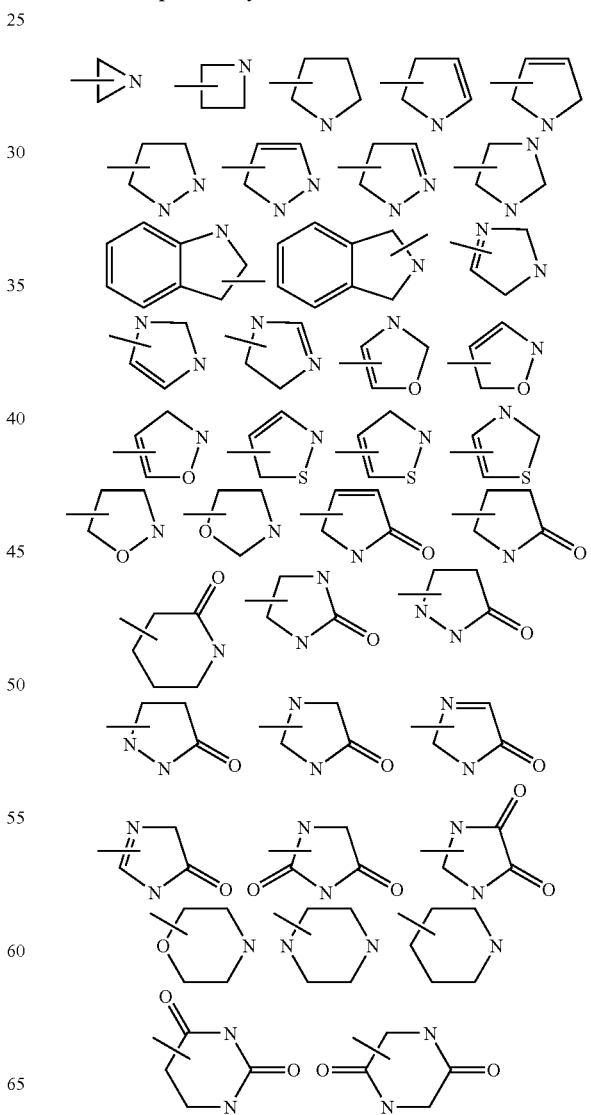

As a $C_{3-7}$ carbocyclyl group, specifically mentioned are:

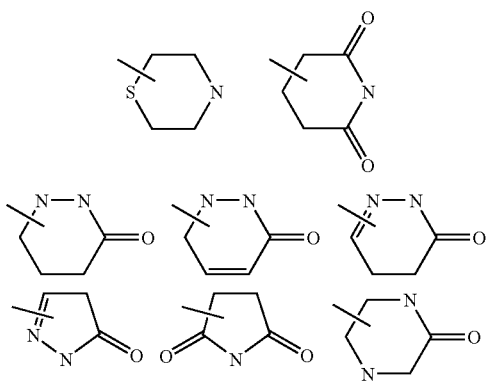

Preferred specific examples of $L^1$-X are the following structural formulae:

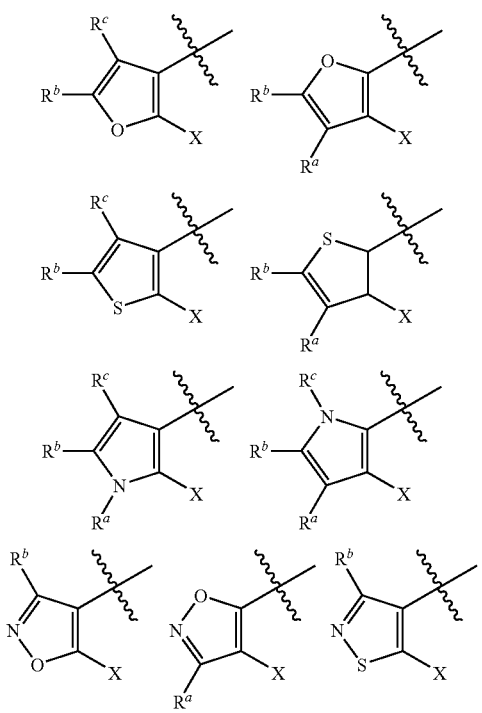

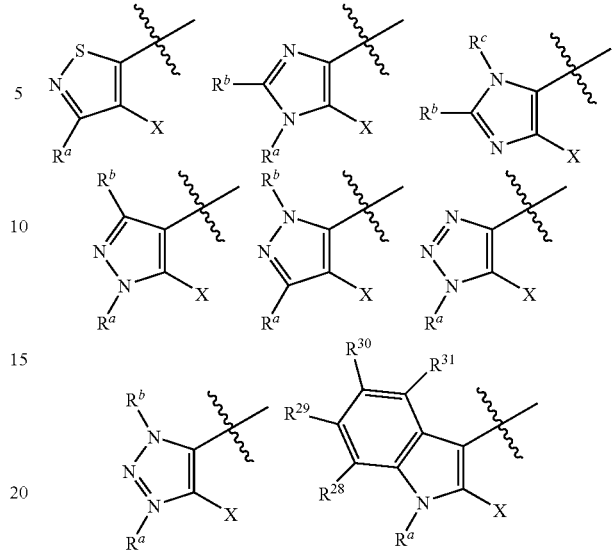

Particularly preferred are the following structural formulae:

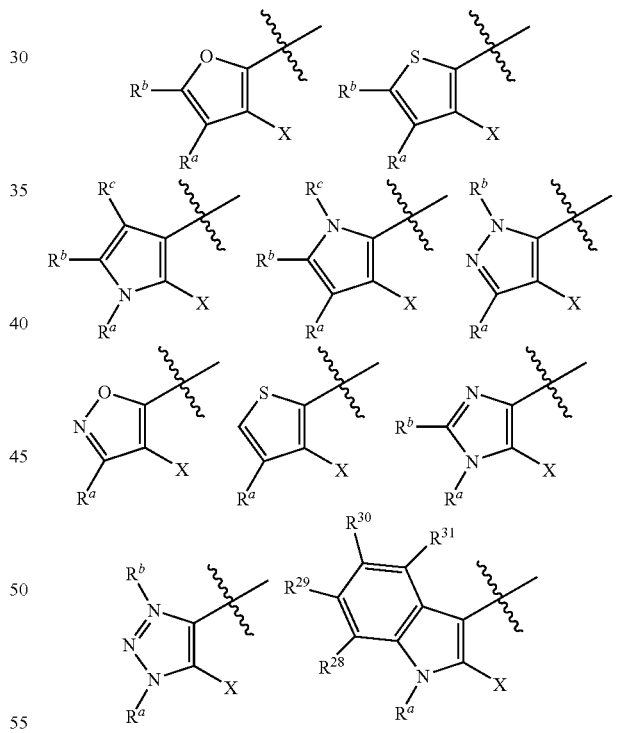

Preferred specific examples of $R^a$ in the structural formulae are $C_{2-14}$ aryl groups optionally substituted with one or more of the following substituents.

Substituents: halogen atoms, $C_{1-6}$ alkyl groups (the $C_{1-6}$ alkyl groups may be substituted with one or more halogen atoms) and $C_{1-6}$ alkoxy groups (the $C_{1-6}$ alkoxy groups may be substituted with one or more halogen atoms).

A particularly preferred specific example is a phenyl group optionally substituted with one or more of the following substituents.

Substituents: halogen atoms, $C_{1-6}$ alkyl groups (the $C_{1-6}$ alkyl groups may be substituted with one or more halogen atoms) and $C_{1-6}$ alkoxy groups (the $C_{1-6}$ alkoxy groups may be substituted with one or more halogen atoms).

Preferred specific examples of $R^b$ and $R^c$ in the structural formulae are a hydrogen atom, a $C_{1-6}$ alkyl group (the $C_{1-6}$ alkyl group may be substituted with one or more halogen atoms) and a $C_{1-6}$ alkoxy group (the $C_{1-6}$ alkoxy group may be substituted with one or more halogen atoms).

Particularly preferred specific examples are a hydrogen atom, a $C_{1-3}$ alkyl group (the $C_{1-3}$ alkyl group may be substituted with one or more halogen atoms) and a $C_{1-3}$ alkoxy group (the $C_{1-3}$ alkoxy group may be substituted with one or more halogen atoms).

Preferred specific examples of $R^{28}$, $R^{29}$, $R^{30}$ and $R^{31}$ in the structural formulae are a hydrogen atom, a $C_{1-6}$ alkyl group (the $C_{1-6}$ alkyl group may be substituted with one or more halogen atoms) and a $C_{1-6}$ alkoxy group (the $C_{1-6}$ alkoxy group may be substituted with one or more halogen atoms), a carboxyl group, a carbamoyl group, a nitro group, a cyano group, a halogen atom, a hydroxyl group and an amino group.

Particularly preferred specific examples are a hydrogen atom, a $C_{1-3}$ alkyl group (the $C_{1-3}$ alkyl group may be substituted with one or more halogen atoms) and a $C_{1-3}$ alkoxy group (the $C_{1-3}$ alkoxy group may be substituted with one or more halogen atoms).

Preferred specific examples of X are OH and SH, and a particularly preferred specific example is OH.

Preferred specific examples of Y are an oxygen atom, a sulfur atom and NH, and a particularly preferred specific example is a sulfur atom.

Preferred specific examples of $L^2$ are a single bond, an oxygen atom, a sulfur atom and NH, and a particularly preferred specific example is a single bond.

Preferred specific examples of $L^3$ are a single bond and NH, and a particularly preferred specific example is a single bond.

Preferred specific examples of $R^1$ are a hydrogen atom and a $C_{1-10}$ alkyl group (the $C_{1-10}$ alkyl group may be substituted with one or more halogen atoms). Particularly preferred specific examples are a hydrogen atom and a $C_{1-3}$ alkyl group (the $C_{1-3}$ alkyl group may be substituted with one or more halogen atoms). More particularly preferred specific examples are a hydrogen atom, a methyl group, an ethyl group and a trifluoromethyl group.

Preferred specific examples of $R^2$ are a hydrogen atom and a $C_{1-10}$ alkyl group (the $C_{1-10}$ alkyl group may be substituted with one or more halogen atoms). A particularly preferred specific example is a hydrogen atom.

A preferred specific example of $R^3$ is a $C_{2-9}$ nitrogen-containing heterocyclyl group substituted with one or more substituents selected from the following substituent set A.

Substituent set A: hydrogen atoms, hydroxyl groups, carboxyl groups, sulfo groups, carbamoyl groups, sulfamoyl groups, tetrazole groups, phosphono groups, $CH_2CO_2H$, $COCO_2H$, $-SO_2R^{25}$ and $-COR^{25}$ (wherein $R^{25}$ means a $C_{1-10}$ alkoxy group, a $C_{2-9}$ heterocyclyl group or $NR^{26}R^{27}$ (wherein each of $R^{26}$ and $R^{27}$ independently means a hydrogen atom, a $C_{1-10}$ alkyl group (the $C_{1-10}$ alkyl group may optionally substituted with one or more $C_{2-14}$ aryl groups))).

A particularly preferred specific example is a $C_{2-9}$ nitrogen-containing heterocyclyl group represented by the formula (IV) substituted with one or more substituents selected from the following substituent set B.

Substituent set B: hydrogen atoms, hydroxyl groups, carboxyl groups, sulfo groups, carbamoyl groups, sulfamoyl groups, tetrazole groups, phosphono groups, $CH_2CO_2H$ and $COCO_2H$.

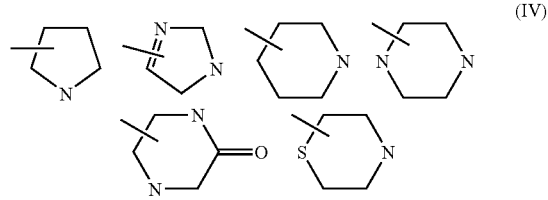

(IV)

Favorable compounds as the thrombopoietin receptor activator, the preventive, therapeutic or improving agent for diseases against which activation of the thrombopoietin receptor is effective and the platelet increasing agent of the present invention are as follows.

(1) Compounds represented by the formula (V), which are compounds represented by the formula (I) wherein A is $CR^a$, B is $CR^b$, D=E means, as a whole, a sulfur atom, $L^2$ is a single bond, and $L^3$ is a single bond, tautomers, prodrugs or pharmaceutically acceptable salts of the compounds or solvates thereof.

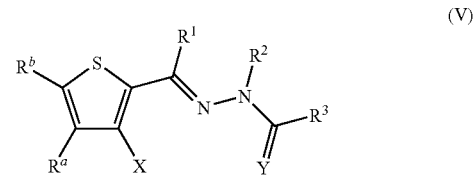

(V)

(2) Compounds represented by the formula (VI), which are compounds represented by the formula (I) wherein A=B, as a whole, means $NR^a$, D is a nitrogen atom, E is $CR^b$, $L^2$ is a single bond, and $L^3$ is a single bond, tautomers, prodrugs or pharmaceutically acceptable salts of the compounds or solvates thereof.

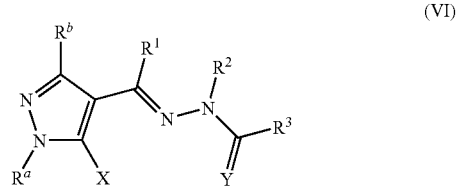

(VI)

(3) Compounds represented by the formula (VII), which are compounds represented by the formula (I) wherein A is $CR^a$, B is a nitrogen atom, D=E, as a whole, means $NR^b$, $L^2$ is a single bond, and $L^3$ is a single bond, tautomers, prodrugs or pharmaceutically acceptable salts of the compounds or solvates thereof.

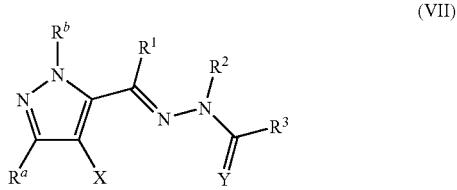

(VII)

(4) The compounds according to (1), (2) or (3), wherein $R^2$ is a hydrogen atom, tautomers, prodrugs or pharmaceutically acceptable salts of the compounds or solvates thereof.

(5) The compounds according to (4), wherein Y is a sulfur atom, tautomers, prodrugs or pharmaceutically acceptable salts of the compounds or solvates thereof.

(6) The compounds according to (5), wherein X is OH, tautomers, prodrugs or pharmaceutically acceptable salts of the compounds or solvates thereof.

(7) The compounds according to (6), wherein $R^1$ is a hydrogen atom or a $C_{1-3}$ alkyl group (the $C_{1-3}$ alkyl group may be substituted with one or more halogen atoms), tautomers, prodrugs or pharmaceutically acceptable salts of the compounds or solvates thereof.

(8) The compounds according to (7), wherein $R^b$ is a hydrogen atom or a $C_{1-3}$ alkyl group (the $C_{1-3}$ alkyl group may be substituted with one or more halogen atoms), tautomers, prodrugs or pharmaceutically acceptable salts of the compounds or solvates thereof.

(9) The compounds according to (8), wherein $R^a$ is a phenyl group optionally substituted with one or more of the following substituents, tautomers, prodrugs or pharmaceutically acceptable salts of the compounds or solvates thereof.
Substituents: t-butyl groups, methyl groups, methoxy groups, trifluoromethyl groups, trifluoromethoxy groups, chlorine atoms, bromine atoms and fluorine atoms.

(10) The compounds according to (9), wherein $R^3$ is a $C_{2-9}$ heterocyclyl group substituted with one or more substituents selected from the following substituent set B, tautomers, prodrugs or pharmaceutically acceptable salts of the compounds or solvates thereof.
Substituent set B: hydrogen atoms, hydroxyl groups, carboxyl groups, sulfo groups, carbamoyl groups, sulfamoyl groups, tetrazole groups, phosphono groups, $CH_2CO_2H$ and $COCO_2H$.

(11) The compounds according to (9), wherein $R^3$ is any of the structures represented by the formula (VIII) which is substituted with one or more substituents selected from the following substituent set B, tautomers, prodrugs or pharmaceutically acceptable salts of the compounds or solvates thereof.
Substituent set B: hydrogen atoms, hydroxyl groups, carboxyl groups, sulfo groups, carbamoyl groups, sulfamoyl groups, tetrazole groups, phosphono groups, $CHCO_2H$ and $COCO_2H$.

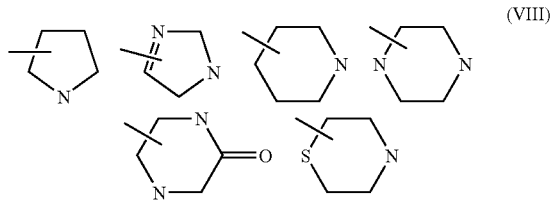

(VIII)

(12) The compounds according to (9), wherein $R^3$ is a piperidine or piperazine group substituted with one or more substituents selected from the following substituent set B, tautomers, prodrugs or pharmaceutically acceptable salts of the compounds or solvates thereof.
Substituent set B: hydrogen atoms, hydroxyl groups, carboxyl groups, sulfo groups, carbamoyl groups, sulfamoyl groups, tetrazole groups, phosphono groups, $CH_2CO_2H$ and $COCO_2H$.

(13) Compounds represented by the formula (IX), which are compounds represented by the formula (I) wherein A=B, as a whole, means $NR^a$, D is $CR^b$, E is $CR^c$, $L^2$ is a single bond, and $L^3$ is a single bond, tautomers, prodrugs or pharmaceutically acceptable salts of the compounds or solvates thereof.

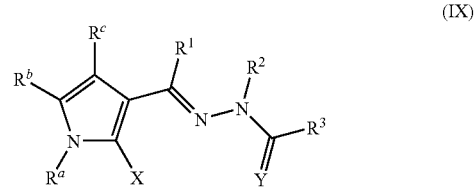

(IX)

(14) Compounds represented by the formula (X), which are compounds represented by the formula (I) wherein A is $CR^a$, B is $CR^b$, D=E, as a whole, means $NR^c$, $L^2$ is a single bond, and $L^3$ is a single bond, tautomers, prodrugs or pharmaceutically acceptable salts of the compounds or solvates thereof.

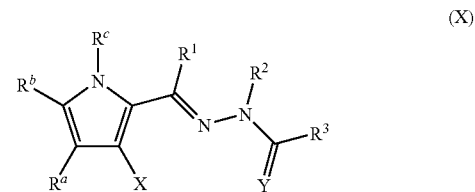

(X)

(15) The compounds according to (13) or (14), wherein $R^2$ is a hydrogen, tautomers, prodrugs or pharmaceutically acceptable salts of the compounds or solvates thereof.

(16) The compounds according to (15), wherein Y is a sulfur atom, tautomers, prodrugs or pharmaceutically acceptable salts of the compounds or solvates thereof.

(17) The compounds according to (16), wherein X is OH, tautomers, prodrugs or pharmaceutically acceptable salts of the compounds or solvates thereof.

(18) The compounds according to (17), wherein $R^1$ is a hydrogen atom or a $C_{1-3}$ alkyl group (the $C_{1-3}$ alkyl group may be substituted with one or more halogen atoms), tautomers, prodrugs or pharmaceutically acceptable salts of the compounds or solvates thereof.

(19) The compounds according to (18), wherein each of $R^b$ and $R^c$ is independently a hydrogen atom or a $C_{1-3}$ alkyl group (the $C_{1-3}$ alkyl group may be substituted with one or more halogen atoms), tautomers, prodrugs or pharmaceutically acceptable salts of the compounds or solvates thereof.

(20) The compounds according to (19), wherein $R^a$ is a phenyl group optionally substituted with one or more of the following substituents, tautomers, prodrugs or pharmaceutically acceptable salts of the compounds or solvates thereof.
Substituents: t-butyl groups, methyl groups, methoxy groups, trifluoromethyl groups, trifluoromethoxy groups, chlorine atoms, bromine atoms and fluorine atoms.

(21) The compounds according to (20), wherein $R^3$ is a $C_{2-9}$ nitrogen-containing heterocyclyl group substituted with one or more substituents selected from the substituent set B, tautomers, prodrugs or pharmaceutically acceptable salts of the compounds or solvates thereof.
Substituent set B: hydrogen atoms, hydroxyl groups, carboxyl groups, sulfo groups, carbamoyl groups, sulfamoyl groups, tetrazole groups, phosphono groups, $CH_2CO_2H$ and $COCO_2H$.

(22) The compounds according to (20), wherein $R^3$ is any of the structures represented by the formula (VIII) which is substituted with one or more substituents selected from the following substituent set B, tautomers, prodrugs or pharmaceutically acceptable salts of the compounds or solvates thereof.
Substituent set B: hydrogen atoms, hydroxyl groups, carboxyl groups, sulfo groups, carbamoyl groups, sulfamoyl groups, tetrazole groups, phosphono groups, $CH_2CO_2H$ and $COCO_2H$.

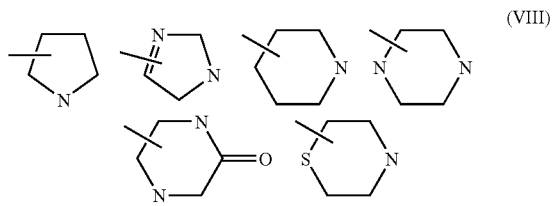

(VIII)

(23) The compounds according to (20), wherein $R^3$ is a piperidine or piperazine group substituted with one or more substituents selected from the following substituent set B, tautomers, prodrugs or pharmaceutically acceptable salts of the compounds or solvates thereof.
Substituent set B: hydrogen atoms, hydroxyl groups, carboxyl groups, sulfo groups, carbamoyl groups, sulfamoyl groups, tetrazole groups, phosphono groups, $CH_2CO_2H$ and $COCO_2H$.

(24) Compounds represented by the formula (XI), which are compounds represented by the formula (I) wherein A=B, as a whole, means $NR^a$, a phenyl substituted with $R^{28}$, $R^{29}$, $R^{30}$ and $R^{31}$ is fused at D and E, $L^2$ is a single bond, and $L^3$ is a single bond, tautomers, prodrugs or pharmaceutically acceptable salts of the compounds or solvates thereof.

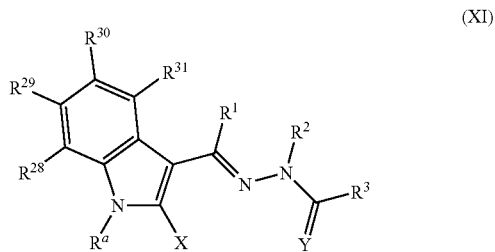

(XI)

(25) The compounds according (24), wherein $R^2$ is a hydrogen, tautomers, prodrugs or pharmaceutically acceptable salts of the compounds or solvates thereof.

(26) The compounds according to (25), wherein Y is a sulfur atom, tautomers, prodrugs or pharmaceutically acceptable salts of the compounds or solvates thereof.

(27) The compounds according to (26), wherein X is OH, tautomers, prodrugs or pharmaceutically acceptable salts of the compounds or solvates thereof.

(28) The compounds according to (27), wherein $R^1$ is a hydrogen atom or a $C_{1-3}$ alkyl group (the $C_{1-3}$ alkyl group may be substituted with one or more halogen atoms), tautomers, prodrugs or pharmaceutically acceptable salts of the compounds or solvates thereof.

(29) The compounds according to (28), wherein each of $R^{28}$, $R^{29}$, $R^{30}$ and $R^{31}$ is independently a hydrogen atom or a $C_{1-3}$ alkyl group (the $C_{1-3}$ alkyl group may be substituted with one or more halogen atoms), tautomers, prodrugs or pharmaceutically acceptable salts of the compounds or solvates thereof.

(30) The compounds according to (29), wherein $R^a$ is a phenyl group optionally substituted with one or more of the following substituents, tautomers, prodrugs or pharmaceutically acceptable salts of the compounds or solvates thereof.
Substituents: t-butyl groups, methyl groups, methoxy groups, trifluoromethyl groups, trifluoromethoxy groups, chlorine atoms, bromine atoms and fluorine atoms.

(31) The compounds according to (30), wherein $R^3$ is a $C_{2-9}$ nitrogen-containing heterocyclyl group substituted with one or more substituents selected from the substituent set B, tautomers, prodrugs or pharmaceutically acceptable salts of the compounds or solvates thereof.
Substituent set B: hydrogen atoms, hydroxyl groups, carboxyl groups, sulfo groups, carbamoyl groups, sulfamoyl groups, tetrazole groups, phosphono groups, $CH_2CO_2H$ and $COCO_2H$.

(32) The compounds according to (30), wherein $R^3$ is any of the structures represented by the formula (VIII) which is substituted with one or more substituents selected from the following substituent set B, tautomers, prodrugs or pharmaceutically acceptable salts of the compounds or solvates thereof.
Substituent set B: hydrogen atoms, hydroxyl groups, carboxyl groups, sulfo groups, carbamoyl groups, sulfamoyl groups, tetrazole groups, phosphono groups, $CH_2CO_2H$ and $COCO_2H$.

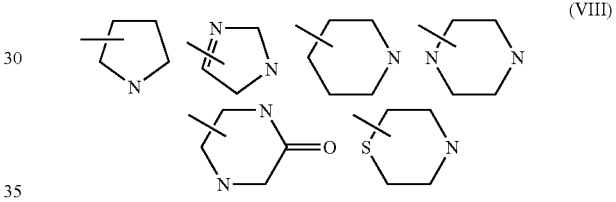

(VIII)

(33) The compounds according to (30), wherein $R^3$ is a piperidine or piperazine group substituted with one or more substituents selected from the following substituent set B, tautomers, prodrugs or pharmaceutically acceptable salts of the compounds or solvates thereof.
Substituent set B: hydrogen atoms, hydroxyl groups, carboxyl groups, sulfo groups, carbamoyl groups, sulfamoyl groups, tetrazole groups, phosphono groups, $CH_2CO_2H$ and $COCO_2H$.

(34) Compounds represented by the formula (V), wherein $R^2$ is a hydrogen atom, $R^b$ is a methyl group, X is OH, Y is a sulfur atom, and $R^a$, $R^1$ and $R^3$ are any of the following combinations shown in Table 1, tautomers, prodrugs or pharmaceutically acceptable salts of the compounds or solvates thereof. The symbols in Table 1 denote the following substituents.

TABLE 1

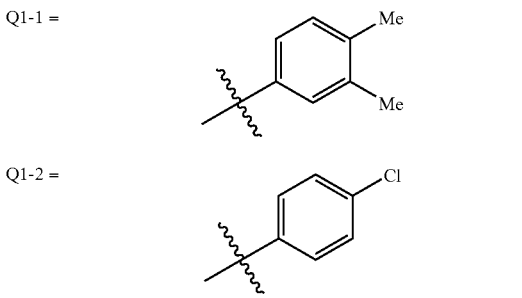

Q1-1 =

Q1-2 =

TABLE 1-continued
Q1-3 = 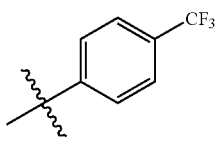
Q1-4 = 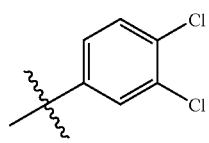
Q1-5 = 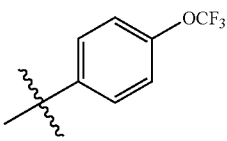
Q1-6 = 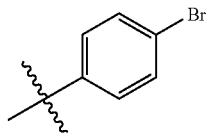
Q1-7 = 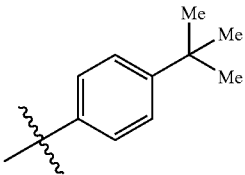
Q1-8 = 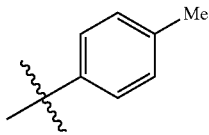
Q3-1 = 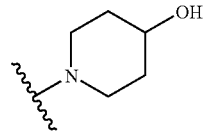
Q3-2 = 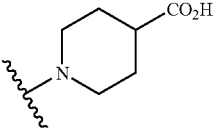
Q3-3 = 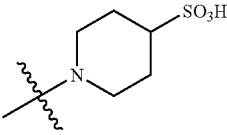
Q3-4 = 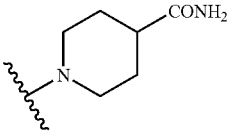
TABLE 1-continued
Q3-5 = 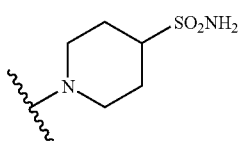
Q3-6 = 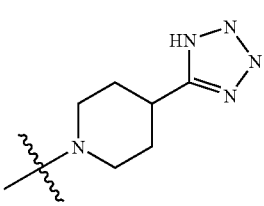
Q3-7 = 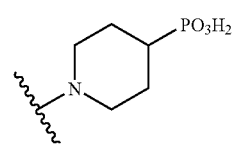
Q3-8 = 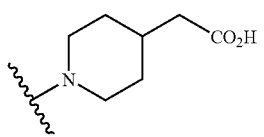
Q3-9 = 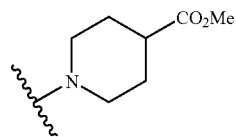
Q3-10 = 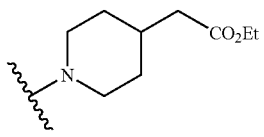
Q3-11 = 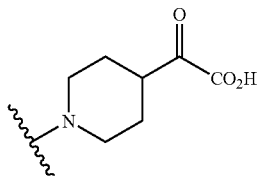
Q3-12 = 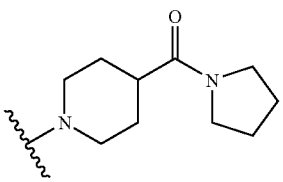
Q3-13 = 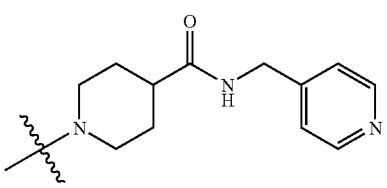

TABLE 1-continued

Q3-14 = 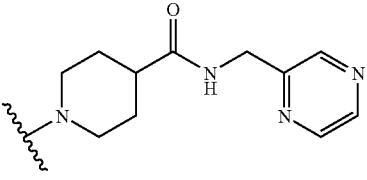

Q3-15 = 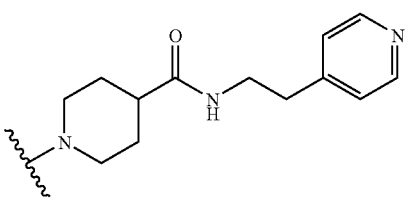

Q3-16 = 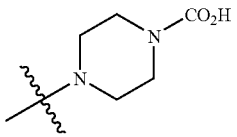

Q3-17 = 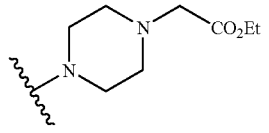

Q3-18 = 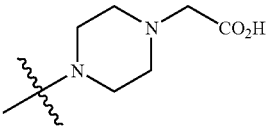

Q3-19 = 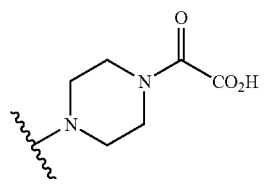

Q3-20 = 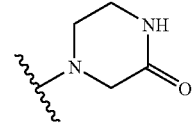

Q3-21 = 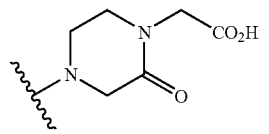

Q3-22 = 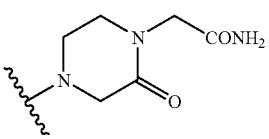

Q3-23 = 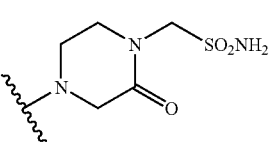

TABLE 1-continued

| $R^a$ | $R^1$ | $R^3$ |
|---|---|---|
| Q1-1 | Me | Q3-1 |
| Q1-1 | Me | Q3-2 |
| Q1-1 | Me | Q3-3 |
| Q1-1 | Me | Q3-4 |
| Q1-1 | Me | Q3-5 |
| Q1-1 | Me | Q3-6 |
| Q1-1 | Me | Q3-7 |
| Q1-1 | Me | Q3-8 |
| Q1-1 | Me | Q3-9 |
| Q1-1 | Me | Q3-10 |
| Q1-1 | Me | Q3-11 |
| Q1-1 | Me | Q3-12 |
| Q1-1 | Me | Q3-13 |
| Q1-1 | Me | Q3-14 |
| Q1-1 | Me | Q3-15 |
| Q1-1 | Me | Q3-16 |
| Q1-1 | Me | Q3-17 |
| Q1-1 | Me | Q3-18 |
| Q1-1 | Me | Q3-19 |
| Q1-1 | Me | Q3-20 |
| Q1-1 | Me | Q3-21 |
| Q1-1 | Me | Q3-22 |
| Q1-1 | Me | Q3-23 |
| Q1-2 | Me | Q3-1 |
| Q1-2 | Me | Q3-2 |
| Q1-2 | Me | Q3-3 |
| Q1-2 | Me | Q3-4 |
| Q1-2 | Me | Q3-5 |
| Q1-2 | Me | Q3-6 |
| Q1-2 | Me | Q3-7 |
| Q1-2 | Me | Q3-8 |
| Q1-2 | Me | Q3-9 |
| Q1-2 | Me | Q3-10 |
| Q1-2 | Me | Q3-11 |
| Q1-2 | Me | Q3-12 |
| Q1-2 | Me | Q3-13 |
| Q1-2 | Me | Q3-14 |
| Q1-2 | Me | Q3-15 |
| Q1-2 | Me | Q3-16 |
| Q1-2 | Me | Q3-17 |
| Q1-2 | Me | Q3-18 |
| Q1-2 | Me | Q3-19 |
| Q1-2 | Me | Q3-20 |
| Q1-2 | Me | Q3-21 |
| Q1-2 | Me | Q3-22 |
| Q1-2 | Me | Q3-23 |
| Q1-3 | Me | Q3-1 |
| Q1-3 | Me | Q3-2 |
| Q1-3 | Me | Q3-3 |
| Q1-3 | Me | Q3-4 |
| Q1-3 | Me | Q3-5 |
| Q1-3 | Me | Q3-6 |
| Q1-3 | Me | Q3-7 |
| Q1-3 | Me | Q3-8 |
| Q1-3 | Me | Q3-9 |
| Q1-3 | Me | Q3-10 |
| Q1-3 | Me | Q3-11 |
| Q1-3 | Me | Q3-12 |
| Q1-3 | Me | Q3-13 |
| Q1-3 | Me | Q3-14 |
| Q1-3 | Me | Q3-15 |
| Q1-3 | Me | Q3-16 |
| Q1-3 | Me | Q3-17 |
| Q1-3 | Me | Q3-18 |
| Q1-3 | Me | Q3-19 |
| Q1-3 | Me | Q3-20 |
| Q1-3 | Me | Q3-21 |
| Q1-3 | Me | Q3-22 |
| Q1-3 | Me | Q3-23 |
| Q1-4 | Me | Q3-1 |
| Q1-4 | Me | Q3-2 |
| Q1-4 | Me | Q3-3 |
| Q1-4 | Me | Q3-4 |
| Q1-4 | Me | Q3-5 |
| Q1-4 | Me | Q3-6 |
| Q1-4 | Me | Q3-7 |
| Q1-4 | Me | Q3-8 |
| Q1-4 | Me | Q3-9 |

TABLE 1-continued

| $R^a$ | $R^1$ | $R^3$ |
|---|---|---|
| Q1-4 | Me | Q3-10 |
| Q1-4 | Me | Q3-11 |
| Q1-4 | Me | Q3-12 |
| Q1-4 | Me | Q3-13 |
| Q1-4 | Me | Q3-14 |
| Q1-4 | Me | Q3-15 |
| Q1-4 | Me | Q3-16 |
| Q1-4 | Me | Q3-17 |
| Q1-4 | Me | Q3-18 |
| Q1-4 | Me | Q3-19 |
| Q1-4 | Me | Q3-20 |
| Q1-4 | Me | Q3-21 |
| Q1-4 | Me | Q3-22 |
| Q1-4 | Me | Q3-23 |
| Q1-5 | Me | Q3-1 |
| Q1-5 | Me | Q3-2 |
| Q1-5 | Me | Q3-3 |
| Q1-5 | Me | Q3-4 |
| Q1-5 | Me | Q3-5 |
| Q1-5 | Me | Q3-6 |
| Q1-5 | Me | Q3-7 |
| Q1-5 | Me | Q3-8 |
| Q1-5 | Me | Q3-9 |
| Q1-5 | Me | Q3-10 |
| Q1-5 | Me | Q3-11 |
| Q1-5 | Me | Q3-12 |
| Q1-5 | Me | Q3-13 |
| Q1-5 | Me | Q3-14 |
| Q1-5 | Me | Q3-15 |
| Q1-5 | Me | Q3-16 |
| Q1-5 | Me | Q3-17 |
| Q1-5 | Me | Q3-18 |
| Q1-5 | Me | Q3-19 |
| Q1-5 | Me | Q3-20 |
| Q1-5 | Me | Q3-21 |
| Q1-5 | Me | Q3-22 |
| Q1-5 | Me | Q3-23 |
| Q1-6 | Me | Q3-1 |
| Q1-6 | Me | Q3-2 |
| Q1-6 | Me | Q3-3 |
| Q1-6 | Me | Q3-4 |
| Q1-6 | Me | Q3-5 |
| Q1-6 | Me | Q3-6 |
| Q1-6 | Me | Q3-7 |
| Q1-6 | Me | Q3-8 |
| Q1-6 | Me | Q3-9 |
| Q1-6 | Me | Q3-10 |
| Q1-6 | Me | Q3-11 |
| Q1-6 | Me | Q3-12 |
| Q1-6 | Me | Q3-13 |
| Q1-6 | Me | Q3-14 |
| Q1-6 | Me | Q3-15 |
| Q1-6 | Me | Q3-16 |
| Q1-6 | Me | Q3-17 |
| Q1-6 | Me | Q3-18 |
| Q1-6 | Me | Q3-19 |
| Q1-6 | Me | Q3-20 |
| Q1-6 | Me | Q3-21 |
| Q1-6 | Me | Q3-22 |
| Q1-6 | Me | Q3-23 |
| Q1-7 | Me | Q3-1 |
| Q1-7 | Me | Q3-2 |
| Q1-7 | Me | Q3-3 |
| Q1-7 | Me | Q3-4 |
| Q1-7 | Me | Q3-5 |
| Q1-7 | Me | Q3-6 |
| Q1-7 | Me | Q3-7 |
| Q1-7 | Me | Q3-8 |
| Q1-7 | Me | Q3-9 |
| Q1-7 | Me | Q3-10 |
| Q1-7 | Me | Q3-11 |
| Q1-7 | Me | Q3-12 |
| Q1-7 | Me | Q3-13 |
| Q1-7 | Me | Q3-14 |
| Q1-7 | Me | Q3-15 |
| Q1-7 | Me | Q3-16 |
| Q1-7 | Me | Q3-17 |
| Q1-7 | Me | Q3-18 |
| Q1-7 | Me | Q3-19 |
| Q1-7 | Me | Q3-20 |
| Q1-7 | Me | Q3-21 |
| Q1-7 | Me | Q3-22 |
| Q1-7 | Me | Q3-23 |
| Q1-8 | Me | Q3-1 |
| Q1-8 | Me | Q3-2 |
| Q1-8 | Me | Q3-3 |
| Q1-8 | Me | Q3-4 |
| Q1-8 | Me | Q3-5 |
| Q1-8 | Me | Q3-6 |
| Q1-8 | Me | Q3-7 |
| Q1-8 | Me | Q3-8 |
| Q1-8 | Me | Q3-9 |
| Q1-8 | Me | Q3-10 |
| Q1-8 | Me | Q3-11 |
| Q1-8 | Me | Q3-12 |
| Q1-8 | Me | Q3-13 |
| Q1-8 | Me | Q3-14 |
| Q1-8 | Me | Q3-15 |
| Q1-8 | Me | Q3-16 |
| Q1-8 | Me | Q3-17 |
| Q1-8 | Me | Q3-18 |
| Q1-8 | Me | Q3-19 |
| Q1-8 | Me | Q3-20 |
| Q1-8 | Me | Q3-21 |
| Q1-8 | Me | Q3-22 |
| Q1-8 | Me | Q3-23 |

(35) Compounds represented by the formula (VI), wherein $R^2$ is a hydrogen atom, $R^b$ is a methyl group, X is OH, Y is a sulfur atom, and $R^a$, $R^1$ and $R^3$ are any of the following combinations shown in Table 2, tautomers, prodrugs or pharmaceutically acceptable salts of the compounds or solvates thereof. The symbols in Table 2 denote the same substituents as in Table 1.

TABLE 2

| $R^a$ | $R^1$ | $R^3$ |
|---|---|---|
| Q1-1 | Me | Q3-1 |
| Q1-1 | Me | Q3-2 |
| Q1-1 | Me | Q3-3 |
| Q1-1 | Me | Q3-4 |
| Q1-1 | Me | Q3-5 |
| Q1-1 | Me | Q3-6 |
| Q1-1 | Me | Q3-7 |
| Q1-1 | Me | Q3-8 |
| Q1-1 | Me | Q3-9 |
| Q1-1 | Me | Q3-10 |
| Q1-1 | Me | Q3-11 |
| Q1-1 | Me | Q3-12 |
| Q1-1 | Me | Q3-13 |
| Q1-1 | Me | Q3-14 |
| Q1-1 | Me | Q3-15 |
| Q1-1 | Me | Q3-16 |
| Q1-1 | Me | Q3-17 |
| Q1-1 | Me | Q3-18 |
| Q1-1 | Me | Q3-19 |
| Q1-1 | Me | Q3-20 |
| Q1-1 | Me | Q3-21 |
| Q1-1 | Me | Q3-22 |
| Q1-1 | Me | Q3-23 |
| Q1-2 | Me | Q3-1 |
| Q1-2 | Me | Q3-2 |
| Q1-2 | Me | Q3-3 |
| Q1-2 | Me | Q3-4 |
| Q1-2 | Me | Q3-5 |
| Q1-2 | Me | Q3-6 |
| Q1-2 | Me | Q3-7 |
| Q1-2 | Me | Q3-8 |
| Q1-2 | Me | Q3-9 |
| Q1-2 | Me | Q3-10 |
| Q1-2 | Me | Q3-11 |
| Q1-2 | Me | Q3-12 |
| Q1-2 | Me | Q3-13 |
| Q1-2 | Me | Q3-14 |
| Q1-2 | Me | Q3-15 |

TABLE 2-continued

| $R^a$ | $R^1$ | $R^3$ |
|---|---|---|
| Q1-2 | Me | Q3-16 |
| Q1-2 | Me | Q3-17 |
| Q1-2 | Me | Q3-18 |
| Q1-2 | Me | Q3-19 |
| Q1-2 | Me | Q3-20 |
| Q1-2 | Me | Q3-21 |
| Q1-2 | Me | Q3-22 |
| Q1-2 | Me | Q3-23 |
| Q1-3 | Me | Q3-1 |
| Q1-3 | Me | Q3-2 |
| Q1-3 | Me | Q3-3 |
| Q1-3 | Me | Q3-4 |
| Q1-3 | Me | Q3-5 |
| Q1-3 | Me | Q3-6 |
| Q1-3 | Me | Q3-7 |
| Q1-3 | Me | Q3-8 |
| Q1-3 | Me | Q3-9 |
| Q1-3 | Me | Q3-10 |
| Q1-3 | Me | Q3-11 |
| Q1-3 | Me | Q3-12 |
| Q1-3 | Me | Q3-13 |
| Q1-3 | Me | Q3-14 |
| Q1-3 | Me | Q3-15 |
| Q1-3 | Me | Q3-16 |
| Q1-3 | Me | Q3-17 |
| Q1-3 | Me | Q3-18 |
| Q1-3 | Me | Q3-19 |
| Q1-3 | Me | Q3-20 |
| Q1-3 | Me | Q3-21 |
| Q1-3 | Me | Q3-22 |
| Q1-3 | Me | Q3-23 |
| Q1-4 | Me | Q3-1 |
| Q1-4 | Me | Q3-2 |
| Q1-4 | Me | Q3-3 |
| Q1-4 | Me | Q3-4 |
| Q1-4 | Me | Q3-5 |
| Q1-4 | Me | Q3-6 |
| Q1-4 | Me | Q3-7 |
| Q1-4 | Me | Q3-8 |
| Q1-4 | Me | Q3-9 |
| Q1-4 | Me | Q3-10 |
| Q1-4 | Me | Q3-11 |
| Q1-4 | Me | Q3-12 |
| Q1-4 | Me | Q3-13 |
| Q1-4 | Me | Q3-14 |
| Q1-4 | Me | Q3-15 |
| Q1-4 | Me | Q3-16 |
| Q1-4 | Me | Q3-17 |
| Q1-4 | Me | Q3-18 |
| Q1-4 | Me | Q3-19 |
| Q1-4 | Me | Q3-20 |
| Q1-4 | Me | Q3-21 |
| Q1-4 | Me | Q3-22 |
| Q1-4 | Me | Q3-23 |
| Q1-5 | Me | Q3-1 |
| Q1-5 | Me | Q3-2 |
| Q1-5 | Me | Q3-3 |
| Q1-5 | Me | Q3-4 |
| Q1-5 | Me | Q3-5 |
| Q1-5 | Me | Q3-6 |
| Q1-5 | Me | Q3-7 |
| Q1-5 | Me | Q3-8 |
| Q1-5 | Me | Q3-9 |
| Q1-5 | Me | Q3-10 |
| Q1-5 | Me | Q3-11 |
| Q1-5 | Me | Q3-12 |
| Q1-5 | Me | Q3-13 |
| Q1-5 | Me | Q3-14 |
| Q1-5 | Me | Q3-15 |
| Q1-5 | Me | Q3-16 |
| Q1-5 | Me | Q3-17 |
| Q1-5 | Me | Q3-18 |
| Q1-5 | Me | Q3-19 |
| Q1-5 | Me | Q3-20 |
| Q1-5 | Me | Q3-21 |
| Q1-5 | Me | Q3-22 |
| Q1-5 | Me | Q3-23 |
| Q1-6 | Me | Q3-1 |
| Q1-6 | Me | Q3-2 |
| Q1-6 | Me | Q3-3 |
| Q1-6 | Me | Q3-4 |
| Q1-6 | Me | Q3-5 |
| Q1-6 | Me | Q3-6 |
| Q1-6 | Me | Q3-7 |
| Q1-6 | Me | Q3-8 |
| Q1-6 | Me | Q3-9 |
| Q1-6 | Me | Q3-10 |
| Q1-6 | Me | Q3-11 |
| Q1-6 | Me | Q3-12 |
| Q1-6 | Me | Q3-13 |
| Q1-6 | Me | Q3-14 |
| Q1-6 | Me | Q3-15 |
| Q1-6 | Me | Q3-16 |
| Q1-6 | Me | Q3-17 |
| Q1-6 | Me | Q3-18 |
| Q1-6 | Me | Q3-19 |
| Q1-6 | Me | Q3-20 |
| Q1-6 | Me | Q3-21 |
| Q1-6 | Me | Q3-22 |
| Q1-6 | Me | Q3-23 |
| Q1-7 | Me | Q3-1 |
| Q1-7 | Me | Q3-2 |
| Q1-7 | Me | Q3-3 |
| Q1-7 | Me | Q3-4 |
| Q1-7 | Me | Q3-5 |
| Q1-7 | Me | Q3-6 |
| Q1-7 | Me | Q3-7 |
| Q1-7 | Me | Q3-8 |
| Q1-7 | Me | Q3-9 |
| Q1-7 | Me | Q3-10 |
| Q1-7 | Me | Q3-11 |
| Q1-7 | Me | Q3-12 |
| Q1-7 | Me | Q3-13 |
| Q1-7 | Me | Q3-14 |
| Q1-7 | Me | Q3-15 |
| Q1-7 | Me | Q3-16 |
| Q1-7 | Me | Q3-17 |
| Q1-7 | Me | Q3-18 |
| Q1-7 | Me | Q3-19 |
| Q1-7 | Me | Q3-20 |
| Q1-7 | Me | Q3-21 |
| Q1-7 | Me | Q3-22 |
| Q1-7 | Me | Q3-23 |
| Q1-8 | Me | Q3-1 |
| Q1-8 | Me | Q3-2 |
| Q1-8 | Me | Q3-3 |
| Q1-8 | Me | Q3-4 |
| Q1-8 | Me | Q3-5 |
| Q1-8 | Me | Q3-6 |
| Q1-8 | Me | Q3-7 |
| Q1-8 | Me | Q3-8 |
| Q1-8 | Me | Q3-9 |
| Q1-8 | Me | Q3-10 |
| Q1-8 | Me | Q3-11 |
| Q1-8 | Me | Q3-12 |
| Q1-8 | Me | Q3-13 |
| Q1-8 | Me | Q3-14 |
| Q1-8 | Me | Q3-15 |
| Q1-8 | Me | Q3-16 |
| Q1-8 | Me | Q3-17 |
| Q1-8 | Me | Q3-18 |
| Q1-8 | Me | Q3-19 |
| Q1-8 | Me | Q3-20 |
| Q1-8 | Me | Q3-21 |
| Q1-8 | Me | Q3-22 |
| Q1-8 | Me | Q3-23 |

(36) Compounds represented by the formula (VII), wherein $R^2$ is a hydrogen atom, $R^b$ is a methyl group, X is OH, Y is a sulfur atom, and $R^a$, $R^1$ and $R^3$ are any of the following combinations shown in Table 3, tautomers, prodrugs or pharmaceutically acceptable salts of the compounds or solvates thereof. The symbols in Table 3 denote the same substituents as in Table 1.

TABLE 3

| R$^a$ | R$^1$ | R$^3$ |
|---|---|---|
| Q1-1 | Me | Q3-1 |
| Q1-1 | Me | Q3-2 |
| Q1-1 | Me | Q3-3 |
| Q1-1 | Me | Q3-4 |
| Q1-1 | Me | Q3-5 |
| Q1-1 | Me | Q3-6 |
| Q1-1 | Me | Q3-7 |
| Q1-1 | Me | Q3-8 |
| Q1-1 | Me | Q3-9 |
| Q1-1 | Me | Q3-10 |
| Q1-1 | Me | Q3-11 |
| Q1-1 | Me | Q3-12 |
| Q1-1 | Me | Q3-13 |
| Q1-1 | Me | Q3-14 |
| Q1-1 | Me | Q3-15 |
| Q1-1 | Me | Q3-16 |
| Q1-1 | Me | Q3-17 |
| Q1-1 | Me | Q3-18 |
| Q1-1 | Me | Q3-19 |
| Q1-1 | Me | Q3-20 |
| Q1-1 | Me | Q3-21 |
| Q1-1 | Me | Q3-22 |
| Q1-1 | Me | Q3-23 |
| Q1-2 | Me | Q3-1 |
| Q1-2 | Me | Q3-2 |
| Q1-2 | Me | Q3-3 |
| Q1-2 | Me | Q3-4 |
| Q1-2 | Me | Q3-5 |
| Q1-2 | Me | Q3-6 |
| Q1-2 | Me | Q3-7 |
| Q1-2 | Me | Q3-8 |
| Q1-2 | Me | Q3-9 |
| Q1-2 | Me | Q3-10 |
| Q1-2 | Me | Q3-11 |
| Q1-2 | Me | Q3-12 |
| Q1-2 | Me | Q3-13 |
| Q1-2 | Me | Q3-14 |
| Q1-2 | Me | Q3-15 |
| Q1-2 | Me | Q3-16 |
| Q1-2 | Me | Q3-17 |
| Q1-2 | Me | Q3-18 |
| Q1-2 | Me | Q3-19 |
| Q1-2 | Me | Q3-20 |
| Q1-2 | Me | Q3-21 |
| Q1-2 | Me | Q3-22 |
| Q1-2 | Me | Q3-23 |
| Q1-3 | Me | Q3-1 |
| Q1-3 | Me | Q3-2 |
| Q1-3 | Me | Q3-3 |
| Q1-3 | Me | Q3-4 |
| Q1-3 | Me | Q3-5 |
| Q1-3 | Me | Q3-6 |
| Q1-3 | Me | Q3-7 |
| Q1-3 | Me | Q3-8 |
| Q1-3 | Me | Q3-9 |
| Q1-3 | Me | Q3-10 |
| Q1-3 | Me | Q3-11 |
| Q1-3 | Me | Q3-12 |
| Q1-3 | Me | Q3-13 |
| Q1-3 | Me | Q3-14 |
| Q1-3 | Me | Q3-15 |
| Q1-3 | Me | Q3-16 |
| Q1-3 | Me | Q3-17 |
| Q1-3 | Me | Q3-18 |
| Q1-3 | Me | Q3-19 |
| Q1-3 | Me | Q3-20 |
| Q1-3 | Me | Q3-21 |
| Q1-3 | Me | Q3-22 |
| Q1-3 | Me | Q3-23 |
| Q1-4 | Me | Q3-1 |
| Q1-4 | Me | Q3-2 |
| Q1-4 | Me | Q3-3 |
| Q1-4 | Me | Q3-4 |
| Q1-4 | Me | Q3-5 |
| Q1-4 | Me | Q3-6 |
| Q1-4 | Me | Q3-7 |
| Q1-4 | Me | Q3-8 |
| Q1-4 | Me | Q3-9 |
| Q1-4 | Me | Q3-10 |
| Q1-4 | Me | Q3-11 |
| Q1-4 | Me | Q3-12 |
| Q1-4 | Me | Q3-13 |
| Q1-4 | Me | Q3-14 |
| Q1-4 | Me | Q3-15 |
| Q1-4 | Me | Q3-16 |
| Q1-4 | Me | Q3-17 |
| Q1-4 | Me | Q3-18 |
| Q1-4 | Me | Q3-19 |
| Q1-4 | Me | Q3-20 |
| Q1-4 | Me | Q3-21 |
| Q1-4 | Me | Q3-22 |
| Q1-4 | Me | Q3-23 |
| Q1-5 | Me | Q3-1 |
| Q1-5 | Me | Q3-2 |
| Q1-5 | Me | Q3-3 |
| Q1-5 | Me | Q3-4 |
| Q1-5 | Me | Q3-5 |
| Q1-5 | Me | Q3-6 |
| Q1-5 | Me | Q3-7 |
| Q1-5 | Me | Q3-8 |
| Q1-5 | Me | Q3-9 |
| Q1-5 | Me | Q3-10 |
| Q1-5 | Me | Q3-11 |
| Q1-5 | Me | Q3-12 |
| Q1-5 | Me | Q3-13 |
| Q1-5 | Me | Q3-14 |
| Q1-5 | Me | Q3-15 |
| Q1-5 | Me | Q3-16 |
| Q1-5 | Me | Q3-17 |
| Q1-5 | Me | Q3-18 |
| Q1-5 | Me | Q3-19 |
| Q1-5 | Me | Q3-20 |
| Q1-5 | Me | Q3-21 |
| Q1-5 | Me | Q3-22 |
| Q1-5 | Me | Q3-23 |
| Q1-6 | Me | Q3-1 |
| Q1-6 | Me | Q3-2 |
| Q1-6 | Me | Q3-3 |
| Q1-6 | Me | Q3-4 |
| Q1-6 | Me | Q3-5 |
| Q1-6 | Me | Q3-6 |
| Q1-6 | Me | Q3-7 |
| Q1-6 | Me | Q3-8 |
| Q1-6 | Me | Q3-9 |
| Q1-6 | Me | Q3-10 |
| Q1-6 | Me | Q3-11 |
| Q1-6 | Me | Q3-12 |
| Q1-6 | Me | Q3-13 |
| Q1-6 | Me | Q3-14 |
| Q1-6 | Me | Q3-15 |
| Q1-6 | Me | Q3-16 |
| Q1-6 | Me | Q3-17 |
| Q1-6 | Me | Q3-18 |
| Q1-6 | Me | Q3-19 |
| Q1-6 | Me | Q3-20 |
| Q1-6 | Me | Q3-21 |
| Q1-6 | Me | Q3-22 |
| Q1-6 | Me | Q3-23 |
| Q1-7 | Me | Q3-1 |
| Q1-7 | Me | Q3-2 |
| Q1-7 | Me | Q3-3 |
| Q1-7 | Me | Q3-4 |
| Q1-7 | Me | Q3-5 |
| Q1-7 | Me | Q3-6 |
| Q1-7 | Me | Q3-7 |
| Q1-7 | Me | Q3-8 |
| Q1-7 | Me | Q3-9 |
| Q1-7 | Me | Q3-10 |
| Q1-7 | Me | Q3-11 |
| Q1-7 | Me | Q3-12 |
| Q1-7 | Me | Q3-13 |
| Q1-7 | Me | Q3-14 |
| Q1-7 | Me | Q3-15 |
| Q1-7 | Me | Q3-16 |
| Q1-7 | Me | Q3-17 |
| Q1-7 | Me | Q3-18 |

TABLE 3-continued

| R$^a$ | R$^1$ | R$^3$ |
|---|---|---|
| Q1-7 | Me | Q3-19 |
| Q1-7 | Me | Q3-20 |
| Q1-7 | Me | Q3-21 |
| Q1-7 | Me | Q3-22 |
| Q1-7 | Me | Q3-23 |
| Q1-8 | Me | Q3-1 |
| Q1-8 | Me | Q3-2 |
| Q1-8 | Me | Q3-3 |
| Q1-8 | Me | Q3-4 |
| Q1-8 | Me | Q3-5 |
| Q1-8 | Me | Q3-6 |
| Q1-8 | Me | Q3-7 |
| Q1-8 | Me | Q3-8 |
| Q1-8 | Me | Q3-9 |
| Q1-8 | Me | Q3-10 |
| Q1-8 | Me | Q3-11 |
| Q1-8 | Me | Q3-12 |
| Q1-8 | Me | Q3-13 |
| Q1-8 | Me | Q3-14 |
| Q1-8 | Me | Q3-15 |
| Q1-8 | Me | Q3-16 |
| Q1-8 | Me | Q3-17 |
| Q1-8 | Me | Q3-18 |
| Q1-8 | Me | Q3-19 |
| Q1-8 | Me | Q3-20 |
| Q1-8 | Me | Q3-21 |
| Q1-8 | Me | Q3-22 |
| Q1-8 | Me | Q3-23 |

(37) The compounds according to any of (34), (35) and (36), wherein R$^1$ is converted to a hydrogen atom, tautomers, prodrugs or pharmaceutically acceptable salts of the compounds or solvates thereof.

(38) The compounds according to any of (34), (35) and (36), wherein R$^1$ is converted to a trifluoromethyl group, tautomers, prodrugs or pharmaceutically acceptable salts of the compounds or solvates thereof.

(39) The compounds according to any of (34), (35) and (36), wherein R$^1$ is converted to an ethyl group, tautomers, prodrugs or pharmaceutically acceptable salts of the compounds or solvates thereof.

(40) The compounds according to any of (34), (35) and (36), wherein R$^1$ is converted to a n-propyl group, tautomers, prodrugs or pharmaceutically acceptable salts of the compounds or solvates thereof.

(41) The compounds according to any of (34), (35) and (36), wherein R$^1$ is converted to an i-propyl group, tautomers, prodrugs or pharmaceutically acceptable salts of the compounds or solvates thereof.

(42) The compounds according to any of (34) to (41), wherein R$^b$ is converted to a hydrogen atom, tautomers, prodrugs or pharmaceutically acceptable salts of the compounds or solvates thereof.

(43) The compounds according to any of (34) to (41), wherein R$^b$ is converted to a trifluoromethyl group, tautomers, prodrugs or pharmaceutically acceptable salts of the compounds or solvates thereof.

(44) The compounds according to any of (34) to (41), wherein R$^b$ is converted to an ethyl group, tautomers, prodrugs or pharmaceutically acceptable salts of the compounds or solvates thereof.

(45) The compounds according to any of (34) to (41), wherein R$^b$ is converted to a n-propyl group, tautomers, prodrugs or pharmaceutically acceptable salts of the compounds or solvates thereof.

(46) The compounds according to any of (34) to (41), wherein R$^b$ is converted to an i-propyl group, tautomers, prodrugs or pharmaceutically acceptable salts of the compounds or solvates thereof.

(47) Compounds represented by the formula (IX), wherein R$^2$ is a hydrogen atom, R$^b$ and R$^c$ are methyl groups, X is OH, Y is a sulfur atom, and R$^a$, R$^1$ and R$^3$ are any of the following combinations shown in Table 4, tautomers, prodrugs or pharmaceutically acceptable salts of the compounds or solvates thereof. The symbols in Table 4 denote the same substituents as in Table 1.

TABLE 4

| R$^a$ | R$^1$ | R$^3$ |
|---|---|---|
| Q1-1 | Me | Q3-1 |
| Q1-1 | Me | Q3-2 |
| Q1-1 | Me | Q3-3 |
| Q1-1 | Me | Q3-4 |
| Q1-1 | Me | Q3-5 |
| Q1-1 | Me | Q3-6 |
| Q1-1 | Me | Q3-7 |
| Q1-1 | Me | Q3-8 |
| Q1-1 | Me | Q3-9 |
| Q1-1 | Me | Q3-10 |
| Q1-1 | Me | Q3-11 |
| Q1-1 | Me | Q3-12 |
| Q1-1 | Me | Q3-13 |
| Q1-1 | Me | Q3-14 |
| Q1-1 | Me | Q3-15 |
| Q1-1 | Me | Q3-16 |
| Q1-1 | Me | Q3-17 |
| Q1-1 | Me | Q3-18 |
| Q1-1 | Me | Q3-19 |
| Q1-1 | Me | Q3-20 |
| Q1-1 | Me | Q3-21 |
| Q1-1 | Me | Q3-22 |
| Q1-1 | Me | Q3-23 |
| Q1-2 | Me | Q3-1 |
| Q1-2 | Me | Q3-2 |
| Q1-2 | Me | Q3-3 |
| Q1-2 | Me | Q3-4 |
| Q1-2 | Me | Q3-5 |
| Q1-2 | Me | Q3-6 |
| Q1-2 | Me | Q3-7 |
| Q1-2 | Me | Q3-8 |
| Q1-2 | Me | Q3-9 |
| Q1-2 | Me | Q3-10 |
| Q1-2 | Me | Q3-11 |
| Q1-2 | Me | Q3-12 |
| Q1-2 | Me | Q3-13 |
| Q1-2 | Me | Q3-14 |
| Q1-2 | Me | Q3-15 |
| Q1-2 | Me | Q3-16 |
| Q1-2 | Me | Q3-17 |
| Q1-2 | Me | Q3-18 |
| Q1-2 | Me | Q3-19 |
| Q1-2 | Me | Q3-20 |
| Q1-2 | Me | Q3-21 |
| Q1-2 | Me | Q3-22 |
| Q1-2 | Me | Q3-23 |
| Q1-3 | Me | Q3-1 |
| Q1-3 | Me | Q3-2 |
| Q1-3 | Me | Q3-3 |
| Q1-3 | Me | Q3-4 |
| Q1-3 | Me | Q3-5 |
| Q1-3 | Me | Q3-6 |
| Q1-3 | Me | Q3-7 |
| Q1-3 | Me | Q3-8 |
| Q1-3 | Me | Q3-9 |
| Q1-3 | Me | Q3-10 |
| Q1-3 | Me | Q3-11 |
| Q1-3 | Me | Q3-12 |
| Q1-3 | Me | Q3-13 |
| Q1-3 | Me | Q3-14 |
| Q1-3 | Me | Q3-15 |
| Q1-3 | Me | Q3-16 |
| Q1-3 | Me | Q3-17 |
| Q1-3 | Me | Q3-18 |
| Q1-3 | Me | Q3-19 |
| Q1-3 | Me | Q3-20 |
| Q1-3 | Me | Q3-21 |
| Q1-3 | Me | Q3-22 |

TABLE 4-continued

| $R^a$ | $R^1$ | $R^3$ |
|---|---|---|
| Q1-3 | Me | Q3-23 |
| Q1-4 | Me | Q3-1 |
| Q1-4 | Me | Q3-2 |
| Q1-4 | Me | Q3-3 |
| Q1-4 | Me | Q3-4 |
| Q1-4 | Me | Q3-5 |
| Q1-4 | Me | Q3-6 |
| Q1-4 | Me | Q3-7 |
| Q1-4 | Me | Q3-8 |
| Q1-4 | Me | Q3-9 |
| Q1-4 | Me | Q3-10 |
| Q1-4 | Me | Q3-11 |
| Q1-4 | Me | Q3-12 |
| Q1-4 | Me | Q3-13 |
| Q1-4 | Me | Q3-14 |
| Q1-4 | Me | Q3-15 |
| Q1-4 | Me | Q3-16 |
| Q1-4 | Me | Q3-17 |
| Q1-4 | Me | Q3-18 |
| Q1-4 | Me | Q3-19 |
| Q1-4 | Me | Q3-20 |
| Q1-4 | Me | Q3-21 |
| Q1-4 | Me | Q3-22 |
| Q1-4 | Me | Q3-23 |
| Q1-5 | Me | Q3-1 |
| Q1-5 | Me | Q3-2 |
| Q1-5 | Me | Q3-3 |
| Q1-5 | Me | Q3-4 |
| Q1-5 | Me | Q3-5 |
| Q1-5 | Me | Q3-6 |
| Q1-5 | Me | Q3-7 |
| Q1-5 | Me | Q3-8 |
| Q1-5 | Me | Q3-9 |
| Q1-5 | Me | Q3-10 |
| Q1-5 | Me | Q3-11 |
| Q1-5 | Me | Q3-12 |
| Q1-5 | Me | Q3-13 |
| Q1-5 | Me | Q3-14 |
| Q1-5 | Me | Q3-15 |
| Q1-5 | Me | Q3-16 |
| Q1-5 | Me | Q3-17 |
| Q1-5 | Me | Q3-18 |
| Q1-5 | Me | Q3-19 |
| Q1-5 | Me | Q3-20 |
| Q1-5 | Me | Q3-21 |
| Q1-5 | Me | Q3-22 |
| Q1-5 | Me | Q3-23 |
| Q1-6 | Me | Q3-1 |
| Q1-6 | Me | Q3-2 |
| Q1-6 | Me | Q3-3 |
| Q1-6 | Me | Q3-4 |
| Q1-6 | Me | Q3-5 |
| Q1-6 | Me | Q3-6 |
| Q1-6 | Me | Q3-7 |
| Q1-6 | Me | Q3-8 |
| Q1-6 | Me | Q3-9 |
| Q1-6 | Me | Q3-10 |
| Q1-6 | Me | Q3-11 |
| Q1-6 | Me | Q3-12 |
| Q1-6 | Me | Q3-13 |
| Q1-6 | Me | Q3-14 |
| Q1-6 | Me | Q3-15 |
| Q1-6 | Me | Q3-16 |
| Q1-6 | Me | Q3-17 |
| Q1-6 | Me | Q3-18 |
| Q1-6 | Me | Q3-19 |
| Q1-6 | Me | Q3-20 |
| Q1-6 | Me | Q3-21 |
| Q1-6 | Me | Q3-22 |
| Q1-6 | Me | Q3-23 |
| Q1-7 | Me | Q3-1 |
| Q1-7 | Me | Q3-2 |
| Q1-7 | Me | Q3-3 |
| Q1-7 | Me | Q3-4 |
| Q1-7 | Me | Q3-5 |
| Q1-7 | Me | Q3-6 |
| Q1-7 | Me | Q3-7 |
| Q1-7 | Me | Q3-8 |
| Q1-7 | Me | Q3-9 |
| Q1-7 | Me | Q3-10 |
| Q1-7 | Me | Q3-11 |
| Q1-7 | Me | Q3-12 |
| Q1-7 | Me | Q3-13 |
| Q1-7 | Me | Q3-14 |
| Q1-7 | Me | Q3-15 |
| Q1-7 | Me | Q3-16 |
| Q1-7 | Me | Q3-17 |
| Q1-7 | Me | Q3-18 |
| Q1-7 | Me | Q3-19 |
| Q1-7 | Me | Q3-20 |
| Q1-7 | Me | Q3-21 |
| Q1-7 | Me | Q3-22 |
| Q1-7 | Me | Q3-23 |
| Q1-8 | Me | Q3-1 |
| Q1-8 | Me | Q3-2 |
| Q1-8 | Me | Q3-3 |
| Q1-8 | Me | Q3-4 |
| Q1-8 | Me | Q3-5 |
| Q1-8 | Me | Q3-6 |
| Q1-8 | Me | Q3-7 |
| Q1-8 | Me | Q3-8 |
| Q1-8 | Me | Q3-9 |
| Q1-8 | Me | Q3-10 |
| Q1-8 | Me | Q3-11 |
| Q1-8 | Me | Q3-12 |
| Q1-8 | Me | Q3-13 |
| Q1-8 | Me | Q3-14 |
| Q1-8 | Me | Q3-15 |
| Q1-8 | Me | Q3-16 |
| Q1-8 | Me | Q3-17 |
| Q1-8 | Me | Q3-18 |
| Q1-8 | Me | Q3-19 |
| Q1-8 | Me | Q3-20 |
| Q1-8 | Me | Q3-21 |
| Q1-8 | Me | Q3-22 |
| Q1-8 | Me | Q3-23 |

(48) Compounds represented by the formula (X), wherein $R^2$ is a hydrogen atom, $R^b$ and $R^c$ are methyl groups, X is OH, Y is a sulfur atom, and $R^a$, $R^1$ and $R^3$ are any of the following combinations shown in Table 5, tautomers, prodrugs or pharmaceutically acceptable salts of the compounds or solvates thereof. The symbols in Table 5 denote the same substituents as in Table 1.

TABLE 5

| $R^a$ | $R^1$ | $R^3$ |
|---|---|---|
| Q1-1 | Me | Q3-1 |
| Q1-1 | Me | Q3-2 |
| Q1-1 | Me | Q3-3 |
| Q1-1 | Me | Q3-4 |
| Q1-1 | Me | Q3-5 |
| Q1-1 | Me | Q3-6 |
| Q1-1 | Me | Q3-7 |
| Q1-1 | Me | Q3-8 |
| Q1-1 | Me | Q3-9 |
| Q1-1 | Me | Q3-10 |
| Q1-1 | Me | Q3-11 |
| Q1-1 | Me | Q3-12 |
| Q1-1 | Me | Q3-13 |
| Q1-1 | Me | Q3-14 |
| Q1-1 | Me | Q3-15 |
| Q1-1 | Me | Q3-16 |
| Q1-1 | Me | Q3-17 |
| Q1-1 | Me | Q3-18 |
| Q1-1 | Me | Q3-19 |
| Q1-1 | Me | Q3-20 |
| Q1-1 | Me | Q3-21 |
| Q1-1 | Me | Q3-22 |
| Q1-1 | Me | Q3-23 |
| Q1-2 | Me | Q3-1 |

TABLE 5-continued

| $R^a$ | $R^1$ | $R^3$ |
|---|---|---|
| Q1-2 | Me | Q3-2 |
| Q1-2 | Me | Q3-3 |
| Q1-2 | Me | Q3-4 |
| Q1-2 | Me | Q3-5 |
| Q1-2 | Me | Q3-6 |
| Q1-2 | Me | Q3-7 |
| Q1-2 | Me | Q3-8 |
| Q1-2 | Me | Q3-9 |
| Q1-2 | Me | Q3-10 |
| Q1-2 | Me | Q3-11 |
| Q1-2 | Me | Q3-12 |
| Q1-2 | Me | Q3-13 |
| Q1-2 | Me | Q3-14 |
| Q1-2 | Me | Q3-15 |
| Q1-2 | Me | Q3-16 |
| Q1-2 | Me | Q3-17 |
| Q1-2 | Me | Q3-18 |
| Q1-2 | Me | Q3-19 |
| Q1-2 | Me | Q3-20 |
| Q1-2 | Me | Q3-21 |
| Q1-2 | Me | Q3-22 |
| Q1-2 | Me | Q3-23 |
| Q1-3 | Me | Q3-1 |
| Q1-3 | Me | Q3-2 |
| Q1-3 | Me | Q3-3 |
| Q1-3 | Me | Q3-4 |
| Q1-3 | Me | Q3-5 |
| Q1-3 | Me | Q3-6 |
| Q1-3 | Me | Q3-7 |
| Q1-3 | Me | Q3-8 |
| Q1-3 | Me | Q3-9 |
| Q1-3 | Me | Q3-10 |
| Q1-3 | Me | Q3-11 |
| Q1-3 | Me | Q3-12 |
| Q1-3 | Me | Q3-13 |
| Q1-3 | Me | Q3-14 |
| Q1-3 | Me | Q3-15 |
| Q1-3 | Me | Q3-16 |
| Q1-3 | Me | Q3-17 |
| Q1-3 | Me | Q3-18 |
| Q1-3 | Me | Q3-19 |
| Q1-3 | Me | Q3-20 |
| Q1-3 | Me | Q3-21 |
| Q1-3 | Me | Q3-22 |
| Q1-3 | Me | Q3-23 |
| Q1-4 | Me | Q3-1 |
| Q1-4 | Me | Q3-2 |
| Q1-4 | Me | Q3-3 |
| Q1-4 | Me | Q3-4 |
| Q1-4 | Me | Q3-5 |
| Q1-4 | Me | Q3-6 |
| Q1-4 | Me | Q3-7 |
| Q1-4 | Me | Q3-8 |
| Q1-4 | Me | Q3-9 |
| Q1-4 | Me | Q3-10 |
| Q1-4 | Me | Q3-11 |
| Q1-4 | Me | Q3-12 |
| Q1-4 | Me | Q3-13 |
| Q1-4 | Me | Q3-14 |
| Q1-4 | Me | Q3-15 |
| Q1-4 | Me | Q3-16 |
| Q1-4 | Me | Q3-17 |
| Q1-4 | Me | Q3-18 |
| Q1-4 | Me | Q3-19 |
| Q1-4 | Me | Q3-20 |
| Q1-4 | Me | Q3-21 |
| Q1-4 | Me | Q3-22 |
| Q1-4 | Me | Q3-23 |
| Q1-5 | Me | Q3-1 |
| Q1-5 | Me | Q3-2 |
| Q1-5 | Me | Q3-3 |
| Q1-5 | Me | Q3-4 |
| Q1-5 | Me | Q3-5 |
| Q1-5 | Me | Q3-6 |
| Q1-5 | Me | Q3-7 |
| Q1-5 | Me | Q3-8 |
| Q1-5 | Me | Q3-9 |
| Q1-5 | Me | Q3-10 |
| Q1-5 | Me | Q3-11 |
| Q1-5 | Me | Q3-12 |
| Q1-5 | Me | Q3-13 |
| Q1-5 | Me | Q3-14 |
| Q1-5 | Me | Q3-15 |
| Q1-5 | Me | Q3-16 |
| Q1-5 | Me | Q3-17 |
| Q1-5 | Me | Q3-18 |
| Q1-5 | Me | Q3-19 |
| Q1-5 | Me | Q3-20 |
| Q1-5 | Me | Q3-21 |
| Q1-5 | Me | Q3-22 |
| Q1-5 | Me | Q3-23 |
| Q1-6 | Me | Q3-1 |
| Q1-6 | Me | Q3-2 |
| Q1-6 | Me | Q3-3 |
| Q1-6 | Me | Q3-4 |
| Q1-6 | Me | Q3-5 |
| Q1-6 | Me | Q3-6 |
| Q1-6 | Me | Q3-7 |
| Q1-6 | Me | Q3-8 |
| Q1-6 | Me | Q3-9 |
| Q1-6 | Me | Q3-10 |
| Q1-6 | Me | Q3-11 |
| Q1-6 | Me | Q3-12 |
| Q1-6 | Me | Q3-13 |
| Q1-6 | Me | Q3-14 |
| Q1-6 | Me | Q3-15 |
| Q1-6 | Me | Q3-16 |
| Q1-6 | Me | Q3-17 |
| Q1-6 | Me | Q3-18 |
| Q1-6 | Me | Q3-19 |
| Q1-6 | Me | Q3-20 |
| Q1-6 | Me | Q3-21 |
| Q1-6 | Me | Q3-22 |
| Q1-6 | Me | Q3-23 |
| Q1-7 | Me | Q3-1 |
| Q1-7 | Me | Q3-2 |
| Q1-7 | Me | Q3-3 |
| Q1-7 | Me | Q3-4 |
| Q1-7 | Me | Q3-5 |
| Q1-7 | Me | Q3-6 |
| Q1-7 | Me | Q3-7 |
| Q1-7 | Me | Q3-8 |
| Q1-7 | Me | Q3-9 |
| Q1-7 | Me | Q3-10 |
| Q1-7 | Me | Q3-11 |
| Q1-7 | Me | Q3-12 |
| Q1-7 | Me | Q3-13 |
| Q1-7 | Me | Q3-14 |
| Q1-7 | Me | Q3-15 |
| Q1-7 | Me | Q3-16 |
| Q1-7 | Me | Q3-17 |
| Q1-7 | Me | Q3-18 |
| Q1-7 | Me | Q3-19 |
| Q1-7 | Me | Q3-20 |
| Q1-7 | Me | Q3-21 |
| Q1-7 | Me | Q3-22 |
| Q1-7 | Me | Q3-23 |
| Q1-8 | Me | Q3-1 |
| Q1-8 | Me | Q3-2 |
| Q1-8 | Me | Q3-3 |
| Q1-8 | Me | Q3-4 |
| Q1-8 | Me | Q3-5 |
| Q1-8 | Me | Q3-6 |
| Q1-8 | Me | Q3-7 |
| Q1-8 | Me | Q3-8 |
| Q1-8 | Me | Q3-9 |
| Q1-8 | Me | Q3-10 |
| Q1-8 | Me | Q3-11 |
| Q1-8 | Me | Q3-12 |
| Q1-8 | Me | Q3-13 |
| Q1-8 | Me | Q3-14 |
| Q1-8 | Me | Q3-15 |
| Q1-8 | Me | Q3-16 |
| Q1-8 | Me | Q3-17 |
| Q1-8 | Me | Q3-18 |
| Q1-8 | Me | Q3-19 |

TABLE 5-continued

| $R^a$ | $R^1$ | $R^3$ |
|---|---|---|
| Q1-8 | Me | Q3-20 |
| Q1-8 | Me | Q3-21 |
| Q1-8 | Me | Q3-22 |
| Q1-8 | Me | Q3-23 |

(49) The compounds according to any of (47) and (48), wherein $R^1$ is converted to a hydrogen atom, tautomers, prodrugs or pharmaceutically acceptable salts of the compounds or solvates thereof.

(50) The compounds according to any of (47) and (48), wherein $R^1$ is converted to a trifluoromethyl group, tautomers, prodrugs or pharmaceutically acceptable salts of the compounds or solvates thereof.

(51) The compounds according to any of 47) and (48), wherein $R^1$ is converted to an ethyl group, tautomers, prodrugs or pharmaceutically acceptable salts of the compounds or solvates thereof.

(52) The compounds according to any of (47) and (48), wherein $R^1$ is converted to a n-propyl group, tautomers, prodrugs or pharmaceutically acceptable salts of the compounds or solvates thereof.

(53) The compounds according to any of (47) and (48), wherein $R^1$ is converted to an i-propyl group, tautomers, prodrugs or pharmaceutically acceptable salts of the compounds or solvates thereof.

(54) The compounds according to any of (47) to (53), wherein $R^b$ is converted to a hydrogen atom, and $R^c$ is converted to a hydrogen atom, tautomers, prodrugs or pharmaceutically acceptable salts of the compounds or solvates thereof.

(55) The compounds according to any of (47) to (53), wherein $R^b$ is converted to a hydrogen atom, and $R^c$ is converted to a trifluoromethyl group, tautomers, prodrugs or pharmaceutically acceptable salts of the compounds or solvates thereof.

(56) The compounds according to any of (47) to (53), wherein $R^b$ is converted to a hydrogen atom, and $R^c$ is converted to an ethyl group, tautomers, prodrugs or pharmaceutically acceptable salts of the compounds or solvates thereof.

(57) The compounds according to any of (47) to (53), wherein $R^b$ is converted to a hydrogen atom, and $R^c$ is converted to a n-propyl group, tautomers, prodrugs or pharmaceutically acceptable salts of the compounds or solvates thereof.

(58) The compounds according to any of (47) to (53), wherein $R^b$ is converted to a hydrogen atom, and $R^c$ is converted to an i-propyl group, tautomers, prodrugs or pharmaceutically acceptable salts of the compounds or solvates thereof.

(59) Compounds represented by the formula (XI), wherein $R^2$ is a hydrogen atom, $R^{28}$, $R^{29}$, $R^{30}$ and $R^{31}$ are hydrogen atoms, X is OH, Y is a sulfur atom, and $R^a$, $R^1$ and $R^3$ are any of the following combinations shown in Table 6, tautomers, prodrugs or pharmaceutically acceptable salts of the compounds or solvates thereof. The symbols in Table 6 denote the same substituents as in Table 1.

TABLE 6

| $R^a$ | $R^1$ | $R^3$ |
|---|---|---|
| Q1-1 | Me | Q3-1 |
| Q1-1 | Me | Q3-2 |
| Q1-1 | Me | Q3-3 |
| Q1-1 | Me | Q3-4 |
| Q1-1 | Me | Q3-5 |
| Q1-1 | Me | Q3-6 |
| Q1-1 | Me | Q3-7 |
| Q1-1 | Me | Q3-8 |
| Q1-1 | Me | Q3-9 |
| Q1-1 | Me | Q3-10 |
| Q1-1 | Me | Q3-11 |
| Q1-1 | Me | Q3-12 |
| Q1-1 | Me | Q3-13 |
| Q1-1 | Me | Q3-14 |
| Q1-1 | Me | Q3-15 |
| Q1-1 | Me | Q3-16 |
| Q1-1 | Me | Q3-17 |
| Q1-1 | Me | Q3-18 |
| Q1-1 | Me | Q3-19 |
| Q1-1 | Me | Q3-20 |
| Q1-1 | Me | Q3-21 |
| Q1-1 | Me | Q3-22 |
| Q1-1 | Me | Q3-23 |
| Q1-2 | Me | Q3-1 |
| Q1-2 | Me | Q3-2 |
| Q1-2 | Me | Q3-3 |
| Q1-2 | Me | Q3-4 |
| Q1-2 | Me | Q3-5 |
| Q1-2 | Me | Q3-6 |
| Q1-2 | Me | Q3-7 |
| Q1-2 | Me | Q3-8 |
| Q1-2 | Me | Q3-9 |
| Q1-2 | Me | Q3-10 |
| Q1-2 | Me | Q3-11 |
| Q1-2 | Me | Q3-12 |
| Q1-2 | Me | Q3-13 |
| Q1-2 | Me | Q3-14 |
| Q1-2 | Me | Q3-15 |
| Q1-2 | Me | Q3-16 |
| Q1-2 | Me | Q3-17 |
| Q1-2 | Me | Q3-18 |
| Q1-2 | Me | Q3-19 |
| Q1-2 | Me | Q3-20 |
| Q1-2 | Me | Q3-21 |
| Q1-2 | Me | Q3-22 |
| Q1-2 | Me | Q3-23 |
| Q1-3 | Me | Q3-1 |
| Q1-3 | Me | Q3-2 |
| Q1-3 | Me | Q3-3 |
| Q1-3 | Me | Q3-4 |
| Q1-3 | Me | Q3-5 |
| Q1-3 | Me | Q3-6 |
| Q1-3 | Me | Q3-7 |
| Q1-3 | Me | Q3-8 |
| Q1-3 | Me | Q3-9 |
| Q1-3 | Me | Q3-10 |
| Q1-3 | Me | Q3-11 |
| Q1-3 | Me | Q3-12 |
| Q1-3 | Me | Q3-13 |
| Q1-3 | Me | Q3-14 |
| Q1-3 | Me | Q3-15 |
| Q1-3 | Me | Q3-16 |
| Q1-3 | Me | Q3-17 |
| Q1-3 | Me | Q3-18 |
| Q1-3 | Me | Q3-19 |
| Q1-3 | Me | Q3-20 |
| Q1-3 | Me | Q3-21 |
| Q1-3 | Me | Q3-22 |
| Q1-3 | Me | Q3-23 |
| Q1-4 | Me | Q3-1 |
| Q1-4 | Me | Q3-2 |
| Q1-4 | Me | Q3-3 |
| Q1-4 | Me | Q3-4 |
| Q1-4 | Me | Q3-5 |
| Q1-4 | Me | Q3-6 |
| Q1-4 | Me | Q3-7 |
| Q1-4 | Me | Q3-8 |
| Q1-4 | Me | Q3-9 |
| Q1-4 | Me | Q3-10 |
| Q1-4 | Me | Q3-11 |
| Q1-4 | Me | Q3-12 |

TABLE 6-continued

| R$^a$ | R$^1$ | R$^3$ |
|---|---|---|
| Q1-4 | Me | Q3-13 |
| Q1-4 | Me | Q3-14 |
| Q1-4 | Me | Q3-15 |
| Q1-4 | Me | Q3-16 |
| Q1-4 | Me | Q3-17 |
| Q1-4 | Me | Q3-18 |
| Q1-4 | Me | Q3-19 |
| Q1-4 | Me | Q3-20 |
| Q1-4 | Me | Q3-21 |
| Q1-4 | Me | Q3-22 |
| Q1-4 | Me | Q3-23 |
| Q1-5 | Me | Q3-1 |
| Q1-5 | Me | Q3-2 |
| Q1-5 | Me | Q3-3 |
| Q1-5 | Me | Q3-4 |
| Q1-5 | Me | Q3-5 |
| Q1-5 | Me | Q3-6 |
| Q1-5 | Me | Q3-7 |
| Q1-5 | Me | Q3-8 |
| Q1-5 | Me | Q3-9 |
| Q1-5 | Me | Q3-10 |
| Q1-5 | Me | Q3-11 |
| Q1-5 | Me | Q3-12 |
| Q1-5 | Me | Q3-13 |
| Q1-5 | Me | Q3-14 |
| Q1-5 | Me | Q3-15 |
| Q1-5 | Me | Q3-16 |
| Q1-5 | Me | Q3-17 |
| Q1-5 | Me | Q3-18 |
| Q1-5 | Me | Q3-19 |
| Q1-5 | Me | Q3-20 |
| Q1-5 | Me | Q3-21 |
| Q1-5 | Me | Q3-22 |
| Q1-5 | Me | Q3-23 |
| Q1-6 | Me | Q3-1 |
| Q1-6 | Me | Q3-2 |
| Q1-6 | Me | Q3-3 |
| Q1-6 | Me | Q3-4 |
| Q1-6 | Me | Q3-5 |
| Q1-6 | Me | Q3-6 |
| Q1-6 | Me | Q3-7 |
| Q1-6 | Me | Q3-8 |
| Q1-6 | Me | Q3-9 |
| Q1-6 | Me | Q3-10 |
| Q1-6 | Me | Q3-11 |
| Q1-6 | Me | Q3-12 |
| Q1-6 | Me | Q3-13 |
| Q1-6 | Me | Q3-14 |
| Q1-6 | Me | Q3-15 |
| Q1-6 | Me | Q3-16 |
| Q1-6 | Me | Q3-17 |
| Q1-6 | Me | Q3-18 |
| Q1-6 | Me | Q3-19 |
| Q1-6 | Me | Q3-20 |
| Q1-6 | Me | Q3-21 |
| Q1-6 | Me | Q3-22 |
| Q1-6 | Me | Q3-23 |
| Q1-7 | Me | Q3-1 |
| Q1-7 | Me | Q3-2 |
| Q1-7 | Me | Q3-3 |
| Q1-7 | Me | Q3-4 |
| Q1-7 | Me | Q3-5 |
| Q1-7 | Me | Q3-6 |
| Q1-7 | Me | Q3-7 |
| Q1-7 | Me | Q3-8 |
| Q1-7 | Me | Q3-9 |
| Q1-7 | Me | Q3-10 |
| Q1-7 | Me | Q3-11 |
| Q1-7 | Me | Q3-12 |
| Q1-7 | Me | Q3-13 |
| Q1-7 | Me | Q3-14 |
| Q1-7 | Me | Q3-15 |
| Q1-7 | Me | Q3-16 |
| Q1-7 | Me | Q3-17 |
| Q1-7 | Me | Q3-18 |
| Q1-7 | Me | Q3-19 |
| Q1-7 | Me | Q3-20 |
| Q1-7 | Me | Q3-21 |
| Q1-7 | Me | Q3-22 |
| Q1-7 | Me | Q3-23 |
| Q1-8 | Me | Q3-1 |
| Q1-8 | Me | Q3-2 |
| Q1-8 | Me | Q3-3 |
| Q1-8 | Me | Q3-4 |
| Q1-8 | Me | Q3-5 |
| Q1-8 | Me | Q3-6 |
| Q1-8 | Me | Q3-7 |
| Q1-8 | Me | Q3-8 |
| Q1-8 | Me | Q3-9 |
| Q1-8 | Me | Q3-10 |
| Q1-8 | Me | Q3-11 |
| Q1-8 | Me | Q3-12 |
| Q1-8 | Me | Q3-13 |
| Q1-8 | Me | Q3-14 |
| Q1-8 | Me | Q3-15 |
| Q1-8 | Me | Q3-16 |
| Q1-8 | Me | Q3-17 |
| Q1-8 | Me | Q3-18 |
| Q1-8 | Me | Q3-19 |
| Q1-8 | Me | Q3-20 |
| Q1-8 | Me | Q3-21 |
| Q1-8 | Me | Q3-22 |
| Q1-8 | Me | Q3-23 |

(60) The compounds according to (59), wherein R$^1$ is converted to a hydrogen atom, tautomers, prodrugs or pharmaceutically acceptable salts of the compounds or solvates thereof.

(61) The compounds according to (59), wherein R$^1$ is converted to a trifluoromethyl group, tautomers, prodrugs or pharmaceutically acceptable salts of the compounds or solvates thereof.

(62) The compounds according to (59), wherein R$^1$ is converted to an ethyl group, tautomers, prodrugs or pharmaceutically acceptable salts of the compounds or solvates thereof.

(63) The compounds according to (59), wherein R$^1$ is converted to a n-propyl group, tautomers, prodrugs or pharmaceutically acceptable salts of the compounds or solvates thereof.

(64) The compounds according to (59), wherein R$^1$ is converted to an i-propyl group, tautomers, prodrugs or pharmaceutically acceptable salts of the compounds or solvates thereof.

(65) Thrombopoietin receptor activators represented by the compounds according to any of (1) to (64).

(66) Preventive, therapeutic and improving agents for diseases against which activation of the thrombopoietin receptor is effective, which contain the thrombopoietin receptor activators according to (65) or represented by the formula (I), tautomers, prodrugs or pharmaceutically acceptable salts of the activators or solvates thereof, as an active ingredient.

(67) Platelet increasing agents containing the thrombopoietin receptor activators according to (65) or represented by the formula (I), tautomers, prodrugs or pharmaceutically acceptable salts of the activators or solvates thereof, as an active ingredient.

(68) Medicaments containing the compounds according to any of (1) to (64) or represented by the formula (I), tautomers, prodrugs or pharmaceutically acceptable salts of the compounds or solvates thereof, as an active ingredient.

In the present invention, the compounds of the present invention represented by the formula (I) may be present in the form of tautomers or geometrical isomers which undergo endocyclic or exocyclic isomerization, mixtures of tautomers or geometric isomers or mixtures of thereof. When the compounds of the present invention have an asymmetric center, whether or not resulting from an isomerization, the compounds of the present invention may be in the form of resolved optical isomers or in the form of mixtures containing them in certain ratios.

This will be explained in reference to pyrazole compounds represented by the formula (VI) wherein $R^2$=H, and Y is an oxygen atom. Namely, the compounds represented by the formula (VI) may be present in the form of pyrazolones resulting from tautomerization as shown below, mixtures therefore, or mixtures of isomers thereof. When the compounds of the present invention have optically active forms, diastereomers or geometrical isomers, the present invention covers mixtures of thereof and resolved forms thereof.

Methods for selecting or producing appropriate prodrugs are disclosed, for example, in Design of Prodrugs (Elsevier, Amsterdam 1985).

When a compound of the present invention has a hydroxyl group, acyloxy derivatives obtained by reacting the compound with appropriate acyl halides or appropriate acid anhydrides may, for example, be mentioned as prodrugs. Acyloxys particularly preferred as prodrugs include —OCOC$_2$H$_5$, —OCO(t-Bu), —OCOC$_{15}$H$_{31}$, —OCO (m-CO$_2$Na-Ph), —OCOCH$_2$CH$_2$CO$_2$Na, —OCOCH(NH$_2$)CH$_3$, —OCOCH$_2$N(CH$_3$)$_2$ and the like.

When a compound of the present invention has an amino group, amide derivatives obtained by reacting the compound

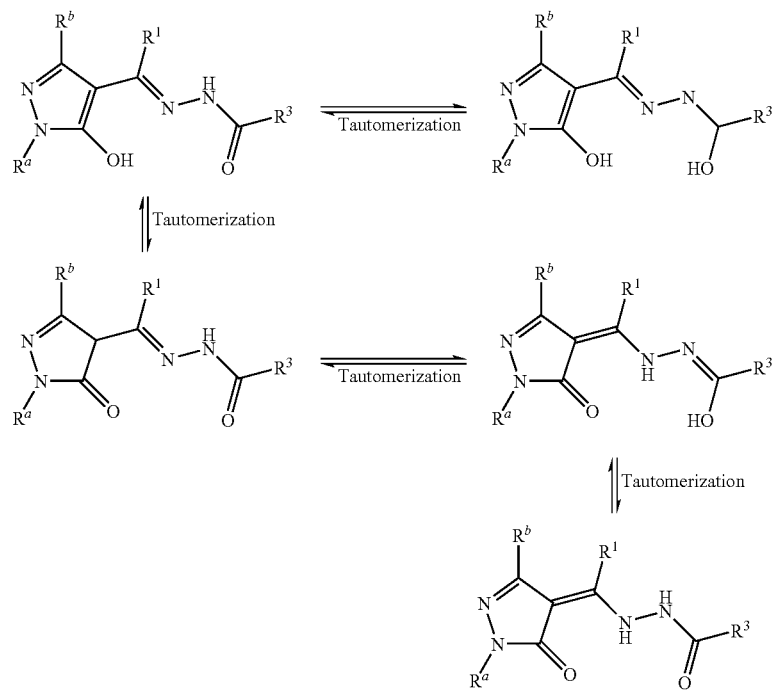

The compounds of the present invention represented by the formula (1) or pharmaceutically acceptable salts thereof may be in the form of arbitrary crystals or arbitrary hydrates, depending on the production conditions. The present invention covers these crystals, hydrates and mixtures. They may be in the form of solvates with organic solvents such as acetone, ethanol and tetrahydrofuran, and the present invention covers any of these forms.

The compounds of the present invention represented by the formula (I) may be converted to pharmaceutically acceptable salts or may be liberated from the resulting salts, if necessary. The pharmaceutically acceptable salts of the present invention may be, for example, salts with alkali metals (such as lithium, sodium and potassium), alkaline earth metals (such as magnesium and calcium), ammonium, organic bases and amino acids. They may be salts with inorganic acids (such as hydrochloric acid, hydrobromic acid, phosphoric acid and sulfuric acid) and organic acids (such as acetic acid, citric acid, maleic acid, fumaric acid, tartaric acid, benzenesulfonic acid and p-toluenesulfonic acid).

The compounds which serve as prodrugs are derivatives of the present invention having chemically or metabolically degradable groups which give pharmacologically active compounds of the present invention upon solvolysis or under physiological conditions in vivo.

having an amino group with appropriate acid halides or appropriate mixed acid anhydrides may, for example, be mentioned as prodrugs. Amides particularly preferred as prodrugs include —NHCO(CH$_2$)$_{20}$OCH$_3$, —NHCOCH(NH$_2$)CH$_3$ and the like.

When a compound of the present invention has a carboxyl group, carboxylate esters obtained by reacting the compound with aliphatic alcohols or with the free alcoholic hydroxyl groups in 1,2- or 1,3-diglycerides may, for example, be mentioned as prodrugs. Particularly preferred as prodrugs are methyl esters and ethyl esters.

The preventive, therapeutic and improving agents for diseases against which activation of the thrombopoietin receptor is effective or platelet increasing agents which contain the thrombopoietin receptor activators of the present invention, tautomers, prodrugs or pharmaceutically acceptable salts of the activators or solvates thereof as an active ingredient may usually be administered as oral medicines such as tablets, capsules, powder, granules, pills and syrup, as rectal medicines, percutaneous medicines or injections. The agents of the present invention may be administered as a single therapeutic agent or as a mixture with other therapeutic agents. Though they may be administered as they are, they are usually administered in the form of pharmaceutical compositions.

These pharmaceutical preparations can be obtained by adding pharmacologically and pharmaceutically acceptable additives by conventional methods. Namely, for oral medicines, ordinary additives such as excipients, lubricants, binders, disintegrants, humectants, plasticizers and coating agents may be used. Oral liquid preparations may be in the form of aqueous or oily suspensions, solutions, emulsions, syrups or elixirs or may be supplied as dry syrups to be mixed with water or other appropriate solvents before use. Such liquid preparations may contain ordinary additives such as suspending agents, perfumes, diluents and emulsifiers.

In the case of rectal administration, they may be administered as suppositories. Suppositories may use an appropriate substance such as cacao butter, laurin tallow, Macrogol, glycerogelatin, Witepsol, sodium stearate and mixtures thereof as the base and may, if necessary, contain an emulsifier, a suspending agent, a preservative and the like.

For injections, pharmaceutical ingredients such as distilled water for injection, physiological saline, 5% glucose solution, propylene glycol and other solvents or solubilizing agents, a pH regulator, an isotonizing agent and a stabilizer may be used to form aqueous dosage forms or dosage forms which need dissolution before use.

The dose of the agents of the present invention for administration to human is usually about from 0.1 to 1000 mg/human/day in the case of oral drugs or rectal administration and about from 0.05 mg to 500 mg/human/day in the case of injections into an adult, though it depends on the age and conditions of the patient. The above-mentioned ranges are mere examples, and the dose should be determined from the conditions of the patient.

The present invention is used when the use of compounds which have thrombopoietin receptor affinity and act as thrombopoietin receptor agonists are expected to improve pathological conditions. For example, hematological disorders accompanied by abnormal platelet count may be mentioned. Specifically, it is effective for therapy or prevention of human and mammalian diseases caused by abnormal megakaryopoiesis, especially those accompanied by thrombocytopenia. Examples of such diseases include thrombocytopenia accompanying chemotherapy or radiotherapy of cancer, thrombocytopenia accompanying antiviral therapy for diseases such as hepatitis C, thrombocytopenia caused by bone marrow transplantation, surgery and serious infections, or gastrointestinal bleeding, but such diseases are not restricted to those mentioned. Typical thrombocytopenias such as aplastic anemia, idiopathic thrombocytopenic purpura, myelodysplastic syndrome, hepatic disease, HIV infection and thrombopoietin deficiency are also targets of the agents of the present invention.

The present invention may be used as a peripheral stem cell mobilizer, a megakaryoblastic or megakaryocytic leukemia cell differentiation inducer and a platelet increasing agent for platelet donors. In addition, potential applications include therapeutic angiogenesis based on differentiation and proliferation of vascular endothelial cells and endothelial progenitor cells, prevention and therapy of arteriosclerosis, myocardial infarction, unstable angina, peripheral artery occlusive disease, but there is no restriction.

The compounds represented by the formula (I) such as pyrazole compounds represented by the formula (VI) are prepared by the process represented by the formula (1) illustrated below.

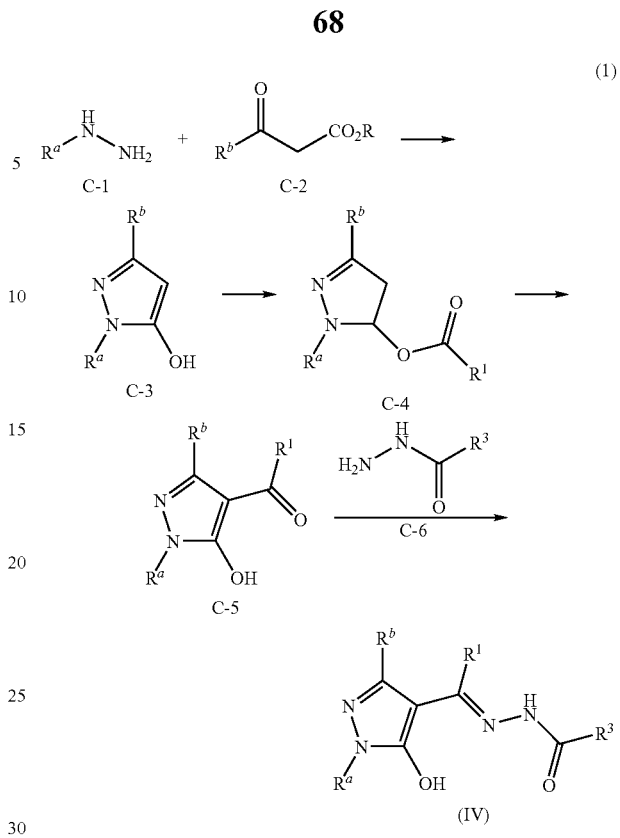

A pyrazolone (C-3) is synthesized by known processes (Syn. Comm., 20(20), 3213 (1990), Chem. Ber., 59, 320 (1926), Monatsh. Chem., 89, 30 (1958)), for example, by reacting a β-ketoester (C-2) with a hydrazine ($R^a$NHNH$_2$ (C-1) or a salt thereof) in acetic acid under reflux, and then converted to a 4-acyl-5-hydroxypyrazole (C-5) by acylation (C-4) with an acyl halide ($R^1$COOCl) or acid anhydride (($R^1$CO)$_2$O) followed by Fries rearrangement in the presence of potassium carbonate in dioxane with heating. A 4-formyl-5-hydroxypyrazole (C-5) ($R^1$=H) is obtainable by reacting a pyrazolone (C-3) with POCl$_3$-DMF. These pyrazoles are heated with a hydrazide ($R^3$CONHNH$_2$ (C-6) or a salt thereof) in a solvent with stirring, if necessary in the presence of a catalyst, to give the desired product. The hydrazide (C-6) can be synthesized by known methods for which the following are referred to.

(1) Synthetic Commun., 28(7)1223-1231 (1998)
(2) J. Chem. Soc., 1225 (1948)
(3) J. Chem. Soc., 2831 (1952)
(4) WO03/7328
(5) Journal of the Chemical Society of Japan, 88(5), 73 (1967)
(6) Journal of Heteroctyclic Chemistry, 28(17), 17 (1991)

The compounds represented by the formula (I) such as pyrazole compounds represented by the formula (VI) are also prepared by the process represented by the formula (2) illustrated below.

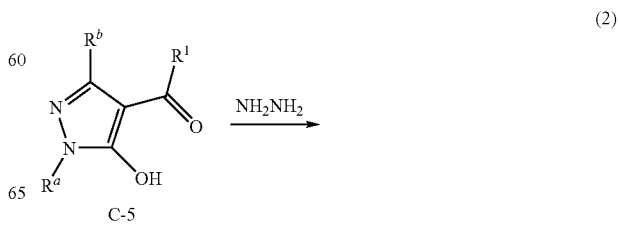

-continued

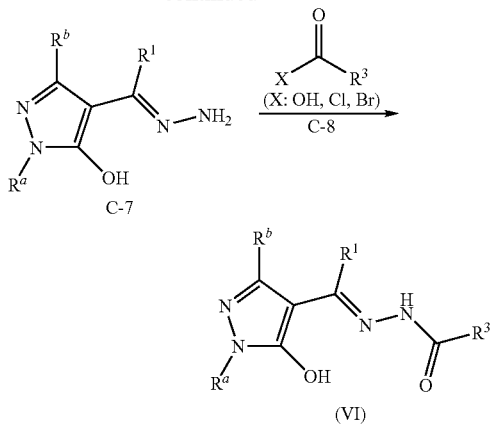

A compound (C-7) is obtainable by heating a compound (C-5) and hydrazine or a synthetic equivalent thereof in a solvent with stirring, if necessary in the presence of a catalyst.

The compound (C-7) is stirred with a compound (C-8) in a solvent, if necessary in the presence of a catalyst, a dehydrating condensation agent or a base, if necessary with heating to give the desired product or a precursor thereof. The precursor is converted to the desired product by hydrolysis, deprotection, reduction, oxidation or the like, depending on the precursor.

The compounds of the present invention can usually be purified by column chromatography, thin layer chromatography, high performance liquid chromatography HPLC), high performance liquid chromatography-mass spectrometry (LC-MS) and, if necessary, are obtainable with high purity by recrystallization or washing with a solvent.

Other starting materials for synthesis of the compounds represented by the formula (I) are known to be obtainable by the following methods. The starting materials for synthesis disclosed therein can be used in the same manner as (C-5) in the formula (1) to synthesize the compounds of the present invention represented by the formula (I).

(1) The starting material for synthesis of the compounds represented by the formula (V)

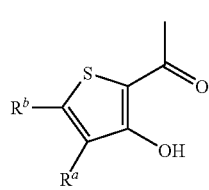

is obtainable from the following (C-9) synthesized in accordance with Journal of Heterocyclic Chemistry, 27(2), 315 (1990), by the method disclosed in WO04/108683.

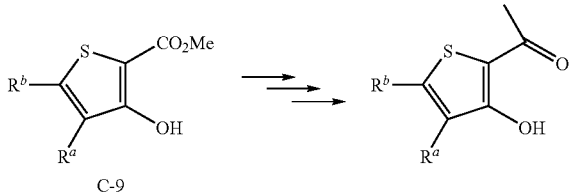

(2) The starting material for synthesis represented by the following formula

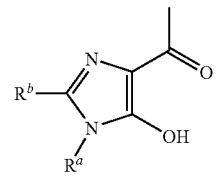

is obtainable from the following (C-10) synthesized in accordance with Zhurnal Obshchei Khimii, 47(5), 1201 (1977), by the method disclosed in WO04/108683.

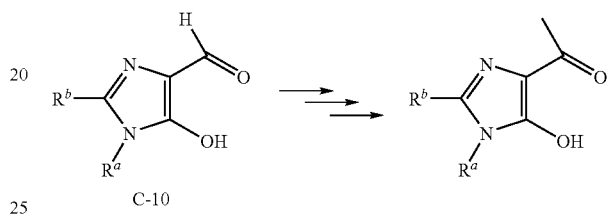

(3) The starting material for synthesis represented by the following formula

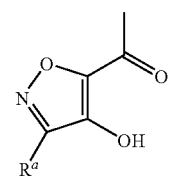

is obtainable from the following (C-11) synthesized in accordance with Journal of Organic Chemistry, 54(3), 706 (1989), by the method disclosed in WO04/108683.

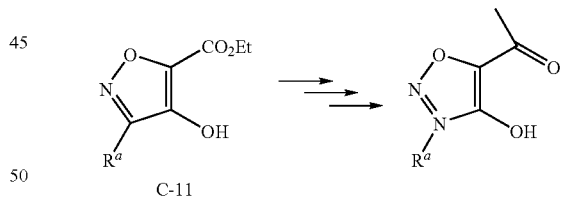

(4) The starting material for synthesis represented by the following formula

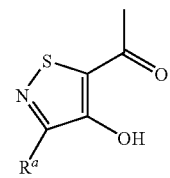

is obtainable from the following (C-12) synthesized in accordance with Eur. Pat. Appl., 48615 (1982), by the method disclosed in WO04/108683.

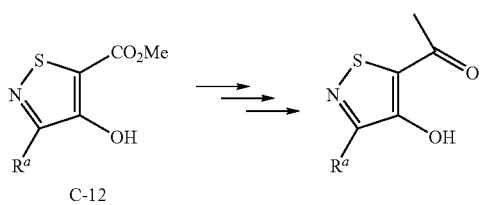

C-12

(5) The starting material for synthesis represented by the following formula

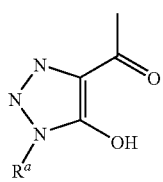

is obtainable from the following (C-13) synthesized in accordance with Acta Chemica Scandinavica, 22(8), 2476 (1968), by the method disclosed in WO04/108683.

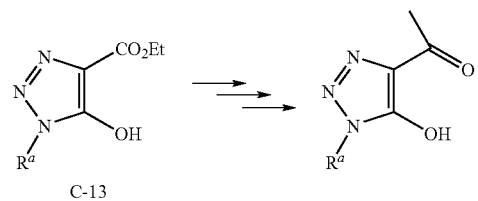

C-13

EXAMPLES

Now, the present invention will be described in further detail with reference to Reference Synthetic Examples, Synthetic Examples, Assay Examples and Formulation Examples. However, it should be understood that the present invention is by no means restricted by these specific Examples.

LC/MS was measured under the following conditions.
LC/MS Condition 1
  Column: Waters SunFire C18 (3.5 μm, 4.6×30 mm)
  Eluent: acetonitrile/0.1% aqueous formic acid (10/90→60/40)
LC/MS Conditions 2
  Column: Waters Xterra MSC18 (5 μm, 4.6×50 mm)
  Eluent: acetonitrile/0.1% aqueous formic acid (10/90→60/40)
LC/MS Conditions 3
  Column: Waters Xterra MSC18 (3.5 μm, 2.1×20 mm)
  Eluent: acetonitrile/0.2% aqueous formic acid (20/80→90/10)

Reference Synthetic Example 1

1-[1-(4-t-Butylphenyl)-5-hydroxy-3-methyl-1H-pyrazol-4-yl]-ethanone (1) 1-(4-t-Butylphenyl)-5-hydroxy-3-methyl-1H-pyrazole
4-t-Butylphenylhydrazine hydrochloride (24.2 g, 120 mmol) in acetic acid (600 mL) was stirred with ethyl acetoacetate (16.4 mL, 129 mmol) at 100° C. for 22 hours. The solvent was removed by distillation under reduced pressure, and the resulting solid was recrystallized from chloroform (70 ml, 40° C.)-diethyl ether (200 mL, 0° C.), washed with diethyl ether and dried under reduced pressure to give 21.7 g of the desired product (78% yield).

Morphology: colorless solid
LC/MS: Condition 2, retention time 3.52 (min)
LC/MS (ESI$^+$) m/z; 231 [M+1]

(2) 5-Acetyloxy-1-(4-t-butylphenyl)-3-methyl-1H-pyrazole 1-(4-t-Butylphenyl)-5-hydroxy-3-methyl-1H-pyrazole (21.7 g, 94.1 mmol) in tetrahydrofuran (600 mL) was mixed with triethylamine (26.2 mL, 188 mmol.) and acetyl chloride (7.4 mL, 104 mmol) at 0° C. and stirred at room temperature for 45 minutes. The reaction solution was mixed with water (300 mL), and the aqueous layer and the organic layer were separated. The solvent was removed from the organic layer by distillation, and the residue was mixed with ethyl acetate. The aqueous layer was extracted with ethyl acetate twice, and the extract was combined with the organic layer. The combined organic layer was washed with saturated aqueous sodium hydrogen carbonate once, with water twice and with saturated aqueous sodium chloride, dried over anhydrous sodium sulfate and filtered. The filtrate was concentrated to give 22.2 g of the desired product (87% yield).

Morphology: brown oil
LC/MS: Condition 2, retention time 4.37 (min)
LC/MS (ESI$^+$) m/z; 273 [M+1]

(3) 1-[1-(4-t-Butylphenyl)-5-hydroxy-3-methyl-1H-pyrazol-4-yl]-ethanone

5-Acetyloxy-1-(4-t-butylphenyl)-3-methyl-1H-pyrazole (4.21 g, 15.5 mmol) in 1,4-dioxane (150 mL) was stirred with potassium carbonate (2.14 g, 15.5 mmol) at 110° C. for 3.5 hours, and after addition of water (50 mL), the organic solvent was removed by distillation. Then, ethyl acetate, water and 6 M hydrochloric acid were added to adjust the aqueous layer to pH 2, and the aqueous layer and the organic layer were separated. The aqueous layer was extracted with ethyl acetate twice, and the organic layer was combined with the extract, washed with saturated aqueous ammonium chloride three times and with saturated aqueous sodium chloride once and dried over anhydrous sodium sulfate and filtered. The solvent was removed by distillation, and the residue was purified by silica gel column chromatography (hexane/ethyl acetate=6/1→3/1→1/1) to give 2.77 g of the desired product (66% yield).

Morphology: yellow solid
LC/MS: Condition 1, retention time 4.14 (min)
LC/MS (ESI$^+$) m/z; 273 [M+1]
LC/MS (ESI$^-$) m/z; 271 [M−1]*

Reference Synthetic Examples 2 to 5

Compounds were synthesized in the same manner as in Reference Synthetic Example 1, and the morphology of the resulting compounds, the LC/MS conditions used for their analysis and the observed peaks and retention times are shown in Table 7.

TABLE 7

| Reference Synthetic Example No. | Morphology | LC/MS conditions | Observed peak (ESI⁺) | Observed peak (ESI⁻) | Retention time (min) |
|---|---|---|---|---|---|
| 2 | Orange solid | 1 | 285, 287 | 283, 285 | 4.32 |
| 3 | Brown solid | 1 | 285 | 283 | 3.97 |
| 4 | Light brown solid | 1 | 245 | 243 | 3.50 |
| 5 | Yellow solid | 1 | 295, 297 | 293, 295 | 3.69 |

Reference Synthetic Example 6

Methyl 1-hydrazinothiocarbonylpiperidine-4-carboxylate

Methyl isonipecotinate (1.0 g, 6.98 mmol) in tetrahydrofuran was mixed with thiocarbonyldiimidazole (1.24 g, 6.98 mmol) at room temperature and then stirred at room temperature for 1.5 hours and stirred with hydrazine monohydrate (700 mg, 14.0 mmol) for another 4 hours. The reaction solution was mixed with saturated aqueous sodium chloride and extracted with ethyl acetate and chloroform. The extract was dried over anhydrous magnesium sulfate and filtered, and the filtrate was concentrated to give the crude preparation of the desired product (114% yield).
Morphology: pale yellow solid
LC/MS: Condition 3, retention time 0.52 (min)
LC/MS (ESI⁺) m/z; 218 [M+1]

Reference Synthetic Example 7

Ethyl 1-hydrazinothiocarbonylpiperazine-4-acetate

Ethyl piperazine-1-acetate (680 mg, 3.71 mmol) in tetrahydrofuran (8.0 mL) was mixed with triethylamine (0.776 mL, 5.57 mmol) and thiocarbonyldiimidazole (992 mg, 5.57 mmol) at room temperature and stirred at room temperate for 2 hours and then stirred with hydrazine monohydrate (0.272 mL, 5.57 mmol) for another 2 hours. The reaction solution was mixed with saturated aqueous sodium chloride and extracted with ethyl acetate. The extract was dried over anhydrous magnesium sulfate and filtered, and the filtrate was concentrated to give the crude preparation of the desired product (115% yield).
Morphology: white solid
LC/MS: Condition 1, retention time 0.37 (min)
LC/MS (ESI⁺) m/z; 247 [M+1]
LC/MS (ESI⁻) m/z; 245 [M−1]

Reference Synthetic Example 8

Ethyl 1-hydrazinothiocarbonylpiperazine-4-oxoacetate

1-Boc-piperazine (1.06 g, 5.62 mmol) in acetonitrile (10 mL) was mixed with triethylamine (1.19 mL, 8.54 mmol) at room temperature and with ethyl 1-chloro-1-oxoacetate (0.709 mL, 6.26 mmol) and acetonitrile (18 mL) at 0° C. and stirred at room temperature overnight. The reaction solution was partly concentrated, mixed with water and extracted with ethyl acetate. The extract was washed with saturated aqueous ammonium chloride, saturated aqueous sodium bicarbonate and saturated aqueous sodium chloride, dried over anhydrous magnesium sulfate and filtered. The filtrate was concentrated to give a crude preparation of ethyl 1-Boc-piperazine-4-oxoacetate (109% yield, red liquid). The crude preparation was stirred with dioxane (12 mL) and hydrochloric acid/dioxane (4 mol/l, 7.8 mL, 31.12 mmol) at 80° C. for 4 hours and concentrated to give ethyl piperazine-4-oxoacetate hydrochloride (125% yield, yellow solid). The resulting ethyl piperazine-4-oxoacetate hydrochloride (553 mg, 2.48 mmol) in tetrahydrofuran (25 mL) was mixed with triethylamine (0.519 mL, 3.72 mmol) and thiocarbonyldiimidazole (664 mg, 3.72 mmol) at room temperature, stirred at room temperature for 2 hours and then stirred with hydrazine monohydrate (0.182 mL, 3.72 mmol) for 2 hours. The reaction solution was mixed with saturated aqueous sodium chloride and extracted with ethyl acetate, and the extract was dried over anhydrous magnesium sulfate and filtered. The filtrate was concentrated to give a crude preparation of the desired product (72% yield), which was used for the next reaction without purification.
Morphology: red liquid The structures of the compounds obtained in Reference Synthetic Examples are shown below.

Reference Synthetic Example 1

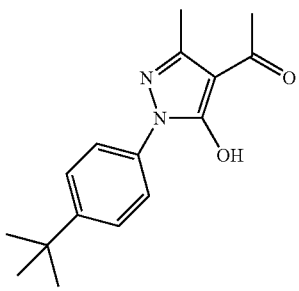

Reference Synthetic Example 2

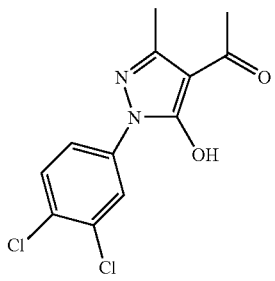

Reference Synthetic Example 3

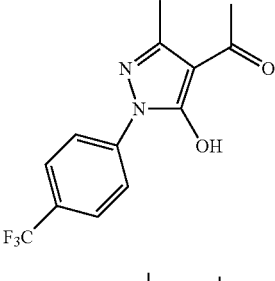

Reference Synthetic Example 4

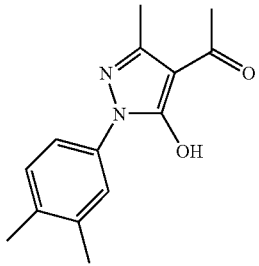

-continued

Reference Synthetic Example 5

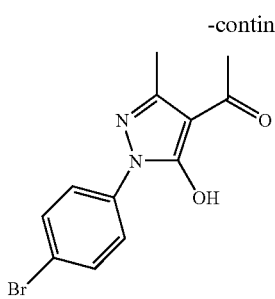

Reference Synthetic Example 7

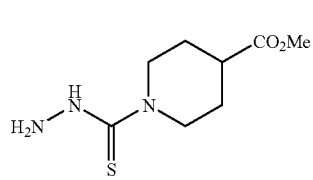

Reference Synthetic Example 7

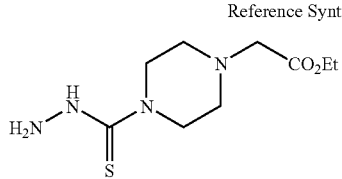

Reference Synthetic Example 8

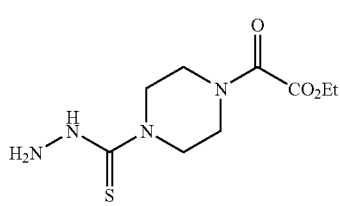

Synthetic Example 1

1-(N'-{1-[(4-t-Butylphenyl)-3-methyl-5-oxo-1,5-dihydro-pyrizol-4-ylidene]-ethyl}-hydrazinothiocarbonyl)-piperidine-4-carboxylic Acid (1) Methyl 1-(N'-{1-[1-(4-t-butylphenyl)-3-methyl-5-oxo-1,5-dihydro-pyrizol-4-ylidene]-ethyl}-hydrazinothiocarbonyl)-piperidine-4-carboxylate A dimethylformamide solution (3.0 mL) of 1-[1-(4-t-butylphenyl)-5-hydroxy-3-methyl-1H-pyrazol-4-yl]-ethanone (85.3 mg, 0.323 mmol) prepared in Reference Synthetic Example 1 and methyl 1-hydrazinothiocarbonylpiperidine-4-carboxylate (220 mg, 1.01 mmol) prepared in Reference Synthetic Example 6 was stirred with concentrated hydrochloric acid (84.2 µL, 1.01 mmol) at room temperature for 20 hours. After addition of water (5.0 ml) and ethyl acetate (5.0 ml), the aqueous layer and the organic layer were separated, and the aqueous layer was extracted with ethyl acetate twice. The extract was combined with the organic layer, washed with saturated aqueous ammonium chloride three times, with water once and with saturated aqueous sodium chloride once, then dried over anhydrous sodium sulfate and filtered. The solvent was removed by vacuum distillation. The resulting solid was washed with 2-propanol and water and dried under reduced pressure to give 94.3 mg of the desired product (64% yield).

Morphology: light brown solid
LC/MS: Condition 1, retention time 4.25 (min)
LC/MS (ESI$^+$) m/z; 472 [M+1]
LC/MS (ESI$^-$) m/z; 470 [M−1]

(2) 1-(N'-{1-[1-(4-t-Butylphenyl)-3-methyl-5-oxo-1,5-dihydro-pyrazol-4-ylidene]-ethyl}-hydrazinothiocarbonyl)-piperidine-4-carboxylic acid Methyl 1-(N'-{1-[1-(4-t-butylphenyl)-3-methyl-5-oxo-1,5-dihydro-pyrazol-4-ylidene]-ethyl}-hydrazinothiocarbonyl)-piperidine-4-carboxylate (89.6 mg, 0.190 mmol) in methanol (3.0 mL) was stirred with 1 M aqueous sodium hydroxide (570 µL, 0.570 mmol) at room temperature for 11 hours, with 1 M aqueous sodium hydroxide (380 µL, 0.380 mmol) at room temperature for 3 hours and then with 1 M hydrochloric acid (950 µL, 0.950 mmol) and water at room temperature for another 30 minutes. The resulting precipitate was collected by filtration, washed with water and methanol and dried under reduced pressure to give 47.7 mg of the desired product (55% yield).

Morphology: colorless solid
LC/MS: Condition 3, retention time 4.38 (min)
LC/MS (ESI$^+$) m/z; 458 [M+1]
LC/MS (ESI$^-$) m/z; 456 [M−1]

Synthetic Example 2

1-(N'-{1-[1-(3,4-Dichlorophenyl)-3-methyl-5-oxo-1,5-dihydro-pyrazol-4-ylidene]ethyl}-hydrazinothiocarbonyl)-piperidine-4-carboxylic acid Synthesis was carried out in the same manner as in Synthetic Example 1 by using the compound prepared in Reference Synthetic Example 2 and the compound prepared in Reference Synthetic Example 6 to give 26.9 mg of the desired product (44% yield).

Morphology: pink solid
LC/MS: Condition 3, retention time 3.87 (min)
LC/MS (ESI$^+$) m/z; 470 [M+1], 472 [M+3]
LC/MS (ESI$^-$) m/z; 468 [M−1], 470 [M+1]

Synthetic Example 3

1-(N'-{1-[3-Methyl-5-oxo-1-(4-trifluoromethylphenyl)-1,5-dihydro-pyrazol-4-yliden]-ethyl}-hydrazinothiocarbonyl)-piperidine-4-carboxylic acid Synthesis was carried out in the same manner as in Synthetic Example 1 by using the compound prepared in Reference Synthetic Example 3 and the compound prepared in Reference Synthetic Example 6 to give 109.1 mg of the is desired product (79% yield).

Morphology: orange solid
LC/MS: Condition 1, retention time 3.72 (min)
LC/MS (ESI$^+$) m/z; 470 [M+1]
LC/MS (ESI$^-$) m/z; 468 [M−1]

Synthetic Example 4

Methyl 1-(N'-{1-[1-(3,4-dimethylphenyl)-3-methyl-5-oxo-1,5-dihydro-pyrazol-4-yliden]-ethyl}-hydrazinothiocarbonyl)-piperidine-4-carboxylate Synthesis was carried out in the same manner as in Synthetic Example 1(1) by using the compound prepared in Reference Synthetic Example 4 and the compound prepared in Reference Synthetic Example 6 to give 68.0 mg of the desired product (93% yield).

Morphology: pale gray solid
LC/MS: Condition 3, retention time 4.25 (min)
LC/MS (ESI$^+$) m/z; 444 [M+1]

Synthetic Example 5

1-(N'-{1-[1-(3,4-Dimethylphenyl)-3-methyl-5-oxo-1,5-dihydro-pyrazol-4-ylidene]-ethyl}-hydrazinothiocarbonyl)-piperidine-4-carboxylic acid Synthesis was carried out in the same manner as in Synthetic Example 1(2) by using methyl 1-(N'-{1-[1-(3,4-dimethylphenyl)-3-methyl-5-oxo-1,5-dihydro-pyrazol-4-yliden]-ethyl}-hydrazinothiocarbonyl)-piperidine-4-carboxylate prepared in Synthetic Example 4 to give 40.0 mg of the desired product (86% yield).
Morphology: gray solid
LC/MS: Condition 3, retention time 3.88 (min)
LC/MS (ESI$^+$) m/z; 430 [M+1]

Synthetic Example 6

1-(N'-{1-[1-(4-Bromophenyl)-3-methyl-5-oxo-1,5-dihydro-pyrazol-4-ylidene]-ethyl}-hydrazinothiocarbonyl)-piperidine-4-carboxylic acid Synthesis was carried out in the same manner as in Synthetic Example 1 by using the compound prepared in Reference Synthetic Example 5 and the compound prepared in Reference Synthetic Example 6 to give 25.1 mg of the desired product (60% yield).
Morphology: pale yellow solid
LC/MS: Condition 1, retention time 3.57 (min)
LC/MS (ESI$^+$) m/z; 480 [M+1], 482 [M+3]
LC/MS (ESI$^-$) m/z; 478 [M−1], 480 [M+1]

Synthetic Example 7

Ethyl[4-(N'-{1-[1-(4-t-butylphenyl)-3-methyl-5-oxo-1,5-dihydro-pyrazol-4-ylidene]-ethyl}-hydrazinothiocarbonyl)-piperazin-1-yl]-acetate The compound prepared in Reference Synthetic Example 1 and the compound prepared in Reference Synthetic Example 7 were reacted in the same manner as in Synthetic Example 1(1), and the reaction solution was mixed with water and filtered. The filter cake was washed with chloroform/n-hexane to give 177.3 mg of the desired product (60% yield).
Morphology: yellow solid
LC/MS: Condition 1, retention time 3.47 (min)
LC/MS (ESI$^+$) m/z; 501 [M+1]
LC/MS (ESI$^-$) m/z; 499 [M−1]

Synthetic Example 8

[4-(N'-{1-[1-(4-t-Butylphenyl)-3-methyl-5-oxo-1,5-dihydro-pyrazol-4-ylidene]-ethyl}-hydrazinothiocarbonyl)-piperazin-1-yl]-acetic acid Synthesis was carried out in the same manner as in Reference Synthetic Example 1(2) by using ethyl[4-(N'-{1-[1-(4-t-butylphenyl)-3-methyl-5-oxo-1,5-dihydro-pyrazol-4-ylidene]-ethyl}-hydrazinothiocarbonyl)-piperazin-1-yl]-acetate prepared in Synthetic Example 7 to give 38.4 mg of the desired product (57% yield).
Morphology: yellow solid
LC/MS: Condition 1, retention time 3.19 (min)
LC/MS (ESI$^+$) m/z; 473 [M+1]
LC/MS (ESI$^-$) m/z; 471 [M−1]

Synthetic Example 9

[4-(N'-{1-[1-(4-t-Butylphenyl)-3-methyl-5-oxo-1,5-dihydro-pyrazol-4-ylidene]-ethyl}-hydrazinothiocarbonyl)-piperazin-1-yl]-oxoacetic acid Synthesis was carried out in the same manner as in Synthetic Example 1 by using the compound prepared in Reference Synthetic Example 1 and the compound prepared in Reference Synthetic Example 8 to give 70.9 mg of the desired product (52% yield after hydrolysis, 30% total is yield).
Morphology: pale yellow solid
The structures of the compounds obtained in Synthetic Examples are shown below.

Synthetic Example 1

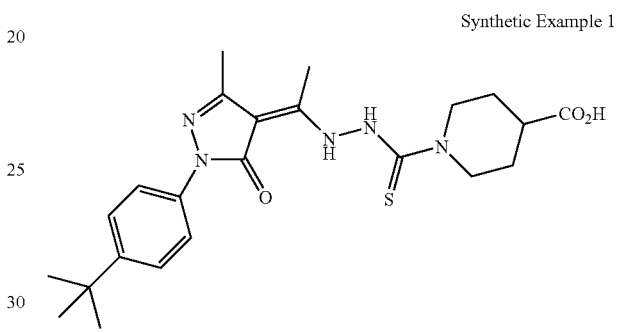

Synthetic Example 2

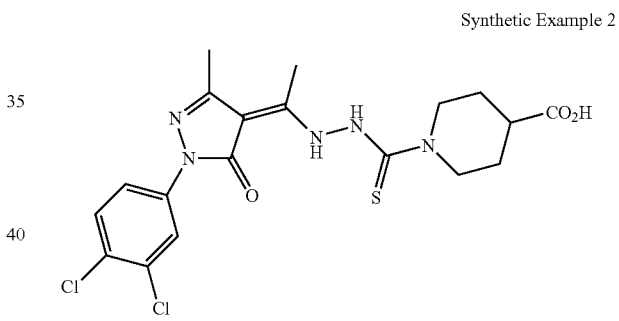

Synthetic Example 3

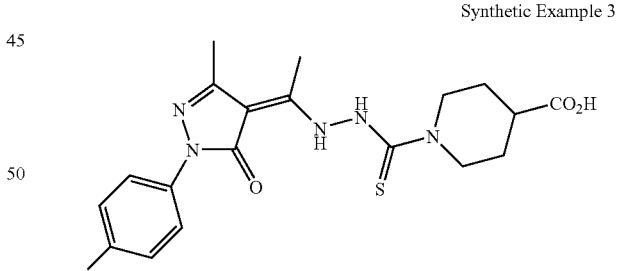

Synthetic Example 4

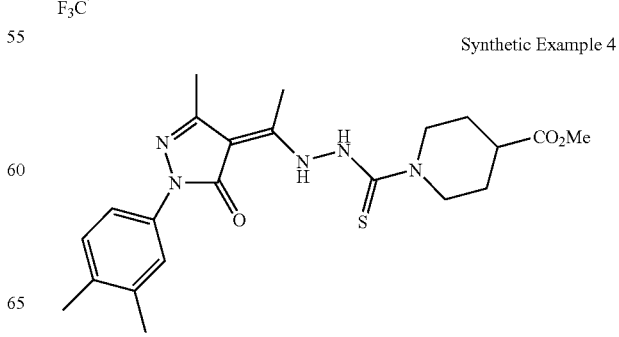

Synthetic Example 5

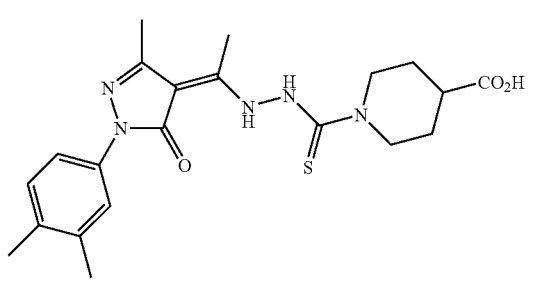

Synthetic Example 6

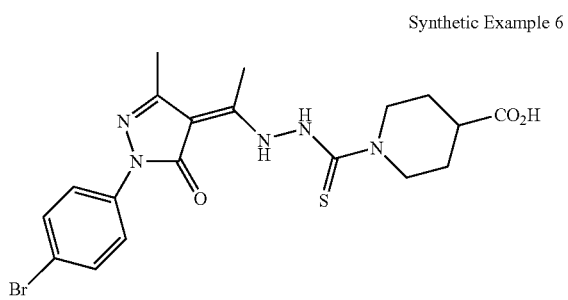

Synthetic Example 7

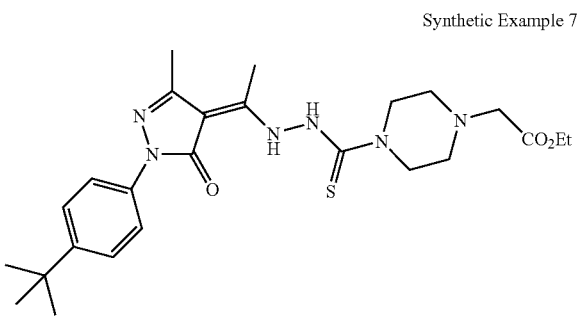

Synthetic Example 8

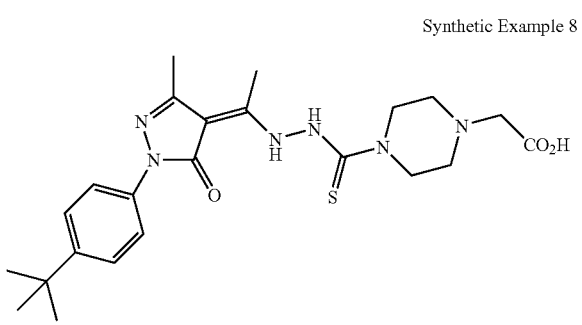

Synthetic Example 9

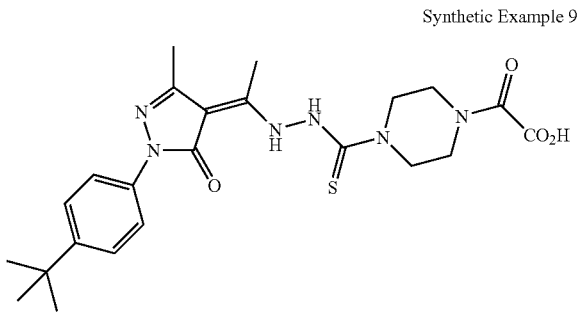

Assay Example 1

Stimulation of Proliferation of a Thrombopoietin-Dependent Cell Line

The responses of thrombopoietin receptor to the compounds of the present invention prepared in the Synthetic Examples were assayed using a human leukemic cell line, UT7/EPO-mpl.

(1) Cells and Cell Culture

UT7/EPO-mpl is a stable transformed cell line obtained by introducing into human leukemic cell line UT7/EPO a vector that induces expression of human thrombopoietin receptor (c-mpl) under control of cytomegalovirus immediate-early promoter by the method of Takatoku et al. (J. Biol. Chem., 272:7259-7263 (1997)). Proliferation of this cell line is stimulated by TPO, while its mother cell line UT7/EPO exhibits no response to TPO. These two cell lines were subcultured in IMDM (GIBCO) containing 10% fetal bovine serum (Thermo Electron or BioWest) using a $CO_2$ incubator (5% $CO_2$, 37° C.).

(2) Cell Proliferation Assay

The subcultured cells described above were washed twice with PBS and suspended in IMDM containing 10% fetal bovine serum at a cell density of $6 \times 10^4$ cells/ml. The cell suspension was transferred to a 96-well tissue culture plate (CORNING) in 100-µl aliquots. Then either thrombopoietin (Pepro Tech EC) or the compounds of the Synthetic Examples dissolved in dimethyl sulfoxide were diluted 83-fold with IMDM containing 10% fetal bovine serum and added to the aforementioned cell suspension in 20-µl aliquots. The cell suspension was incubated in a $CO_2$ incubator (5% $CO_2$, 37° C.) for 4 days. Cell proliferation was assayed using WST-8 reagent (Kishida Chemical Co., Ltd.) according to instructions by the manufacturer. A 10-µl aliquot of 5 mM WST-8 reagent solution was added to each well of the tissue culture plate, and the plate was incubated at 37° C. for 4 hours. The formazan pigment generated was detected by measuring the absorbance at 450 nm with a 96-well microplate reader (Nihon Molecular Devices, Spectramax 190).

Proliferation of thrombopoietin-responsive UT7/EPO-mpl cells was stimulated by the compounds of the Synthetic Examples in a concentration-dependent manner, while no effect of this compounds on proliferation was observed with UT7/EPO, the mother cell line. These results indicate that the compound of the Synthetic Examples of the present invention acts on the thrombopoietin receptor selectively as an activator.

The concentration of each compound that yields a growth rate corresponding to 50% of the growth of human leukemic cell line UT-7/EPO-mpl observed in the presence of 10 ng/mL TPO ($EC_{50}$) in the test on the compounds of the Synthetic Examples in Assay Example 1 are shown in Table 8.

TABLE 8

| Synthetic Example No. | $EC_{50}$ (ng/mL) |
|---|---|
| 1 | 2.8 |
| 2 | 3.0 |
| 3 | 2.9 |
| 4 | 31 |
| 5 | 2.8 |
| 6 | 3.1 |
| 7 | 36 |
| 8 | 3.4 |
| 9 | 2.1 |

Formulation Example 1

A granule preparation containing the following ingredients is prepared.
Ingredients

| | |
|---|---|
| Compound represented by the formula (I) | 10 mg |
| Lactose | 700 mg |
| Corn Starch | 274 mg |
| HPC-L | 16 mg |
| | 1000 mg |

A compound represented by the formula (I) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated (extrusion granulation, die size 0.5-1 mm) and dried. The resulting dry granules are sifted through a shaking sieve (12/60 mesh) to obtain a granule preparation.

Formulation Example 2

A powder preparation for capsulation containing the following ingredients is prepared.
Ingredients

| | |
|---|---|
| Compound represented by the formula (I) | 10 mg |
| Lactose | 79 mg |
| Corn Starch | 10 mg |
| Magnesium Stearate | 1 mg |
| | 100 mg |

A compound represented by the formula (I) and lactose are sifted through a 60-mesh sieve. Corn starch is sifted though a 120-mesh sieve. They are mixed with magnesium stearate in a V-type blender. The 10% powder is put in hard gelatin capsules No. 5, 100 mg each.

Formulation Example 3

A granule preparation for capsulation containing the following ingredients is prepared.
Ingredients

| | |
|---|---|
| Compound represented by the formula (I) | 15 mg |
| Lactose | 90 mg |
| Corn Starch | 42 mg |
| HPC-L | 3 mg |
| | 150 mg |

A compound represented by the formula (I) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated and dried. The resulting dry granules are sifted through a shaking sieve (12/60 mesh). The granules are put in hard capsules No. 4, 150 mg each.

Formulation Example 4

A tablet preparation containing the following ingredients is prepared.
Ingredients

| | |
|---|---|
| Compound represented by the formula (I) | 10 mg |
| Lactose | 90 mg |
| Microcrystalline cellulose | 30 mg |
| Magnesium Stearate | 5 mg |
| CMC-Na | 15 mg |
| | 150 mg |

A compound represented by the formula (I), lactose, microcrystalline cellulose and CMC-Na (carboxymethylcellulose sodium salt) are sifted through a 60-mesh sieve and mixed. The powder mixture is mixed with magnesium stearate to give a bulk powder mixture. The powder mixture is compressed directly into 150 mg tablets.

Formulation Example 5

An intravenous preparation is prepared as follows.

| | |
|---|---|
| Compound represented by the formula (I) | 100 mg |
| Saturated Fatty Acid Glyceride | 1000 ml |

Solutions having the above-mentioned composition are usually administered to a patient intravenously at a rate of 1 ml per 1 minute.

INDUSTRIAL APPLICABILITY

The compounds of the present invention which have affinity for thrombopoietin receptor and act as thrombopoietin receptor agonists are useful as preventive, therapeutic and improving agents for diseases against which activation of the thrombopoietin receptor is effective, especially as drugs for hematological disorders accompanied by abnormal platelet count and as drugs for diseases treated or prevented by stimulating differentiation and proliferation of vascular endothelial cells and endothelial progenitor cells, and are useful as medicines.

The entire disclosure of Japanese Patent Application No. 2006-158459 filed on Jun. 7, 2006 including specification, claims and summary is incorporated herein by reference in its entirety.

The invention claimed is:

1. A compound represented by formula (I):

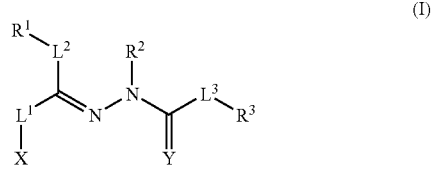

(I)

wherein
each of $R^1$ and $R^2$ independently means a hydrogen atom, or a $C_{1-10}$ alkyl group, wherein the $C_{1-10}$ alkyl group may optionally be substituted with one or more halogen atoms, R³ means a $C_{2-9}$ nitrogen-containing heterocyclyl group, wherein the $C_{2-9}$ nitrogen-containing heterocyclyl group may optionally be substituted with one or more substituents independently represented by substituent set A, wherein substituent set A is a hydrogen atom, a hydroxyl group, a carboxyl group, a sulfo group, a carbamoyl group, a sulfamoyl group, a tetrazole group, a phosphono group, —CH$_2$CO$_2$H, —COCO$_2$H, —SO$_2$R$^{25}$ or —COR$^{25}$, wherein R$^{25}$ means a $C_{1-10}$ alkoxy group, a $C_{2-9}$ heterocyclyl group or NR$^{26}$R$^{27}$, wherein each of R$^{26}$ and R$^{27}$ independently means a hydrogen atom or a $C_{1-10}$ alkyl group, wherein the $C_{1-10}$ alkyl group may optionally be substituted with one or more $C_{2-14}$ aryl groups, L¹-X represents formula (II):

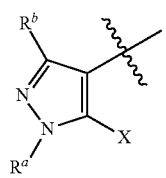

(II)

wherein R$^a$ means a $C_{2-14}$ aryl group that may optionally be substituted with one or more substituents each of which is independently represented by —V$_2$, wherein —V$_2$ means a halogen atom, a $C_{1-6}$-alkyl group or a $C_{1-6}$ alkoxy group, wherein the $C_{1-6}$ alkyl group and the $C_{1-6}$ alkoxy group may be substituted with one or more halogen atoms, wherein R$^b$ means a hydrogen atom, a $C_{1-6}$ alkyl group or a $C_{1-6}$ alkoxy group, wherein the $C_{1-6}$ alkyl group and the $C_{1-6}$ alkoxy group may be substituted with one or more halogen atoms, L² means a single bond,
L³ means a single bond,
X means OH, and
Y means a sulfur atom, a tautomer thereof, or a pharmaceutically acceptable salt thereof.

2. The compound of claim 1, wherein R² is a hydrogen atom, a tautomer thereof or a pharmaceutically acceptable salt thereof.

3. The compound of claim 1, wherein R¹ is a hydrogen atom or a $C_{1-3}$ alkyl group, wherein the $C_{1-3}$ alkyl group may be substituted with one or more halogen atoms, a tautomer thereof or a pharmaceutically acceptable salt thereof.

4. The compound of claim 1, wherein R$^b$ is a hydrogen atom or a $C_{1-3}$ alkyl group, wherein the $C_{1-3}$ alkyl group may be substituted with one or more halogen atoms, a tautomer thereof or a pharmaceutically acceptable salt thereof.

5. The compound of claim 1, wherein R$^a$ is a phenyl group optionally substituted with one or more of a t-butyl group, a methyl group, a methoxy group, a trifluoromethyl group, a trifluoromethoxy group, a chlorine atom, a bromine atom and a fluorine atom, a tautomer thereof or a pharmaceutically acceptable salt thereof.

6. A method of treating thrombocytopenia in a patient in need thereof, comprising administering to the patient an effective amount of at least one compound of claim 1, a tautomer thereof, or a pharmaceutically acceptable salt thereof.

7. A method of treating thrombocytopenia in a patient in need thereof, comprising administering to the patient an effective amount of at least one compound of claim 2, a tautomer thereof, or a pharmaceutically acceptable salt thereof.

8. A method of treating thrombocytopenia in a patient in need thereof, comprising administering to the patient an effective amount of at least one compound of claim 3, a tautomer thereof, or a pharmaceutically acceptable salt thereof.

9. A method of treating thrombocytopenia in a patient in need thereof, comprising administering to the patient an effective amount of at least one compound of claim 4, a tautomer thereof, or a pharmaceutically acceptable salt thereof.

* * * * *